United States Patent
Wang et al.

(10) Patent No.: US 12,150,882 B2
(45) Date of Patent: Nov. 26, 2024

(54) AUXILIARY SUPPORT APPARATUS AND APPLICATION THEREOF

(71) Applicant: Jiangsu Alphay Medical Devices Co., Ltd., Jiangsu (CN)

(72) Inventors: Jiang Wang, Beijing (CN); Jinfeng Ji, Jiangsu (CN)

(73) Assignee: Jiangsu Alphay Medical Devices Co., Ltd., Jiangsu (CN)

( * ) Notice: Subject to any disclaimer, the term of this patent is extended or adjusted under 35 U.S.C. 154(b) by 870 days.

(21) Appl. No.: 16/981,270

(22) PCT Filed: Sep. 19, 2019

(86) PCT No.: PCT/CN2019/106788
§ 371 (c)(1),
(2) Date: Sep. 15, 2020

(87) PCT Pub. No.: WO2020/057616
PCT Pub. Date: Mar. 26, 2020

(65) Prior Publication Data
US 2021/0052412 A1    Feb. 25, 2021

(30) Foreign Application Priority Data

Sep. 19, 2018 (CN) .......... 201811093874.0

(51) Int. Cl.
*A61F 5/055* (2006.01)
*A61B 5/00* (2006.01)
*G10L 15/18* (2013.01)
*G10L 15/22* (2006.01)
*H04R 1/08* (2006.01)
*H04R 1/10* (2006.01)

(52) U.S. Cl.
CPC .............. *A61F 5/055* (2013.01); *A61B 5/746* (2013.01); *G10L 15/1822* (2013.01); *G10L 15/22* (2013.01); *G10L 2015/223* (2013.01); *H04R 1/08* (2013.01); *H04R 1/1008* (2013.01); *H04R 2460/13* (2013.01)

(58) Field of Classification Search
CPC .. A61F 5/048; A61F 5/05; A61F 5/055; A61F 5/05816; A61F 5/05883; A61F 5/05891; A61F 5/32; A61F 5/34; A61F 5/3707; A61B 7/46; G10L 15/1822; G10L 15/22; H04R 2460/13
USPC .......................................................... 602/16
See application file for complete search history.

(56) References Cited

U.S. PATENT DOCUMENTS

| | | | |
|---|---|---|---|
| 9,913,746 B2 * | 3/2018 | Martin | ..................... A61F 5/055 |
| 2009/0031846 A1 * | 2/2009 | Caiazzo et al. | ........ B62M 25/04 |
| | | | 74/501.6 |

(Continued)

FOREIGN PATENT DOCUMENTS

| | | | | |
|---|---|---|---|---|
| GB | 2505487 A | * | 3/2014 | ............. A61F 5/055 |
| JP | 2000213068 A | * | 8/2000 | |

*Primary Examiner* — Ophelia A Hawthorne
*Assistant Examiner* — Michael Milo
(74) *Attorney, Agent, or Firm* — David & Raymond Patent Firm; Raymond Y Chan

(57) ABSTRACT

An auxiliary support apparatus includes a bearing member and a wear member, wherein the bearing member is used to support the user's head, the wear member includes a wear body extended from the bearing member downwardly while the bearing member is adjustably connected to the wear body.

9 Claims, 24 Drawing Sheets

(56) References Cited

U.S. PATENT DOCUMENTS

2013/0060179 A1* 3/2013 Modglin .................. A61F 5/01
                                                        602/18
2018/0140455 A1* 5/2018 Chao ....................... A61F 5/055

* cited by examiner

AUXILIARY SUPPORT APPARATUS AND APPLICATION THEREOF

BACKGROUND OF THE PRESENT INVENTION

Field of Invention

The present invention relates to the field of head and neck wear, and more particularly to an auxiliary support apparatus and application thereof.

Description of Related Arts

With the liberation of productivity, more and more works can be done simply by operating a computer while sitting in front of the computer. Office workers in office buildings almost maintain sitting postures to complete the work in front of office tables all day long. However, such seemingly relaxing work content actually affects human health or brings certain hidden health risks.

While working at desks or on a computer for long time, one's cervical vertebrae is compressed subjected to a long-term fixed posture, so that the cervical vertebrae is degenerated and causes various discomfort symptoms, such as neck muscle aches and even stiff and sore for the shoulder and the back muscles. If the symptoms are not treated in time, they will continue to deteriorate, and even the lesion of the entire cervical vertebra nerve will be caused.

Cervical collar/brace is a kind of common protective cervical gears for treating cervical spondylosis, which is capable of supporting the head on the torso to reduce and relieve pressure of the head on the cervical vertebra, so as to alleviate the compression to the cervical vertebra.

The cervical neck brace or collar mainly comprises two parts, including a wear member for being worn to the torso, and a supporting member which is configured for supporting the head and is supported by the wear member, so as for supporting the head on the torso to help to reduce the pressure on the cervical vertebra.

Currently, most cervical neck collars or braces in the market have larger sizes since the relationship between the wear member and the supporting portion is unadjustable, that results in larger sizes of the cervical gears in both a height direction and a width direction. On one hand, it is very inconvenient in transportation of the cervical gears due to the cervical gears occupy a large space, and thus it is hard to reduce its logistics cost. On the other hand, it is difficult for a user of the cervical gear to fit the cervical gear at a comfortable wearing angle due to the unadjustable relationship between the wear member and the supporting portion.

Furthermore, the conventional cervical gear needs to wrap neck of user during use, which results in stuffy and airtight feeling of the user's neck during long-term wearing, especially in a hot summer.

SUMMARY OF THE PRESENT INVENTION

An objective of the present invention is to provide an auxiliary support apparatus and application thereof, wherein the auxiliary support apparatus can assist a user's neck to support the user's head over the user's torso while the auxiliary support apparatus can be adjusted.

Another objective of the present invention is to provide an auxiliary support apparatus and application thereof, wherein the auxiliary support apparatus enables a user to change the position of the user's head during applying the auxiliary support apparatus, such as lowering his/her head. Meanwhile, the head adjusted can be still supported, so as to adapt with different usage environments.

Another objective of the present invention is to provide an auxiliary support apparatus and application thereof, wherein the auxiliary support apparatus can prevent a user from over lowering his head such as overly looking down or heading down.

Another objective of the present invention is to provide an auxiliary support apparatus and application thereof, wherein the auxiliary support apparatus can be adjusted downwardly to a position that can be fixed.

Another objective of the present invention is to provide an auxiliary support apparatus and application thereof, wherein the auxiliary support apparatus can be adjusted upwardly to a position that can be fixed.

Another objective of the present invention is to provide an auxiliary support apparatus and application thereof, wherein the lowerly adjusted auxiliary support apparatus significantly reduces a size of the entire auxiliary support apparatus.

Another objective of the present invention is to provide an auxiliary support apparatus and application thereof, wherein the lowerly adjusted auxiliary support apparatus renders the size of the entire auxiliary support apparatus to be reduced to facilitate the transportation and the carry of the auxiliary support apparatus.

Another objective of the present invention is to provide an auxiliary support apparatus and application thereof, wherein the auxiliary support apparatus can be adjusted in a height direction.

Another objective of the present invention is to provide an auxiliary support apparatus and application thereof, wherein the auxiliary support apparatus can be adjusted in a width direction.

Another objective of the present invention is to provide an auxiliary support apparatus and application thereof, wherein the auxiliary support apparatus can accommodate various head and neck curvatures of different users.

Another objective of the present invention is to provide an auxiliary support apparatus and application thereof, wherein the auxiliary support apparatus can accommodate different sizes of heads.

Another objective of the present invention is to provide an auxiliary support apparatus and application thereof, wherein the auxiliary support apparatus can accommodate necks having different lengths.

Another objective of the present invention is to provide an auxiliary support apparatus and application thereof, wherein the auxiliary support apparatus has a supporting state and an unsupporting state, wherein the auxiliary support apparatus can be switched between the supporting state and the unsupporting state, and during the unsupporting state, the auxiliary support apparatus can be adjusted to accommodate different usage environments.

Another objective of the present invention is to provide an auxiliary support apparatus and application thereof, wherein the auxiliary support apparatus has a wear passage, wherein a size of the wear passage can be adjusted.

Another objective of the present invention is to provide an auxiliary support apparatus and application thereof, wherein the auxiliary support apparatus can be attached to a jawbone profile of a head and a supporting height thereof can be adjusted for the head so as to support the jawbone at an appropriate angle.

Another objective of the present invention is to provide an auxiliary support apparatus and application thereof, wherein the auxiliary support apparatus is simple in structure, easy to be manufactured and popularized for use.

According to an aspect of the invention, an auxiliary support apparatus is provided, which comprises:

a bearing member configured for supporting a head of a user; and a wear member comprising a wear body, wherein the wear body is downwardly extended from the bearing member while the bearing member is adjustably connected to the wear body.

According to one embodiment of the present invention, the wear member further comprises an auxiliary wear support, wherein the auxiliary support apparatus has a wear passage, wherein the wear member and the auxiliary wear support surroundingly define the wear passage.

According to one embodiment of the present invention, the bearing member and the wear body form a supporting angle defined therebetween, wherein the supporting angle can be fixed.

According to one embodiment of the present invention, the bearing member is connected to the wear body in such manner that the including angel defined between the bearing member and the wear body is expandable.

According to one embodiment of the present invention, the bearing member is connected to the wear body in such a manner that the including angel defined between the bearing member and the wear body is retractable.

According to one embodiment of the present invention, the bearing member is connected to the wear body in such a manner that the bearing member is adjustable downwardly in relative to the wear body to a position that the bearing member is fixedly connected with the wear body.

According to one embodiment of the present invention, the supporting angle is not less than 45 degrees.

According to one embodiment of the present invention, the auxiliary support apparatus has a supporting state and an unsupporting state, wherein in the supporting state, the support portion is supported by the wear body, wherein in the unsupporting state, the bearing member can be arbitrarily rotated forwards or backwards and its rotated position is not fixedly connected to the wear body, wherein the auxiliary support apparatus can be operatively switched from the supporting state to the unsupporting state by a single action.

According to one embodiment of the present invention, the auxiliary support apparatus further comprises an adjustment portion, wherein the adjustment unit is positioned at a connection position between the bearing member and the wear body, wherein the bearing member is rotatably connected to the wear body by the adjustment unit.

According to one embodiment of the present invention, the adjustment unit comprises a gear rotating shaft and a control lever and has a through hole, wherein the gear rotating shaft is adapted with the through hole, wherein the control lever has a blocking state and an unblocking state, wherein in the blocking state, one end of the control lever is supported by the gear rotating shaft to prevent the gear rotating shaft from moving towards an opposite direction of the current rotation direction, wherein in the non-blocking state, the gear rotating shaft is arbitrarily rotatable with respect to the through hole forwards or backwards, wherein the control lever is operatively switched between the blocking state and the non-blocking state, wherein the gear rotating shaft is provided to the bearing member and the through hole is formed in the wear body, or that the gear rotating shaft is provided to the wear body and the through hole is formed in the bearing member.

According to one embodiment of the present invention, the width of the wear body is adjustable.

According to one embodiment of the present invention, the wear body comprises a first support arm and a second support arm, wherein the first support arm, the second support arm and the bearing member form a triangular support structure, wherein an included angle is defined between the first support arm and the second support arm, wherein the included angle is adjustable.

According to one embodiment of the present invention, the included angle is provided in such a manner that the positions of the first support arm and the second support arm are respectively fixable after adjustment.

According to one embodiment of the present invention, the bearing member is connected to the wear body in such a manner that the width of the bearing member is adjusted in synchronization with the wear body.

According to one embodiment of the present invention, the bearing member comprises a first bearing arm and a second bearing arm, wherein the first bearing arm corresponds to the first support arm and the second bearing arm corresponds to the second support arm, wherein the first bearing arm and the second bearing arm form an including angle, which is adjustable, defined therebetween, wherein after the including angle between the first bearing arm and the second bearing arm is adjusted, the positions of the first bearing arm and the second bearing arm are respectively fixable.

According to one embodiment of the present invention, the width of the wear member is adjustable.

According to another aspect of the present invention, a manufacturing method of an auxiliary support apparatus is provided, which comprises the following steps:

retaining a bearing member to a wear body; and forming a support angle between the bearing member and the wear body in such a manner that the support angle is adjustable in size and is fixable after being adjusted.

According to one embodiment of the present invention, the method further comprises a step of mounting an auxiliary wear support in such a manner that a wear passage is formed between the bearing member and the auxiliary wear support.

According to another aspect of the present invention, an adjusting method of an auxiliary support apparatus is provided, which comprises the following steps:

switching the auxiliary support apparatus from a supporting state to an unsupporting state;

changing a size of a support angle formed and defined between a bearing member and a wear body of the auxiliary support apparatus; and switching the auxiliary support apparatus from the unsupporting state back to the supporting state, so as to fix a size of the support angle after adjustment.

According to one embodiment of the present invention, in the above adjusting method, the support angle between the bearing member and the wear body is reduced by downwardly rotating the bearing member.

DETAILED DESCRIPTION OF THE PREFERRED EMBODIMENT

Figure 1:
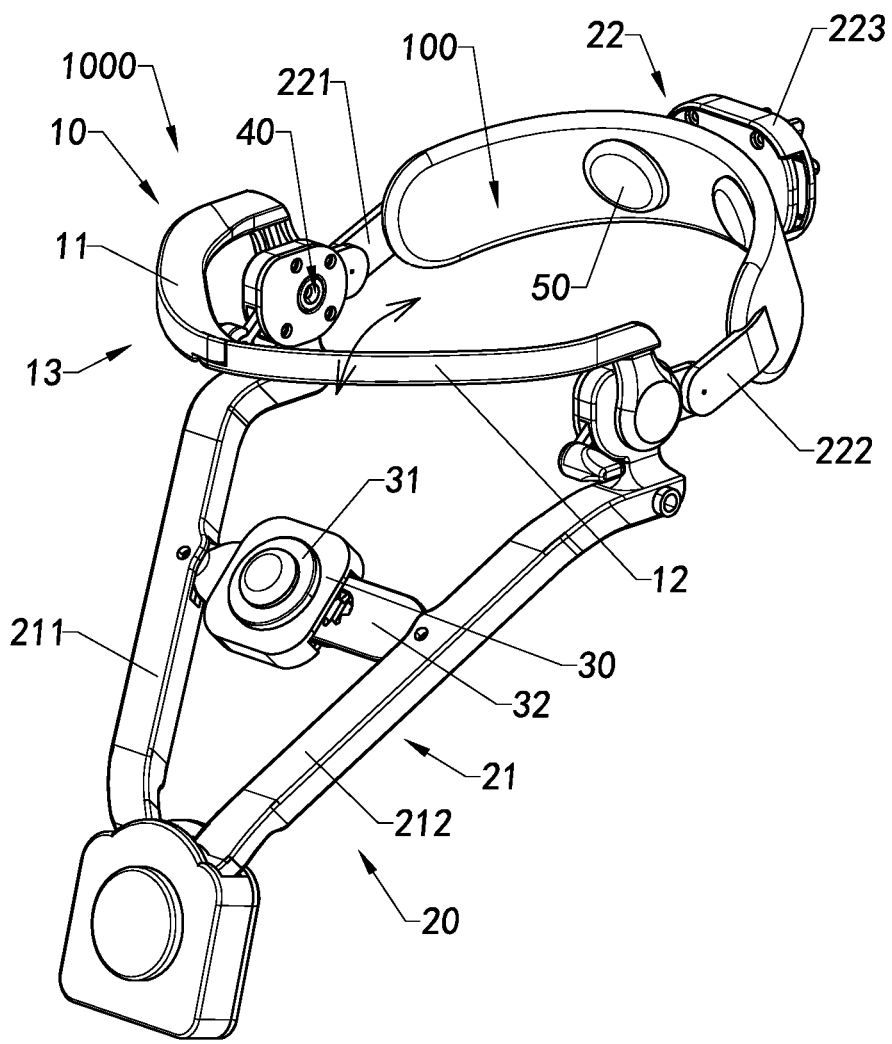
FIG. 1 is a perspective view of an auxiliary support apparatus according to a preferred embodiment of the present invention.

The following description is disclosed to enable any person skilled in the art to make and use the present invention. Preferred embodiments are provided in the following description only as examples and modifications will be apparent to those skilled in the art. The general principles defined in the following description would be applied to other embodiments, alternatives, modifications, equivalents, and applications without departing from the spirit and scope of the present invention.

One skilled in the art will understand that, in the disclosure of the present invention, the orientation and position described by the terms "longitudinal", "transverse", "upper", "lower", "front", "back", "left", "right", "upright", "horizontal", "top", "bottom", "inside", "outside", etc. is based on the orientation or positional relationship shown in the drawings, which is merely for convenience of description of the present invention and is used to simplify the description. The above terms are not to be construed as a device or an element must have specific orientation or the device or the element must be structured and operated in the specific orientation. Hence, the above-mentioned terms can not be construed as limitations to the present invention.

Referring to FIG. 1 to FIG. 3C, an auxiliary support apparatus 1000 according to a preferred embodiment of the present invention is illustrated.

The auxiliary support apparatus 1000 is capable of supporting a user's head over his/her torso portion, so as to reduce the pressure of the head against the neck, so that the auxiliary support apparatus 1000 can play a role of assisting the neck to support the head.

In detail, the auxiliary support apparatus 1000 comprises a bearing member 10 and a wear member 20, wherein the bearing member 10 is connected to the wear member 20, wherein the bearing member 10 is used for supporting the head. The wear member 20 is used for supporting the bearing member 10.

The wear member 20 comprises a wear body 21 and an auxiliary wear support 22, wherein the wear body 21 is extended downwardly from the bearing member 10, wherein the auxiliary wear support 22 and the bearing member 10 define a wear passage 100 therebetween. After the head of a user passes through the wear passage 100, the bearing member 10 is positioned at a front of the head of the user to support the jawbone thereof, and the auxiliary wear support 22 is positioned at a rear of the head of the user and can be supported to the rear of the neck of the user. The auxiliary wear support 22 may be connected to the wear body 21 or may be connected to the bearing member 10.

Furthermore, the auxiliary support apparatus 1000 is designed to be foldable, such that an overall size of the auxiliary support apparatus 1000 in a non-use state can be reduced to facilitate storing and transportation of the auxiliary support apparatus 1000.

In detail, the bearing member 10 is foldably connected to the wear body 21. While the auxiliary support apparatus 1000 is used, the bearing member 10 can be unfolded through the wear body 21 to define a support angle between the bearing member 10 and the wear body 21, so that a height dimension of the auxiliary support apparatus 1000 is increased. While the auxiliary support apparatus 1000 is not needed to be used and needs to be stored, the bearing member 10 can be folded towards the wear body 21 to overlap with the wear body 21, so that the height dimension of the auxiliary support apparatus 1000 is reduced.

The bearing member 10 is rotatably connected to the wear body 21, such that the bearing member 10 can be folded with respect to the wear body 21. Preferably, two ends of the bearing member 10 are respectively connected to the wear body 21 pivotally. One skilled in the art would understand that the two ends of the bearing member 10 can be axially connected to outer sides or inner sides of the wear body 21 respectively.

Furthermore, the bearing member 10 comprises a first bearing arm 11 and a second bearing arm 12, wherein the first bearing arm 11 and the second bearing arm 12 are pivotally connected to define an including angle therebetween, wherein the including angle is an acute angle. The first bearing arm 11 and the second bearing arm 12 are shaped for fittingly attaching to the jawbone of the head respectively, so as to support the head of the user.

The wear body 21 comprises a first support arm 211 and a second support arm 212, wherein the first support arm 211 and the second support arm 212 form a V-shaped structure at a lower portion of the auxiliary support apparatus 1000. It can be understood that the wear body 21 can be supported on the chest or the back of the torso or trunk portion of the user. Preferably, the wear body 21 is supported on the chest of the trunk of the user.

The first support arm 211 corresponds to the first bearing arm 11 and the second support arm 212 corresponds to the second bearing arm 12, wherein the first support arm 211 is foldably connected to the second support arm 212. The first bearing arm 11 is pivotally and foldably connected to the second bearing arm 12. During the first support arm 211 is gradually folded toward the second support arms 212 from an open state thereof, the first bearing arm 11 is driven to be folded toward the second bearing arm 12 from an open state thereof correspondingly. In other words, during the first bearing arm 11 is gradually folded toward the second bearing arm 12 from an open state thereof, the first support arm 211 is driven to be folded toward the second support arms 212 from an open state thereof correspondingly.

A first end of the first bearing arm 11 is pivotally connected to a first end of the second bearing arm 12 and a second end of the first bearing arm 11 is connected to the first support arm 211. In other words, the first end of the second bearing arm 12 is pivotally connected to the first end of the first bearing arm 11 and a second end end of the second bearing arm 12 is connected to the second support arm 212.

One end of the first support arm 211 is connected to the first bearing arm 11 and another end of the first support arm 211 is foldably connected to the second support arm 212. One end of the second support arm 212 is connected to the second bearing arm 12 and the other end of the second support arm 212 is foldably connected to the first support arm 211.

Furthermore, by folding the second bearing arm 12 toward the first bearing arm 11, or folding the first bearing arm toward the second bearing arm 12, accompanying with the folding between the first support arm 211 and the second support arm 212 simultaneously, the size of the auxiliary support apparatus 1000 in a width direction is able to be reduced.

Preferably, the first bearing arm 11 and the second bearing arm 12 of the bearing member 10 are arranged to be symmetrical with each other. The first support arm 211 and the second support arm 212 of the wear body 21 are arranged to be symmetrical with each other.

Furthermore, the auxiliary support apparatus 1000 comprises an adjustment unit 30, wherein the adjustment unit 30 is positioned between the first support arm 211 and the second support arm 212 and is connected to the first support arm 211 and the second support arm 212 respectively. Under the effect of the adjustment unit 30, the folding ranges or the adjusting ranges of the first support arm 211 and the second support arm 212 can be kept to be consistent, so that the folding ranges or the adjusting ranges of the first bearing arm 11 driven by the first support arm 211 and the second bearing arm 12 driven by the second support arm 212 can also be kept to be consistent.

The adjustment unit 30 is capable of restricting a relative displacement between the first support arm 211 and the second support arm 212, and the relative displacement between the first bearing arm 11 and the second bearing arm 12 is restricted by the first support arm 211 and the second support arm 212.

In such a manner, the auxiliary support apparatus 1000 not only can be folded in a height direction or a length direction, but also can be folded in a width direction. While the auxiliary support apparatus 1000 is not in use, the space to be occupied by the auxiliary support apparatus 1000 can be greatly reduced.

The adjustment unit 30 comprises an adjusting mechanism 31 and two adjustment members 32, wherein the adjusting mechanism 31 is connected to the two adjustment members 32 for adjusting the adjustment members 32, so as to change a length of the adjustment unit 30 and the positions of the first support arm 211 and the second support arm 212 respectively connected to two ends of the adjustment unit 30, and to change an included angle defined between the first support arm 211 and the second support arm 212.

It is worth mentioning that the two adjustment members 32 can be adjusted synchronously by the adjusting mechanism 31, such that the first support arm 211 and the second support arm 212 respectively connected to the two adjustment members 32 can be adjusted synchronously. In other words, the first support arm 211 and the second support arm 212 can move an equal distance toward a middle position between the first support arm 211 and the second support arm 212. Or that, each of the first support arm 211 and the second support arm 212 can move a same distance toward each other. Of course, each of the first support arm 211 and the second support arm 212 may also move a same distance toward two opposed directions. In such a manner, the user can conveniently adjust the first support arm 211 and the second support arm 212, and completing an adjustment of the first support arm 211 and the second support arm 212 by a single operation via the adjustment mechanism 31, so as to change the included angle between the first support arm 211 and the second support arm 212 and the including angle defined by the first bearing arm 11 and the second bearing arm 12, so that the auxiliary support apparatus 1000 is able to be adjusted to fit the jawbone portions of the heads of different users.

Furthermore, the adjustment mechanism 31 comprises an operation portion 311 and a control portion 312, wherein the control portion 312 is connected to the two adjustment members 32 respectively. The operation portion 311 is connected to the control portion 312 and can drive the control portion 312 to move. The control portion 312 drives the adjustment members 32 respectively connected to the control portion 312 to move during the movement, so that the first support arm 211 and the second support arm 212 connected to the adjustment members 32 can be adjusted accordingly. In other words, one end of one adjustment member 32 is connected to the first support arm 211; another end of said adjustment member 32 is connected to the control portion 312. One end of the other adjustment member 32 is connected to the support arm 212; another end of said the other adjustment member 32 is connected to the control portion 312.

Figure 3A:
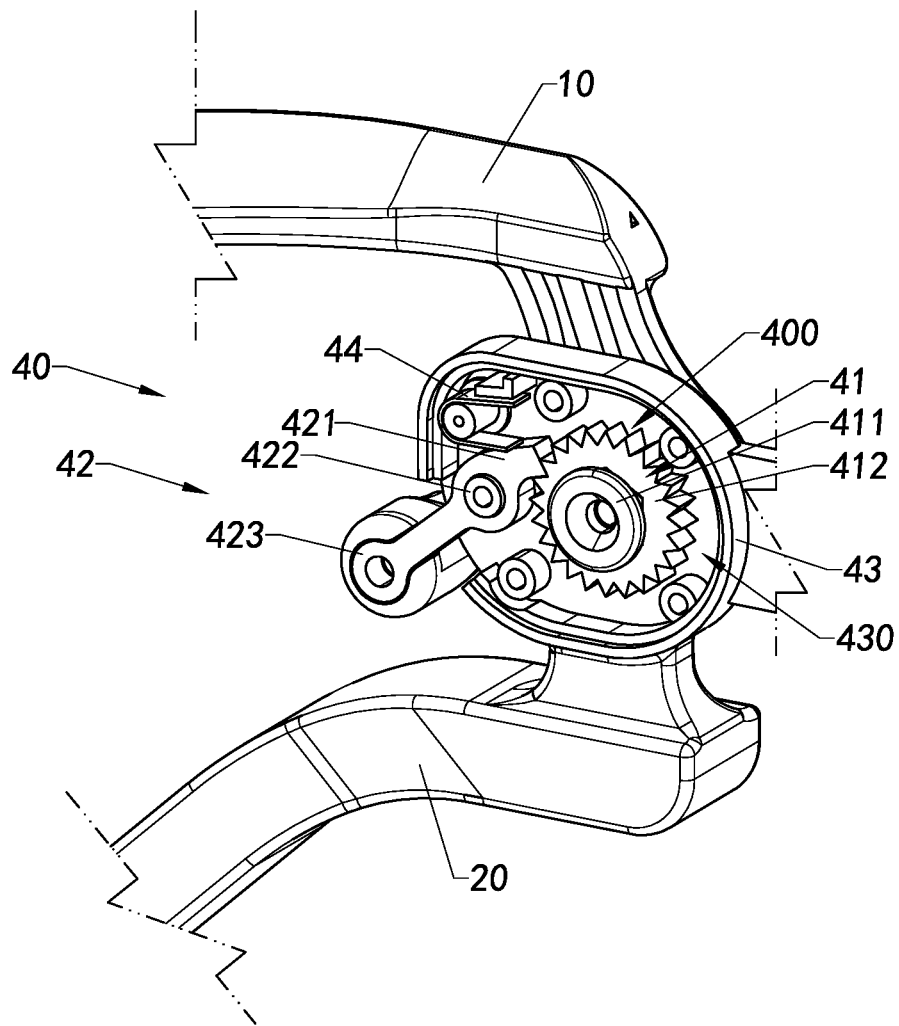
FIG. 3A is a schematic view illustrating a fixed portion of the auxiliary support apparatus according to the above preferred embodiment of the present invention.
Figure 3B:
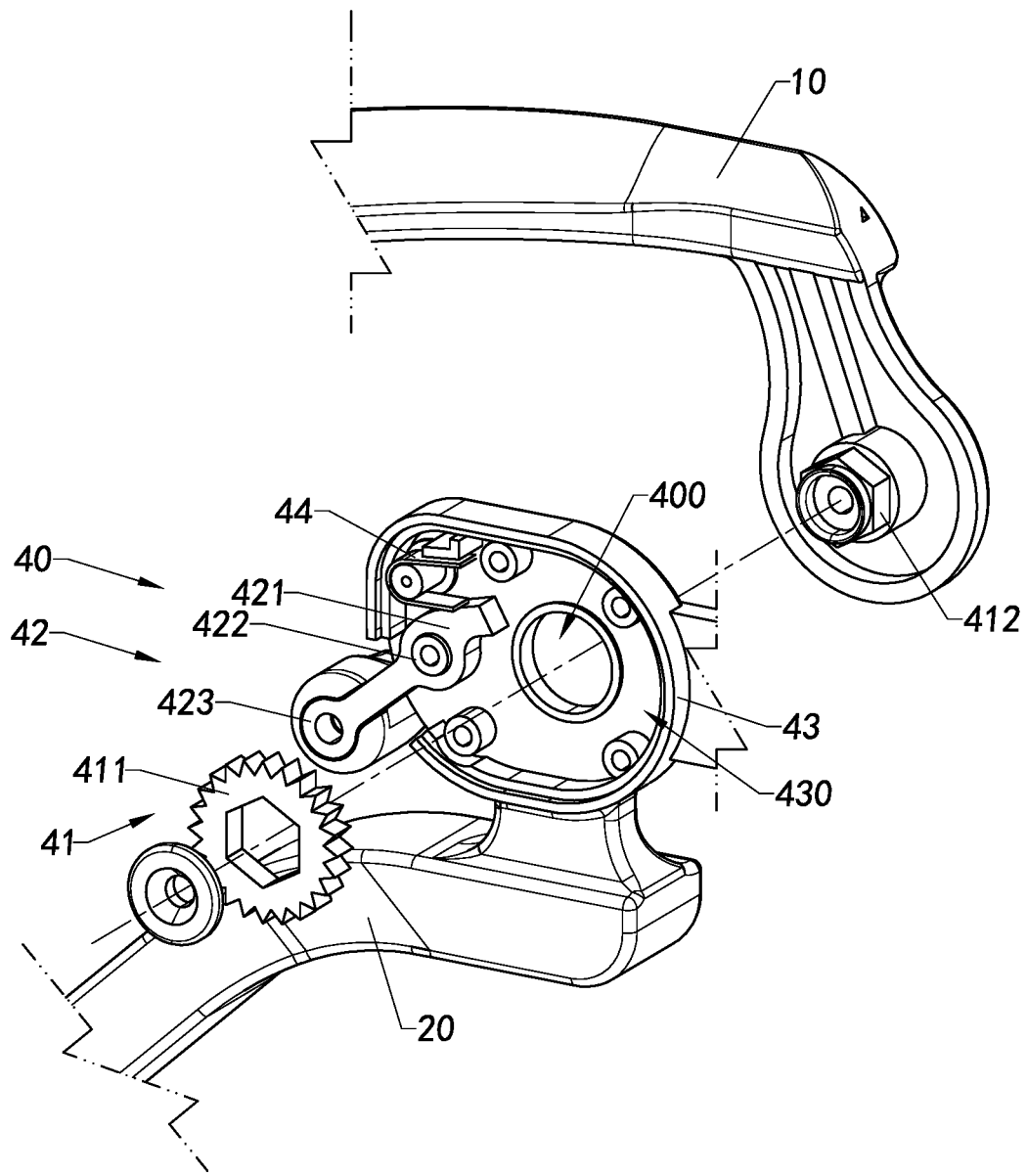
FIG. 3B is another schematic view illustrating a fixed portion of the auxiliary support apparatus according to the above preferred embodiment of the present invention.
Figure 3C:
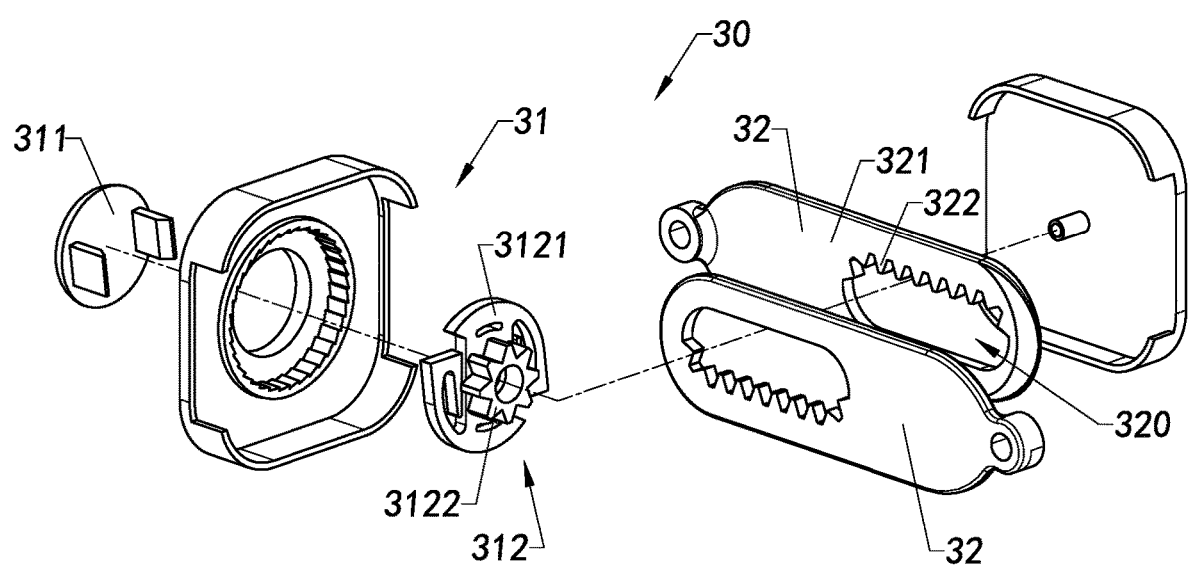
FIG. 3C is a schematic view illustrating an adjustment unit of the auxiliary support apparatus according to the above preferred embodiment of the present invention.

More specifically, referring to FIG. 3C, the control portion 312 comprises a control body 3121 and a control gear 3122, wherein the control gear 3122 is formed around the control body 3121. The control portion 312 has a connection hole. The operation portion 311 is connected to the control body 3121 through the connection hole.

The adjustment member 32 comprises an adjustment body 321 and an adjustment assembly 322, and has an adjustment passage 320, wherein the adjustment passage 320 is formed at one end of the adjustment body 321, wherein the adjustment assembly 322 and the adjustment passage 320 are formed at the same end of the adjustment body 321. The adjustment assembly 322 has a toothed configuration arranged around the adjustment passage 320.

While the adjustment member 32 is mounted to the control portion 312, the adjustment assembly 322 of the adjustment member 32 is engaged to the control gear 3122 of the control portion 312. Two adjustment members 32 are respectively located at two sides of the control portion 312 and are respectively connected to the control portion 312.

Each of the adjustment members 32 has an end portion connected to the control portion 312, wherein the two end portions of the adjustment members 32 are overlapped with each other and engaged with the control gear 3122 of the control portion 312 respectively.

Furthermore, the adjustment member 32 has a length, wherein the adjustment passage 320 is extended along the length of the adjustment member 32. The adjustment assembly 322 is formed around the adjustment passage 320 along the length of the adjustment member 32. While the operation portion 311 controls the control portion 312 to rotate, so as to drive the adjustment member 32 to move, a positional change between the adjustment member 32 and the control portion 312 is a relative position change along the adjustment passage 320. In other words, the position of the control portion 312 at the adjustment passage 320 changes with the operation to the operation portion 311.

In detail, each adjustment member 32 has a connecting end and a free end, wherein the connecting end of one adjustment members 32 is connected to the connecting end of the other adjustment member 32. The free ends of the adjustment members 32 are respectively coupled to the first support arm 211 and the second support arm 212. While the two adjustment members 32 move toward each other, the overlapping area between the two adjustment members 32 becomes more and more, and the control portion 312 approaches toward the free end from the connecting end, so that a total length of the two adjustment members 32 is reduced, so that the included angle between the first support arm 211 and the second support arm 212 is reduced.

It is worth mentioning that the control gear 3122 of the control portion 312 is arranged as a uniform gear. In other words, a distance between every two teeth is the same. The control gears 3122 are engaged with the two adjustment members 32 respectively, so as to drive the adjustment members 32 to rotate or to be driven to rotate by the adjustment members 32, and the two adjustment members 32 respectively move outwardly. In other words, the two adjustment members 32 can be adjusted equidistantly, so that the first support arm 211 and the second support arm can be moved for a same distance or be rotated for a same angle.

While the operating portion 311 is not operated, the position of the control portion 312 and the adjustment member 32 are relatively fixed, so that the first support arm 211 and the second support arm 212 can be fixed at a position to provide a stable supporting ability.

Furthermore, the adjustment assembly 322 can be formed to one side of the position of the adjusting channel 320, and the adjustment assemblies 322 of the adjusting component 32 are respectively formed to two sides of the control portion 312, so that the control gear 3122 can synchronously adjust the two adjustment members 32. For the first support arm 211 and the second support arm 212, the first support arm 211 and the second support arm 212 can be adjusted by the adjustment unit 30 and are fixed to an adjusted position after being adjusted. The first support arm 211 is rotatably connected to the second support arm 212. Optionally, the first support arm 211 is rotatably connected to the second support arm 212 at a range of angles. A stable triangular support is formed among the first support arm 211, the second support arm 212 and the bearing member 10. Furthermore, the first support arm 211 and the second support arm 212 are fixed by the adjustment unit 30, so that the support to the bearing member 10 is more stable on the one hand, and the changed angle between the first support arm 211 and the second support arm 212 is fixed on the other hand.

In such a manner, the dimension of the auxiliary support apparatus 1000 in the width direction can be adjusted. While the auxiliary support apparatus 1000 is not in use, the first support arm 211 of the auxiliary support apparatus 1000 can be folded toward the second support arm 212, so that the first bearing arm 11 and the second bearing arm 12 respectively connected to the first support arm 211 and the second support arm 212 are driven, so as to complete the size reduction of the auxiliary support apparatus 1000 in the width direction.

It is worth mentioning that the first bearing arm 11 of the bearing member 10 is rotatably connected to the second bearing arm 12. The change of the including angle between the first bearing arm 11 and the second bearing arm 12 makes the size of the jawbone of the head of the user that can be supported to the bearing member 10 to change accordingly.

The bearing member 10 can be supported to the wear body 21, and the bearing member 10 can freely rotate with respect to the wear body 21, so as to change the position of the bearing member 10 to support the heads at different positions and have different heights. Furthermore, the bearing member 10 can be supported at a changed position after the position of the bearing member 10 is changed.

According to an alternative embodiment, the adjustment mechanism 31 and the two adjustment members 32 are tubular. One end of one adjustment member 32 is connected to the first support arm 211, wherein the other end of the one adjustment members 32 is sleeved to the adjusting mechanism 31. One end of the other adjustment member 32 is connected to the second support arm 212, and the other end of the other adjustment member 32 is sleeved to the adjusting mechanism 31. While the adjustment mechanism 31 is operated in a rotational manner, the distance between the two adjustment members 32 is adjusted to adjust the included angle between the first support arm 211 and the second support arm. According to different rotation directions, the distance between the two adjustment members 32 is reduced or increased.

In particular, the auxiliary support apparatus 1000 further comprises a fixing unit 40, wherein the fixing unit 40 is formed between the bearing member 10 and the wear body 21 for fixing the bearing member 10 and the wear body 21.

The fixing unit 40 comprises a gear rotating shaft 41 and a lever 42, and has a through hole 400, referring to FIGS. 3A and 3B, wherein the through hole 400 is adapted to the gear rotating shaft 41, wherein the gear rotating shaft 41 is arranged to an end portion of the portion 10. The through hole 400 is formed in one end of the wear body 21. The gear rotating shaft 41 is received in the through hole 400.

While the bearing member 10 is pivotally rotated with respect to the wear body 21, the gear rotating shaft 41 is rotated with respect to the position of the through hole 400. The gear rotating shaft 41 comprises a shaft main body 412 and a wheel gear 411, wherein the wheel gear 411 is formed outside the shaft main body 412. The lever 42 is supported to the wheel gear 411, so that the wheel gear 411 can only be rotated in one direction under the control of the lever 42. The gear teeth of the wheel gear 411 determine the rotated angle of the bearing member 10 and the wear body 21 with respect to each other after each adjustment. The smaller the pitch distance between the teeth of the wheel gear 411, the higher the accuracy of the angle adjustment between the bearing member 10 and the wear body 21. Alternatively, the wheel gear 411 is detachably connected to the shaft main body 412, so as to accommodate different wheel gears 411 with different tooth pitches for different needs.

According to the preferred embodiment, the bearing member 10 is able to move in a direction away from the wear body 21. In particular, the lever 42 is coupled to the wheel gear 411, and the lever 42 provides a supporting force to the wheel gear 411 of the gear rotating shaft 41. The direction of the supporting force determines the rotation direction of the gear rotating shaft 41. In other words, the lever 42 prevents the gear rotating shaft 41 from rotating in an opposite direction. For the bearing member 10 and the wear body 21, the user can lift the bearing member 10 upwards. While the user stops the action, the bearing member 10 can be held at a fixed angle due to the lever 42 prevents the downward resetting movement of the bearing member 10.

The lever 42 enables the gear rotating shaft 41 to rotate in a fixed direction, such as a clockwise direction or a counterclockwise direction, in other words, a forward direction or a backward direction. The gear rotating shaft 41 is movable forwardly in the direction of the force provide by the lever 42. The reason is that once the gear rotating shaft 41 moves in the direction opposite to the force provide by the lever 42, the wheel gear 411 will be directly locked, so that the gear rotating shaft 41 cannot continue to move in the direction opposite to the force provide by the lever 42.

The fixing unit 40 further comprises a housing 43, wherein the gear rotating shaft 41 is received in the housing 43. One end of the lever 42 is supported to the gear rotating shaft 41 while being received in the housing 43. The other end of the lever 42 is exposed outside the housing 43. At least a portion of the housing 43 can be integrally formed to the wear body 21.

It is worth mentioning that the lever 42 is movable. While the bearing member 10 is lifted to a certain height, and the user wants to take off the auxiliary support apparatus 1000 from the head and neck, the lever 42 can be operated to move the end of the lever 42 supported to the gear rotating shaft 41 away from the gear rotating shaft 41, so that the bearing member 10 moves downward under its own weight, and the gear rotating shaft 41 also moves in an opposite direction because the blocking of the lever 42 is removed, so that the bearing member 10 can automatically fall to a position under the effect of gravity, so as to facilitate the subsequent wearing on and taking off of the auxiliary support apparatus 1000.

More particularly, the fixing unit 40 further comprises an elastic member 44, wherein the elastic member 44 is connected to the housing 43. The lever 42 is rotatably connected to the housing 43. The lever 42 has a blocking state and a non-blocking state. In the blocking state, the elastic member 44 restricts the movement of the lever 42, so that the lever 42 is supported to the gear rotating shaft 41, and thus the gear rotating shaft 41 can only move in one direction. The lever 42 is operatively switched from the blocking state to the non-blocking state. In the non-blocking state, the lever 42 is disengaged from the gear rotating shaft 41 to enable the gear rotating shaft 41 to be rotated forward or backward at random. Furthermore, the lever 42 is automatically switched from the non-blocking state to the blocking state. In detail, in the blocking state, the lever 42 is driven to move away from the gear rotating shaft 41 while pressing the elastic member 44 to deform. Once the driving force to the lever 42 disappears or is weakened to less than the elastic force of the elastic member, the elastic member 44 automatically drives the lever 42 to return to the blocking state.

Furthermore, the lever 42 further comprises a stopper portion 421, a support 422 and a pressing portion 423. The stopper portion 421 is movably engaged with the wheel gear 411. The pressing portion 423 is extended outside the housing 43 through the support 422. It is worth mentioning that the pressing portion 423 and the stopper portion 421 are made integrally in one piece. Further, the pressing portion 423 and the stopper portion 421 forms a levering element around the support 422. When the pressing portion 423 is pressed, the stopper portion 421 moves upwardly away from the wheel gear 412, such that the bearing member 10 is able to move in a direction approaching the wear body 21. When the pressing of the pressing portion 423 is released, the elastic member 44 applies a pressure against the stopper portion 421 so as to engage the stopper portion 423 with the wheel gear 412, such that the bearing member 10 is able to move away from the wear body 21. The bearing member 10 is blocked to be moved toward the wear body 21.

The elastic member 44 can be a spring piece or a torsion spring.

While a user uses the auxiliary support apparatus 1000, the distance between the bearing member 10 and the wear body 21 can be adjusted directly in one direction and then the bearing member 10 is directly fixed to that position to the wear body 21 after the adjustment. In other words, the bearing member 10 can be moved in a direction with respect to the wear body 21, such as clockwise, but cannot move in an opposite direction, such as counterclockwise, so that after a positional relationship of the bearing member 10 and the wear body 21 is adjusted, the bearing member 10 can be directly fixed to the wear body 21.

In other words, the auxiliary support apparatus 1000 can not only be connected to the wear body 21 while the supporting angle can be adjusted, but also be fixed to the wear body 21 while the supporting angle is fixed.

It can be understood that the position of each component of the fixing unit 40 is not limit to the above mentioned position. The positions of the gear rotating shaft 41 and the through hole 400 can be interchanged. In other words, the gear rotating shaft 41 is formed at the wear body 21 and the through hole 400 is formed in the bearing member 10, so long as the final effect that the bearing member 10 can be rotated with respect to the wear body 21 and can be fixed to the position after being rotated. It can be understood that the number of the fixing unit 40 is not limited to one. At the junction of the bearing member 10 and the wear body 21, the number of the fixing units 40 can be two, and the direction of the gear rotating shaft 41 limited by the lever 42 is different, so that the bearing member 10 can be rotated in the counterclockwise direction and the clockwise direction and can be fixed in position after being rotated. The number of the lever 42 is not limited to one. In one fixing unit 40, the number of the lever 42 can be two, and the direction of the gear rotating shaft 41 limited by the levers 42 can be different, so that the bearing member 10 can be rotated in the counterclockwise direction and the clockwise direction and can be fixed in position after being rotated.

The auxiliary wear support 22 can be connected to two ends of the bearing member 10 or the wear body 21. While the included angle between the first support arm 211 and the second support arm 212 of the wear body 21 is changed, the size of the wear passage 100 formed between the auxiliary wear support 22 and the bearing member 10 is also changed accordingly.

The auxiliary wear support 22 makes the support between the bearing member 10 and the wear body 21 more stable.

In particular, the auxiliary wear support 22 is connected to the bearing member 10 with an adjustable length. According to some embodiments of the present invention, the auxiliary wear support 22 is detachably connected to the bearing member 10. In other words, the auxiliary wear support 22 can be suitably selected by the user as required. The auxiliary wear support 22 comprises a first locking connector 221, a second locking connector 222 and a locking button 223, wherein the first locking connector 221 and the second locking connector 222 are respectively connected to two ends of the bearing member 10 or to two ends of the wear body 21. In other words, the first locking connector 221 and the second locking connector 222 can be connected to the bearing member 10 or the wear body 21 or a joint between the bearing member 10 and the wear body 21.

At least a portion of the first locking connector 221 is overlapped to at least a portion of the second locking connector 222. The first locking connector 221 and the second locking connector 222 respectively have a first locking cavity 2211 and a second locking cavity 2221, wherein the first locking cavity 2211 and the second locking cavity 2221 are respectively formed to free ends of the first locking connector 221 and the second locking connector 222. The more overlapping portions the first locking connector 221 and the second locking connector 222 have, the more overlapping regions the first locking cavity 2211 and the second locking cavity 2221 have, the shorter the entire auxiliary wear support 22 is. The locking button 223 can be rotatably connected to the first locking connector 221 and the second locking connector 222, wherein the locking button 223 is received in the overlapping region of the first locking cavity 2211 and the second locking cavity 2221. The locking button 223 is capable of lock relative movement between the first locking connector 221 and the second locking connector 222.

The auxiliary wear support 22 further comprises a first locking tooth and a second locking tooth, wherein the first locking tooth is arranged to the first locking cavity 2211, and the second locking tooth is arranged to the second locking cavity 2221 to increase the stability of the connection between the locking button 223 and the first locking tooth, and increase the stability of the connection between the locking button 223 and the second locking tooth, so as to avoid unnecessary relative movement between the first locking connector 221 and the second locking connector 222.

It is worth mentioning that the lengths of the first locking connector 221 and the second locking connector 222 can be adjusted simultaneously, so as to bring the neck into an equilibrium state.

Alternatively, the first locking tooth is formed to one side of the position of the first locking cavity 2211, and the second locking tooth is formed on one side of the position of the second locking cavity 2221, so that both sides of the locking button 223 are provided with the locking teeth.

According to some embodiments of the present invention, the auxiliary wear support 22 is an elastic band. According to some embodiments of the present invention, the auxiliary wear support 22 is designed as hook and loop fasteners (Velcro). According to some embodiments of the present invention, the auxiliary wear support 22 is a buckle structure.

It is more worth mentioning that the bearing member 10 can be reset by a single operation.

The bearing member 10 can be supported at a fixed angle by the wear body 21 to support the head to the auxiliary support apparatus 1000. But during the wearing and taking off of the auxiliary support apparatus 1000, the wear passage 100 defined by the bearing member 10 and the auxiliary wear support 22 can be inconvenient for the user to wear and take off due to the bearing member 10 forms a rigid frame near the user's head and makes it difficult to directly access the head from the wear passage 100 defined by the bearing member 10 and the auxiliary wear support 22. The user may need to take off the auxiliary support apparatus 1000 by enlarging the wear passage 100.

The auxiliary support apparatus 1000 has a supporting state and an unsupporting state. In the supporting state, the head can be supported to the bearing member 10. In the unsupporting state, the bearing member 10 cannot be support the head. The bearing member 10 can be reseted to the unsupporting state by a single operation, so that the bearing member moves downward away from the head, so that the wear passage 100 is enlarged and the head can leave the auxiliary support apparatus 1000 conveniently.

In detail, in the supporting state, the lever 42 of the fixing unit 40 is supported to the gear rotating shaft 41 such that the gear rotating shaft 41 can rotate in one direction and cannot rotate in the opposite direction, so that the bearing member 10 can be supported to the wear body 21. In the unsupporting state, the lever 42 is not supported to the gear rotating shaft 41, and the gear rotating shaft 41 can be arbitrarily rotated clockwise or counterclockwise. By controlling the position of the lever 42, the support portion 10 can be controlled to switch between the supporting state and the unsupporting state.

It can be understood that, according to this preferred embodiment, the bearing member 10 can be adjusted from an A position to a B position, where the B position is higher than the A position. Once the user finds that the B position is too high and needs to be lowered, adjust the bearing member 10 toward the A position. The user can control the lever 42 to be switched from the blocking state to the non-blocking state, so as to enable the bearing member 10 to move toward the A position. After the user releases the lever 42, the lever 42 automatically switches from the non-blocking state back to the blocking state, so that the bearing member 10 cannot continue to move toward the A position. In such manner, the adjustment to the relative position between the bearing member 10 and the wear body 21 is accomplished.

According to this preferred embodiment of the present invention, in the supporting state, the bearing member 10 can be adjusted in one direction. It will be understood that the direction does not limit the invention. The direction in which the support portion 10 is adjusted may also be changed as long as the direction of the force of the lever 42 with respect to the gear rotating shaft 41 is changed.

In other words, the bearing member 10 is rotatably supported to the wear member 20 in a fixed orientation in the supporting state, and in the unsupporting state, the bearing member 10 is connected to the wear member 20 in such a manner that the bearing member 10 can be rotated forwardly or rearwardly as required.

Furthermore, the bearing member 10 comprises a bearing body 13 and two first support legs 14, wherein the bearing body 13 comprises the first bearing arm 11 and the second bearing arm 12 each having one end pivotally connected with each other to define the including angle therebetween, wherein the first support legs 14 respectively connected to two ends of the bearing body 13. The first support leg 14 is disposed to extend downward from the bearing body 13 such that the bearing body 13 is supported to the first support leg 14.

The wear member 20 comprises the wear body 21 and two second support legs 23, wherein the wear body 21 comprises the first support arm 211 and the second support arm 212 each having one end foldably connected with each other, wherein the two second support legs 23 are respectively connected to two ends of the wear body 21. Each of the second support legs 23 is arranged to extend upward from the wear body 21.

The fixing unit 40 is arrange at a joint of the bearing member 10 and the wear body 21, and the bearing member 10 is rotatably connected to the wear body 21 of the wear member 20 via the fixing unit 40. Furthermore, the bearing member 10 is fixed to the wear body 21 via the fixing unit 40 in such a manner that the supporting angle defined between the bearing member 10 and the wear member 20 is adjustable and the adjusted bearing member 10 after adjustment can be fixedly supported to the wear body 21.

The first support legs 14 of the bearing member 10 are arranged corresponding to the second support legs 23 of the wear body 21 respectively. Due to the presence and arrangement of the first support legs 14 and the second support legs 23, in the vertical direction, a height position of the bearing member 10 is higher than a height position of the wear body 21 and higher than a height position of the support member 22, so that the bearing member 10 can be more conveniently fitted to a head chin curvature during the adjustment of the auxiliary support apparatus 1000 while the auxiliary wear support 22 can be positioned at a lower position of the neck.

Optionally, a total height of the first support legs 14 and the second support legs 23 matches a neck height of the user, so that the head can be naturally supported by the auxiliary support apparatus 1000 while the neck is kept and retained in a relaxed state.

Optionally, the end of the wear body 21 can be configured to fit over the user's shoulder curve to support the bearing member 10 to the user's shoulder.

According to other embodiments of the present invention, the bearing member 10 and the auxiliary wear support 22 are respectively connected to the fixing unit 40. The ends of the bearing member 10 fitted to the lower jaw portion of the user's head are almost at the same height with the ends of the auxiliary wear support 22 respectively. In other words, the first support legs 14 are arranged to fit to the lower jaw curvature of the user's head.

Furthermore, the auxiliary support apparatus 1000 comprises at least a functional unit 50, wherein the functional unit 50 is arranged at an inner side of the auxiliary wear support 22, so that while the auxiliary support apparatus 1000 is worn to the neck of the user, the auxiliary support apparatus 1000 is placed behind the neck of the user. The functional unit 50 can be embodied as a pulse module which is capable of generating pulses to massage the neck muscles. The functional unit 50 can also be embodied as a heating module capable of producing heat to provide a hot compress effect. The functional module can also be embodied as a magnetic therapy module capable of generating a magnetic field for applying magnetic therapy to the neck.

Preferably, the functional unit 50 is a disc configuration, and the functional unit 50 has a certain curvature to fit and match the curve of the neck.

Furthermore, the functional unit 50 is connected to the auxiliary wear support 22 in such a manner that the functional unit 50 can be moved reciprocatingly, so as to provide caring treatment for various portions of the neck during the usage. Preferably, the first support arm 211 and the second support arm 212 of the wear body 21 are shaped and arranged to fit on a human shoulder curve for more comfortable fitting during usage. Preferably, the first bearing arm 11 and the second bearing arm 12 of the bearing member 10 are shaped and arranged to fit to the human lower jaw curve for more comfortable fitting during usage.

According to some embodiments of the present invention, the bearing member 10 is arranged to have certain elasticity such that when the included angle between the first support arm 211 and the second support arm 212 is reduced, the wear passage 100 defined by the bearing member 10 and the auxiliary wear support 22 is also reduced.

Preferably, the first bearing arm 11 and the second bearing arm 12 of the bearing member 10 are rotatably connected with each other. In more detail, the first bearing arm 11 and the second bearing arm 12 of the bearing member 10 are pivotally connected with each other in such a manner that the first bearing arm 11 and the second bearing arm 12 can be rotated about each other on the plane defined by the first bearing arm 11 and the bearing arm 12, so that the size of the wear passage 100 is changed while the whole bearing member 10 is retained in a stable structure. In other words, the first bearing arm 11 of the bearing member 10 is pivotally connected to the second bearing arm 12 about an axial along a perpendicular direction.

Figure 4:
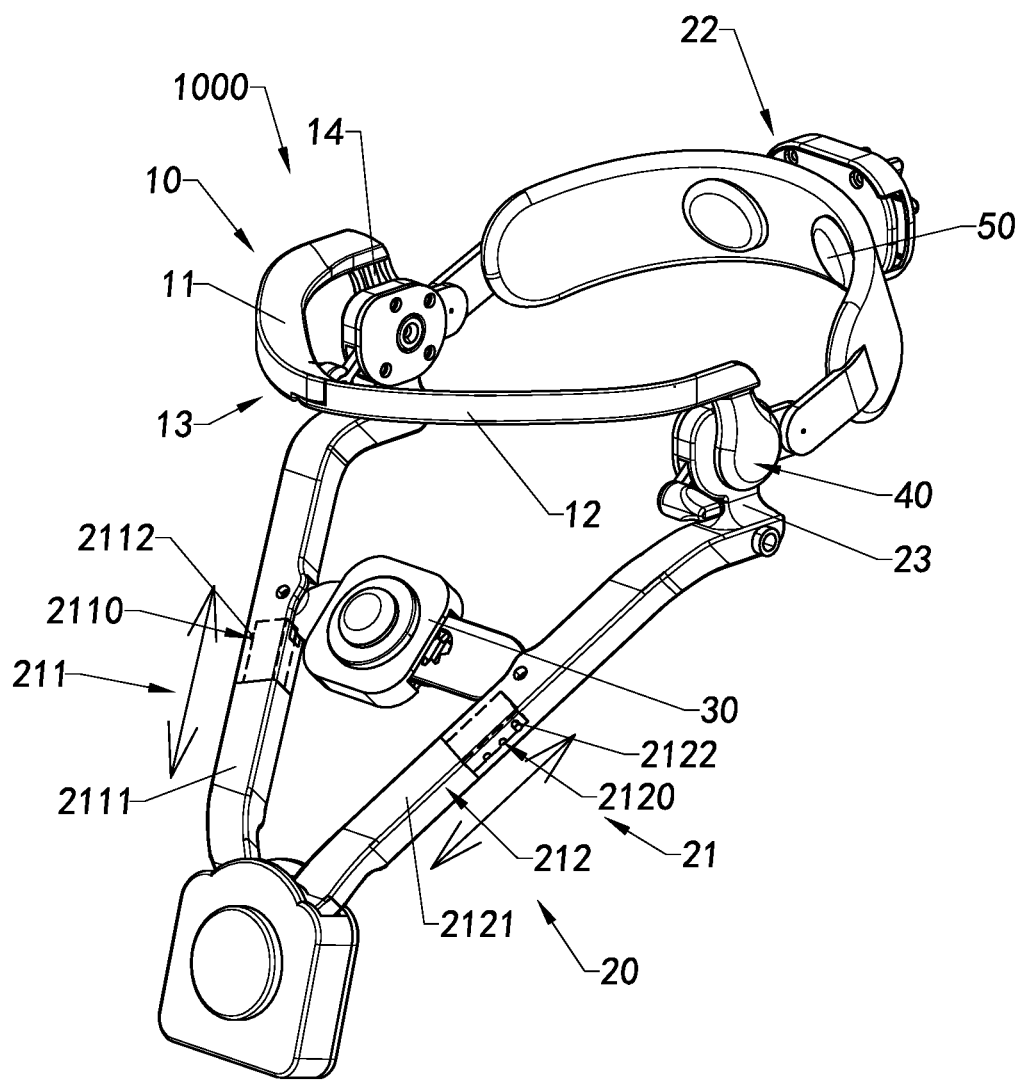
FIG. 4 is a perspective view illustrating the auxiliary support apparatus according to the above preferred embodiment of the present invention.

Referring to FIG. 4, an alternative embodiment of the auxiliary wearing device 1000 according to the above preferred embodiment is illustrated. The difference between the two embodiments is the first support arm 211 and the second support arm 212 of the wear body 21. According to this alternative embodiment, the height of the wear body 21 can also be adjusted. On one hand, the size of the auxiliary support apparatus 1000 in the height direction is able to be reduced. On the other hand, the auxiliary support apparatus 1000 is facilitated for being adjusted in the height direction, so as to facilitate the user to adjust the position of the auxiliary support apparatus 1000 being supported.

In detail, the first support arm 211 comprises a plurality of first supporting bars 2111, wherein for two adjacent first supporting bars 2111, one of the first supporting bars 2111 can be partially received in the other one of the first supporting bars 2111. The length of the entire first support arm 211 is shortened by shortening the distance between the two adjacent first supporting bars 2111.

Furthermore, while a total length of the first support arm 211 is arranged to be extensible and retractable, the length after change can be fixed to ensure the first support arm 211 supporting the bearing member 10 within a fixed length in a changeable manner.

The first support arm 211 further comprises a first lock 2112, wherein the first lock 2112 is detachably connected to the two first supporting bars 2111 in such a manner that the two first supporting bars 2111 can be fixed to this adjusted length after the length adjustment. The first supporting bar 2111 has a plurality of first positioning holes 21110 arranged and aligned intervally. While one of the first supporting bars 2111 is partially received in the other one of the first supporting bars 2111, and the first positioning hole 21110 of the first supporting bar 2111 is aligned with the first positioning hole 21110 of the other one of the first supporting bars 2111, the first locking piece 2112 can be inserted into the aligned first positioning holes 21110, so that the positions of the two first supporting bars 2111 are locked and fixed so as to fix the adjusted length thereof.

Correspondingly, for the second support arm 212, the second support arm 212 comprises a plurality of the second supporting bars 2121, and one of the second supporting bars 2121 is partially received to the other one of the second supporting bars 2121. The length of the entire second support arm 212 is shortened by shortening the distance between the two adjacent second supporting bars 2121. Furthermore, the second supporting bar 2121 can be fixed to another adjacent second supporting bar 2121 after the change of length, so that the second support arm 212 provides a rigid and fixed supporting force.

The second support arm 212 further comprises a second lock 2122, wherein the second lock 2122 is detachably connected to the two second supporting bars 2121 in such a manner that the two second supporting bars 2121 can be fixed to this adjusted length after the length adjustment. The second supporting bar 2121 has a plurality of second positioning holes 21210 aligned and arranged intervally. While one of the second supporting bars 2121 is partially and received in the other one of the second supporting bars 2121, and the second positioning hole 21210 of one of the second supporting bars 2121 is aligned with the second positioning hole 21210 of the other one of the second supporting bars 2121, the second locking member 2122 can be inserted into the aligned second positioning holes 21210 for fixing the positions of the second supporting bars 2121, so as to fix the adjusted length after the adjustment.

The wear body 21 is provided to be telescopically extensible and retractable, so that the user can adjust the height of the wear body 21 according to his/her own requirements.

According to other embodiments of the present invention, the first support arm 211 is detachably connected to the second support arm 212. After the first support arm 211 and the second support arm 212 are detached, one of the first supporting bars 2111 of the first support arm 211 is rotatably connected to the other one of the first supporting bars 2111. While rotating one of the first supporting bars 2111, the connection between the first supporting bars 2111 is loosened, so that the distance between the two first supporting bars 2111 is adjustable. While rotating the first supporting bar in the other direction, the connection between the first supporting bars 2111 is tightened, so that the distance between the first supporting bars 2111 is fixed, so that the length adjustment to the first support arm 211 is accomplished.

Correspondingly, after the first support arm 211 and the second support arm 212 are separated with each other, one of the second supporting bars 2121 of the second support arm 212 is rotatably connected to another one of the second supporting bars 2121. While one of the second supporting bars 2121 is rotated in one direction, the connection between the second supporting bars 2121 is loosened, so that the distance between the two second supporting bars 2121 can be adjusted. While the second supporting bars 2121 is rotated in the other direction, the connection between two second supporting bars 2121 are tightened, so that the length adjustment to the second support arms 212 is achieved.

Figure 5:
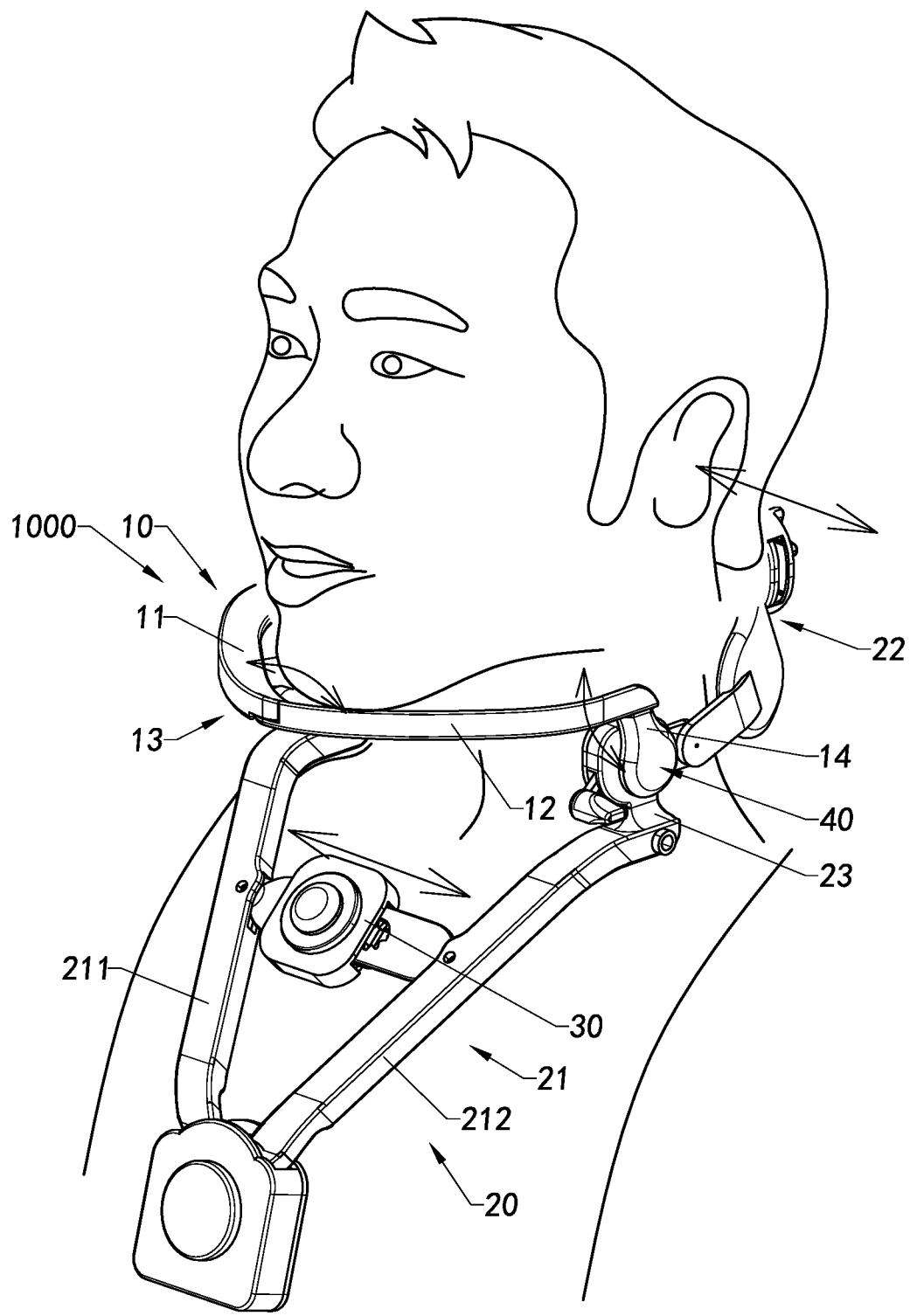
FIG. 5 is a schematic view illustrating an application of the auxiliary support apparatus according to the above preferred embodiment of the present invention.

Referring to FIG. 5, an application schematic view of the auxiliary support apparatus 1000 as shown in FIG. 1 to FIG. 3C is illustrated.

Before the auxiliary support apparatus 1000 is used, the auxiliary support apparatus 1000 is first deployed from a folded state to an open state to form the wear passage 100 for the user to wear. The wear body 21 of the auxiliary support apparatus 1000 is worn on the shoulder of the user, and the user can adjust a width of the auxiliary support apparatus 1000 according to the shoulder width and the head size, so that the wear body 21 can be supported at the shoulder and then lift the bearing member 10 according to the height of the user's head, such that the bearing member 10 can support the head to a suitable and appropriate position.

Furthermore, the user may adjust the including angle between the first bearing arm 11 and the second bearing arm 12 of the bearing member 10 according to the consideration of the wearing comfort performance, so that the first bearing arm 11 and the second bearing arm 12 can be supported in such a manner that the first bearing arm 11 and the second bearing arm 12 are fittingly attached to the jawbone of the head, or that the first bearing arm 11 and the second bearing arm 12 can be supported to the head in such a manner that the user feels more comfortable. Meanwhile, the included angle between the first support arm 211 and the second support arm 212 is also adjusted accordingly.

From another point of view, after the auxiliary support apparatus 1000 is initially worn, the auxiliary support apparatus 1000 mainly has three support points, wherein one is the position of the jawbone of the user's head; another is the shoulder of the user; the third is on the user's trunk. In such a manner, the auxiliary support apparatus 1000 can be stably supported to the user.

In particular, the first bearing arm 11 and the second bearing arm 12 of the bearing member 10 of the auxiliary support apparatus 1000 are respectively supported at the position of the jawbone of a user's head. The second support legs 23 of the wear member 20 of the auxiliary support apparatus 1000 are respectively supported to the user's shoulder. The joint of the first support arm 211 and the second support arm 212 of the wear body 21 of the auxiliary support apparatus 1000 is supported to a user's trunk. The junction between the first support arm 211 and the second support arm 212 is positioned at the lower end of the auxiliary support apparatus 1000. The human body has a certain curve and curvature. When the auxiliary support apparatus 1000 is worn on the chest of the user, the connection between the first support arm 211 and the second support arm 212 is positioned between the left and right ribs of the user. The auxiliary support apparatus 1000 is held in position so as to prevent the auxiliary support apparatus 1000 from swaying during the wearing.

Furthermore, the user can make various adjustments to the auxiliary support apparatus 1000, so that the auxiliary support apparatus 1000 can better support the head of the user.

One adjustment is that the user can adjust a support height of the auxiliary support apparatus 1000. The user can adjust the support height of the head according to his/her own needs or the height of the position of his/her own head. The bearing member 10 is rotatably connected to the wear body 21 of the wear member 20. While the bearing member 10 is located forward to support the head, the larger the including angle between the bearing member 10 and the wear body 21, the higher the position of the joint between the first bearing arm 11 and the second bearing arm 12 of the bearing member 10, so that the head can be supported to a higher height. For example, while the user wants to remain looking up for a long time, the bearing member 10 can be rotated upwards to increase the supporting height of the bearing member 10. For example, while the user wants to maintain an overlooking state for a long time, the bearing member 10 can be rotated downwards to reduce the supporting height of the bearing member 10.

It is worth mentioning that after adjusting the position height of the bearing member 10, the bearing member 10 can be fixed to the adjusted position height by the fixing unit 40. For example, while the user is reading a book or studying, the support height of the bearing member 10 is adjusted first, so that the user is in an overlooking state for convenient reading. In this process, under the supporting effect from the bearing member 10, the user's head will not be allowed to continue to move downward so as to facilitate the user's eye health. Especially for students with a large workload, the auxiliary support apparatus 1000 can prevent myopia effect. It is worth mentioning that the including angle between the bearing member 10 and the wear body 20 of the auxiliary support apparatus 1000 can be defined not less than a predetermined angle to prevent the user from adjusting the auxiliary support apparatus 1000 to an angle smaller than the predetermined angle, that avoids the cervical vertebra from suffering excessive pressure on one hand, and maintains good vision on the other hand. The predetermined angle can be 45 degree or 60 degree or 90 degree, which is merely an example and not a limitation to the predetermined angle.

One adjustment method is that the user can adjust the support width of the auxiliary support apparatus 1000 on the user's shoulder. The user's shoulder is the primary bearing point of the entire auxiliary support apparatus 1000. If the auxiliary support apparatus 1000 is worn on a predetermined portion of the shoulder of the user for a long time, the user himself/herself may feel uncomfortable, and the user may adjust the position to the shoulder from the auxiliary support apparatus 1000 by adjusting the distance between the two second support legs 23 of the wear member 20 of the auxiliary support apparatus 1000. The user can directly manipulate the second support leg 23 of the wear member 20 to change the width of the auxiliary support apparatus 1000. It can b e understood that in the process, the included angle between the first support arm 211 and the second support arms 212 is correspondingly reduced, and the including angle between the first bearing arm 11 and the second bearing arm 12 is also relatively reduced.

In other words, the auxiliary support apparatus 1000 can be adjusted in both the height direction and the width direction. It is worth mentioning that, while the auxiliary support apparatus 1000 is adjusted in the width direction, the width of the auxiliary support apparatus 1000 can be adjusted at a plurality of positions of the auxiliary support apparatus 1000. In other words, while the width of the auxiliary support apparatus 1000 is adjusted, the various portions and positions of the auxiliary support apparatus 1000 are interlocked. For example, while the width of the bearing member 10 is adjusted to make the first bearing arm 11 and the second receiving arm 12 close to each other, the width of the wear body 21 is simultaneously reduced, and the first support arm 211 and the second support arm 212 of the wear body 21 are also close to each other. In other words, while the width of a certain position of the auxiliary support apparatus 1000 is adjusted, other positions of the auxiliary support apparatus 1000 are linkingly and correspondingly adjusted in the width direction simultaneously.

Figure 6A:
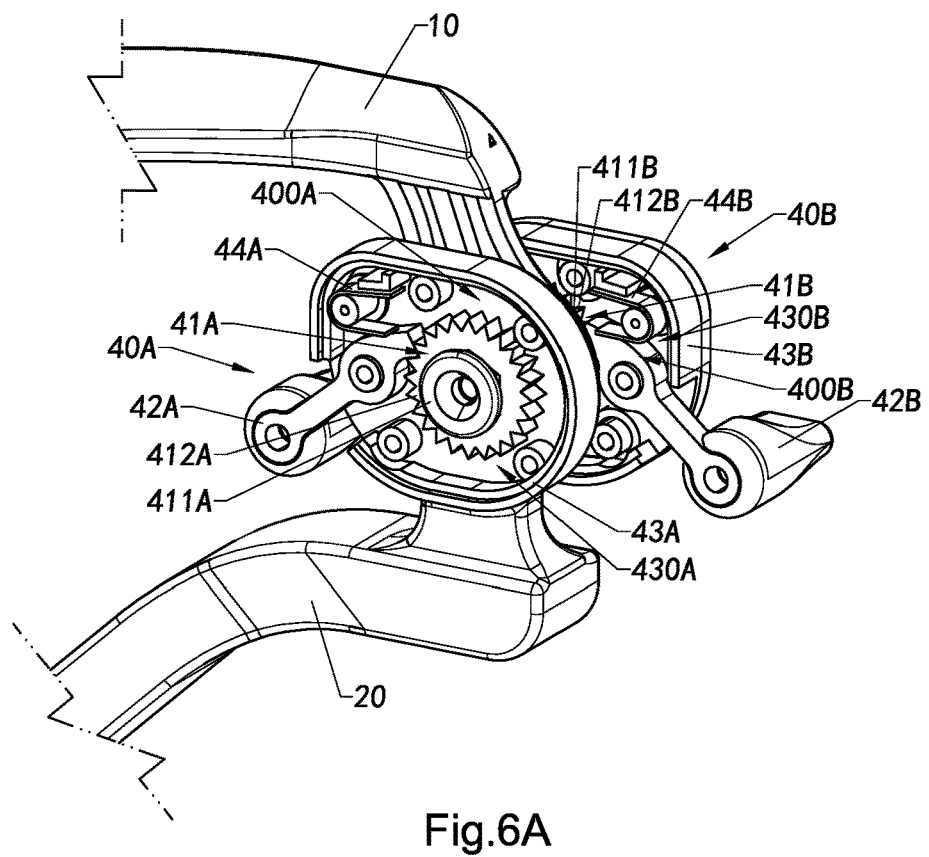
FIG. 6A is a schematic view illustrating an adjustment unit of the auxiliary support apparatus according to the above preferred embodiment of the present invention.

Referring to FIG. 6A and further referring to FIG. 1 to FIG. 3C, an alternative mode of the fixing unit is illustrated. The bearing member 10 has a locked state and an unlocked state, wherein in the locked state, the position of the bearing member 10 with respect to the wear body 21 of the wear member 20 can be adjusted and the adjusted position after adjustment can be fixed. In the unlocked state, the bearing member 10 cannot be fixedly supported to the wear body 21 of the wear member 20.

In particular, the auxiliary support apparatus 1000 further comprises at least two fixing units, including a first fixing unit 40A and a second fixing unit 40B, wherein the first fixing unit 40A and the second fixing unit 40B are located at the junction between the bearing member 10 and the wear body 21 of the wear member 20, and that by means of such fixing unit, the relative positions of the bearing member 10 and the wear body 21 of the wear member 20 with respect to each other are adjusted and fixed in their adjusted positions after the adjustment is completed.

The first fixing unit 40A comprises a first gear rotating shaft 41A, a first lever 42A, a first housing 43A, and a first elastic member 44A, and has a first through hole 400A, wherein the first gear rotating shaft 41A is disposed to extend outwardly from an inner side of the bearing member 10. In the locked state, the first lever 42A is supported to the first gear rotating shaft 41A, so that the first gear rotating shaft 41A can only be rotated in one direction. In the unlocked state, the first lever 42A is disengaged from the first gear rotating shaft 41A, so that the first gear rotating shaft 41A can be rotated arbitrarily forwards or backwards. The first elastic member 44A provides the effects of support and reset. In the locked state, the first elastic member 44A supports the first lever 42A, so that the first lever 42A keeps blocking the gear rotating shaft 41A to rotate in the opposite direction. In the unlocked state, the first elastic member 44A provides an elastic force to assist the first lever 42A to return to preventing the first gear rotating shaft 41A from rotating in the opposite direction. The first housing 43A has a first receiving cavity 430A. The first gear rotating shaft 41A and the first elastic member 44A are received in the first receiving cavity 430A. A portion of the first lever 42A is received in the first receiving cavity 430A while another portion of the first lever 42A is exposed outside the first receiving cavity 430A, so as to be operated conveniently. The first through hole 400A is formed in the wear body 21 of the wear member 20, and the first gear rotating shaft 41A is arranged to the bearing member 10. The relative rotation between the bearing member 10 and the wear body 21 of the wear member 20 is achieved by the rotation of the first gear rotating shaft 41A in the first through hole 400A.

The first gear rotating shaft 41A comprises a first shaft main body 412A and a first wheel gear 411A, wherein the first shaft main body 412A passes through the first through hole 400A. One end of the first shaft main body 412A is connected to the bearing member 10. The other end of the first shaft main body 412A is connected to the first wheel gear 411A. The first wheel gear 411A is larger than the first through hole 400A, so that the first gear rotating shaft 41A cannot be removed from the first through hole 400A.

Regarding the second fixing unit 40B, the second fixing unit 40B comprises a second gear rotating shaft 41B, a second lever 42B, a second housing 43B, and a second elastic member 44B, and has a second through hole 400B, wherein the second gear rotating shaft 41B is disposed to extend outwards from an inner side of the bearing member 10. In the locked state, the second lever 42B is supported to the second gear rotating shaft 41B, so that the second gear rotating shaft 41B can only be rotated in one direction. In the unlocked state, the second lever 42B is disengaged from the second gear rotating shaft 41B, so that the second gear rotating shaft 41B can be rotated arbitrarily forwards or backwards. The second elastic member 44B provides the effects of support and reset. In the locked state, the second elastic member 44B supports the second lever 42B, so that the second lever 42B keeps blocking the gear rotating shaft 41B to rotate in the opposite direction. In the unlocked state, the second elastic member 44B provides an elastic force to assist the second lever 42B to return to preventing the second gear rotating shaft 41B from rotating in the opposite direction. The second housing 43B has a second receiving cavity 430B. The second gear rotating shaft 41B and the second elastic member 44B are received to the second receiving cavity 430B. A portion of the second lever 42B is received in the second receiving cavity 430B and another portion of the second lever 42B is exposed outside the second receiving cavity 430B, so as to be operated conveniently. The second through hole 400B is formed in the wear body 21 of the wear member 20, and the second gear rotating shaft 41B is arranged to the bearing member 10. The relative rotation between the bearing member 10 and the wear body 21 of the wear member 20 is achieved by the rotation of the second gear rotating shaft 41B in the second through hole 400B.

The second gear rotating shaft 41B comprises a second shaft main body 412B and a second wheel gear 411B, wherein the second shaft main body 412B passes through the second through hole 400B. One end of the second shaft main body 412B is connected to the bearing member 10. The other end of the second shaft main body 412B is connected to the second wheel gear 411B. The second wheel gear 411B is larger than the second through hole 400B, so that the second gear rotating shaft 41B cannot be removed from the second through hole 400B.

In other words, the first fixing unit 40A and the second fixing unit 40B are respectively located at two sides of the bearing member 10 and are respectively connected to the wear body 21 of the wear member 20.

It is worth mentioning that, while the first fixing unit 40A and the second fixing unit 40B are in the locked state, the first gear rotating shaft 41A and the second gear rotating shaft 41B are opposite to each other in the moving direction. For example, the first fixing unit 40A can be adjusted in the clockwise direction and then its adjusted position can be fixed; the second fixing unit 40B can be adjusted in the counterclockwise direction and then its adjusted position can be fixed, so that the position of the entire auxiliary support apparatus 1000 can be adjusted arbitrarily towards the front direction or the rear direction and such adjusted position can be fixed in position too.

More particularly, while the user needs to adjust the bearing member 10 in the clockwise direction, it is only necessary to operate the second lever 42B of the second fixing unit 40B so that the second lever 42B does not block the second gear rotating shaft 41B to move in the clockwise direction. While the user needs to adjust the bearing member 10 in the counterclockwise direction, only the first lever 42A of the first fixing unit 40A is needed to be operated in such a manner that the first lever 42A does not prevent the first gear rotating shaft 41A from moving in the counterclockwise direction.

It would be understood that the first gear rotating shaft 41A and the second gear rotating shaft 41B can be the same gear rotating shaft spanning the end of the bearing member 10, which is extended from the end of the bearing member 10 to two sides simultaneously. The first gear rotating shaft 41A and the second gear rotating shaft 41B may also be two gear rotating shafts, so that the minimum adjustment angle in the counterclockwise direction and the minimum adjustment angle in the clockwise direction are different due to the difference between the first wheel gear 411A and the second wheel gear 411B.

It would be understood that the positions and structures of the first fixing unit 40A and the second fixing unit 40B are not limited to the above description. The first fixing unit 40A and the second fixing unit 40B can be located at the same side of the bearing member 10. The first fixing unit 40A and the second fixing unit 40B can be arranged into the same housing 43, or one of the rotating shaft main bodies 412 is provided with two gears and two levers.

Figure 6B:
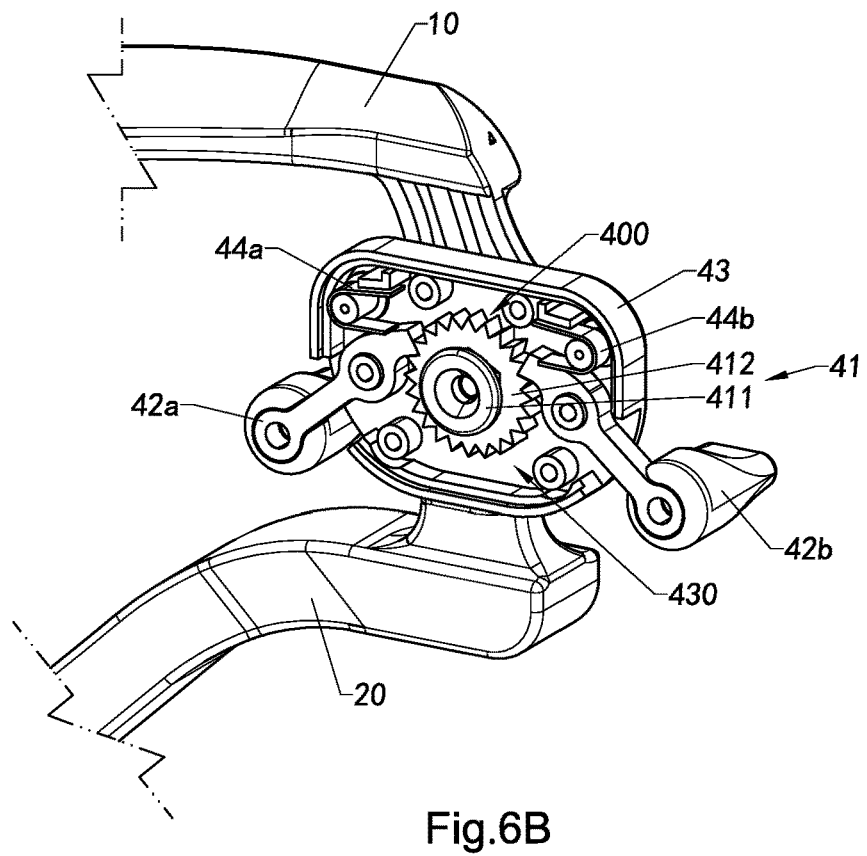
FIG. 6B is a schematic view illustrating an adjustment unit of the auxiliary support apparatus according to the above preferred embodiment of the present invention.

Referring to FIG. 6B, another alternative mode of the fixing unit is illustrated.

Further referring to FIG. 1 to FIG. 3C, the auxiliary support apparatus 1000 comprises the bearing member 10, the wear body 21 of the wear member 20, and the auxiliary wear support 22, wherein the bearing member 10 is used to support the head, wherein the wear body 21 of the wear member 20 supports the bearing member 10 to the body portion below the user's head. The wear body 21 of the wear member 20 extends downwardly from the bearing member 10. Two ends of the auxiliary wear support 22 are respectively connected to two ends of the bearing member 10. The auxiliary wear support 22 and the wear body 21 of the wear member 20 together define the wear passage 100. The size of the wear passage 100 can be adjusted, so that the auxiliary support apparatus 1000 can be adapted to necks and heads with different sizes.

The bearing member 10 has a locked state and an unlocked state, wherein in the locked state, the position of the bearing member 10 with respect to the wear body 21 of the wear member 20 can be adjusted and its adjusted position can be fixed. In the unlocked state, the bearing member 10 cannot be fixedly supported to the wear body 21 of the wear member 20.

The auxiliary support apparatus 1000 further comprises a fixing unit 40, wherein the fixing unit 40 comprises a gear rotating shaft 41, a first lever 42A, a second lever 42B, a first elastic member 44A, and a second elastic portion 44B, and has a through hole 400, wherein the gear rotating shaft 41 is formed at two ends of the bearing member 10. The through hole 400 is formed at both ends of the wear body 21 of the wear member 20. It would be understood that, according to other embodiments of the present invention, the positions of the gear rotating shaft 41 and the through hole 400 can be interchanged. In other words, the gear rotating shaft 41 is formed on the wear body 21 of the wear member 20. The through holes 400 are formed at both ends of the bearing member 10. The gear rotating shaft 41 is fitted to the through hole 400. In detail, the gear rotating shaft 41 comprises a rotating shaft main body 412 and a wheel gear 411, wherein one end of the rotating shaft main body 412 is connected to the bearing member 10, and the other end is connected to the wheel gear 411. The rotating shaft main body 412 passes through the through hole 400 and is slightly smaller than the through hole 400, so that the rotating shaft main body 412 can be rotated with respect to the through hole 400. The wheel gear 411 is larger than the through hole 400 such that the bearing member 10 cannot be detached from the wear body 21 of the wear member 20.

The auxiliary support apparatus 1000 has a supporting state and an unsupporting state. In the supporting state, the including angle between the bearing member 10 and the wear body 21 of the wear member 20 can be adjusted, and such adjusted including angle can be fixed. In the unsupporting state, the including angle between the bearing member 10 and the wear body 21 of the wear member 20 can be adjusted, but such adjusted position cannot be maintained.

Furthermore, in the supporting state, the bearing member 10 can be selectively rotated in the clockwise or counterclockwise direction with respect to the wear body 21 of the wear member 20. In detail, in the supporting state, the fixing unit 40 has two states, including a first state that the gear rotating shaft 41 can be rotated in the clockwise direction, and a second state that the gear rotating shaft 41 can be rotated in the counterclockwise direction. The fixing unit 40 is switchable between the first state and the second state. In the first state, the first lever 42A of the gear rotating shaft 41 prevents the gear rotating shaft 41 from rotating in the counterclockwise direction, and in the second state, the second lever 42B of the gear rotating shaft 41 prevents the gear rotating shaft 41 from rotating in the clockwise direction. In other words, the first lever 42A and the second lever 42B prevent the rotation of the gear rotating shaft 41 from being rotated in opposite direction.

The fixing unit 40 further comprises a housing 43, wherein the first lever 42A and the second lever 42A are respectively connected to the housing 43, and the first lever 42A and the second levers 42B are movably connected to the housing 43. The first lever 42A has a blocking state and a non-blocking state, wherein in the blocking state, the first lever 42A prevents the gear rotating shaft 41 from rotating in the counterclockwise direction. In the non-blocking state, the first lever 42A does not block the rotation of the gear rotating shaft 41 in the counterclockwise direction. The second lever 42B has a blocking state and a non-blocking state. In the blocking state, the second lever 42B prevents the gear rotating shaft 41 from rotating in the clockwise direction, and in the non-blocking state, the second lever 42B does not block the rotation of the gear rotating shaft 41 in the clockwise direction.

While the first lever 42A and the second lever 42B are both in the blocking state, the gear rotating shaft 41 cannot move in the clockwise or in the counterclockwise direction, so that the bearing member 10 is fixed to the wear body 21 of the wear member 20. It is worth mentioning that the first lever 42A and the second lever 42B are simultaneously supported to the gear rotating shaft 41 to prevent rotation, so that the bearing member 10 is more stably supported to the wear body 21 of the wear member 20.

While the first lever 42A and the second lever 42B are both in the non-blocking state, the gear rotating shaft 41 can be arbitrarily moved in the clockwise or in the counterclockwise direction, so that the bearing member 10 can be arbitrarily rotated around the gear rotating shaft 41 but its position cannot be fixed. While the first lever 42A is in the blocking state, and the second lever 42B is in the non-blocking state, the gear rotating shaft 41 can be rotated only in the clockwise direction. While the first lever 42A is in the non-blocking state, the second lever 42B is in the blocking state, the gear rotating shaft 41 can be rotated only in the counterclockwise direction.

The first lever 42A and the second lever 42B are operatively connected to the housing 43 respectively. Both the first lever 42A and the second lever 42B are partially received in a receiving chamber of the housing 43, so that a user can operate the first lever 42A and the second lever 42B outside the housing 43 to control the position and state of the bearing member 10.

It would be understood that the blocking direction of the first lever 42A and the second lever 42B is merely an example. Alternatively, the first lever 42A may prevent the gear rotating shaft 41 from rotating the clockwise direction; the second lever 42B prevents the gear rotating shaft 41 from rotating in the counterclockwise direction. Alternatively, the number of the first control levers 42A is not limited to one, and the number of the second control levers 42B is not limited to one.

Figure 7:
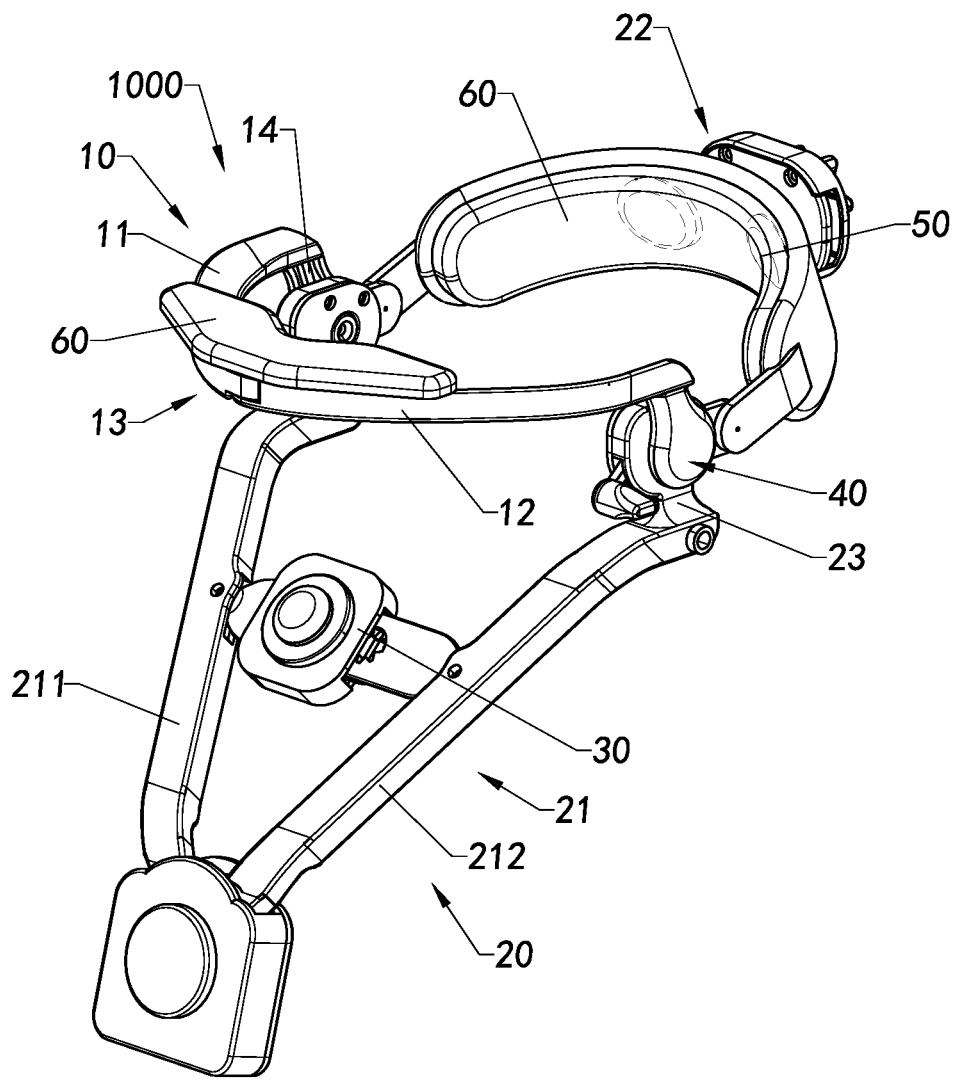
FIG. 7 is a perspective view of the auxiliary support apparatus according to the above preferred embodiment of the present invention.

Referring to FIG. 7, the different from this alternative embodiment with the preferred embodiment shown in FIG. 1 to FIG. 3C is that, the auxiliary support apparatus 1000 further comprises one or more flexible pads 60, wherein the one or more flexible pads 60 are attached to the bearing member 10, the auxiliary wear support 22 and the wear body 21 of the wear member 20 respectively. The one or more flexible pads 60 are arranged, so that the user will feel more comfortable while his/her body contacting with the bearing member 10, the auxiliary wear support 22, and the wear body 21 of the wear member 20.

The flexible pad 60 attached to the bearing member 10 is configured for changing along with the changing of the including angle between the first bearing arm 11 and the second arm 12.

The flexible pad 60 attached to the auxiliary wear support 22 can be pressed to change the length along with the changing of the angles between the first locking connector 221 and the second locking connector 222.

The flexible pad 60 attached to the wear body 21 of the wear member 20 can be pressed to change the height together with the change in the height of the wear body 21 of the wear member 20.

The one or more flexible pads 60 attached to the bearing member 10, the auxiliary wear support 22 and the flexible pad 60 of the wear body 21 of the wear member 20 can be provided integrally or detachably.

Figure 8:
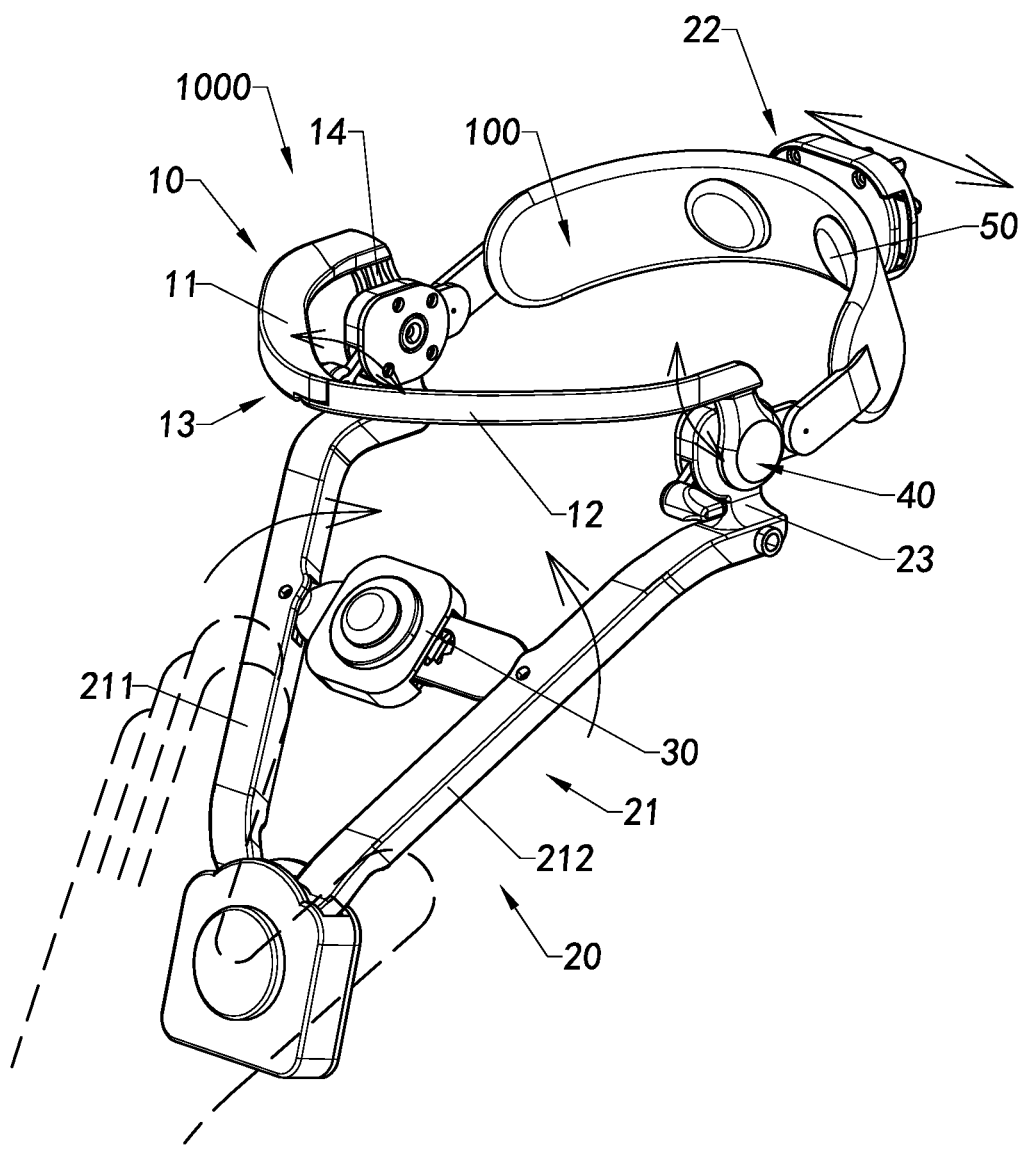
FIG. 8 is a perspective view of the auxiliary support apparatus according to the above preferred embodiment of the present invention.

FIG. 8 illustrates an application of the auxiliary support apparatus 1000 as illustrated in FIG. 1 to FIG. 3C. The auxiliary support apparatus 1000 supports the user's head to the torso/trunk portion, so as to reduce the pressure of the head against the neck and thus to assist the neck to support the head.

In particular, the bearing member 10 comprises the first bearing arm 11 and the second bearing arm 12, wherein the first bearing arm 11 and the second bearing arm 12 are pivotally connected with each other to define the including angle formed between the first bearing arm 11 and the second bearing arm 12, wherein the including angle is an acute angle. The first bearing arm 11 and the second bearing arm 12 define and surround a portion of the wear passage 100. The first bearing arm 11 and the second bearing arm 12 are respectively shaped and configured to fit the jawbone of the head so as to support the head of the user. The bearing member 10 is shaped and arranged to be in a U-shape or a V-shape structure, and that the including angle formed between the first bearing arm 211 and the second bearing arm 212 is arranged to be adjustable, so that the user is capable of changing the supporting angle of the bearing member 10 with respect to the head of the user while using the auxiliary support apparatus 1000.

The wear body 21 comprises the first support arm 211 and the second support arm 212, wherein the first support arm 211 and the second support arm 212 respectively extend from two ends of the bearing member 10 downwardly. The first support arm 211 and the second support arm 212 form a U-shaped or a V-shaped structure. An included angle is defined and formed between the first support arm 211 and the second support arm 212, wherein the included angle defined between the first support arm 211 and the second support arm 212 is arranged to be adjustable, so that the user is capable of changing the supporting angle of the wear body 21 with respect to the torso/trunk of the user.

It can be understood that the wear body 21 can be worn to the front chest of the user or can be worn to the back of the user. According to this embodiment, the wear body 21 is worn to the user's chest.

The bearing member 10 is connected to the wear body 21. The wear body 21 is supported to a user's trunk. The bearing member 10 is supported to the wear body 21, so that the bearing member 10 can support the head of the user that provides an auxiliary support ability to the neck of the user correspondingly. According to other embodiments of the present invention, the bearing member 10 may be liftably connected to the wear body 21. In other words, the entire bearing member 10 is connected to the wear body 21 in such a manner that the height with respect to the wear body 21 can be raised or lowered, so as to accommodate with different heights of the necks of different users.

According to this preferred embodiment of the present invention, the bearing member 10 is rotatably connected to the wear body 21 and that the position of the bearing member 10 after rotation adjustment can be fixedly connected to the wear body 21 to accommodate different heights of the necks of different users. The bearing member 10 can be rotated upwardly with respect to the wear body 21 when the neck of the user is in a higher position or the user needs to remain in a looking up state. For the entire auxiliary support apparatus 1000, the highest position is at the junction position of the first bearing arm 11 and the second bearing arm 12 of the bearing member 10, that position is capable of supporting the chin of the head of the user, so as to keep the user in the looking up state.

Furthermore, the first bearing arm 11 of the bearing member 10 corresponds to the first support arm 211 of the wear body 21, and the second bearing arm 12 of the bearing member 10 corresponds to the second support arm 212 of the main body 21. In particular, one end of the first bearing arm 11 is pivotally connected to one end of the second bearing arm 12, and the other ends of the first bearing arm 11 and the second bearing arm 12 are connected to the first support arm 211 and the second support arm 212 respectively.

One end of the first support arm 211 is foldably connected to the first bearing arm 11, and the other end of the first support arm 211 is foldably connected to the second support arm 212. One end of the second support arm 212 is foldably connected to the second bearing arm 12, and the other end of the second support arm 212 is foldably connected to the first support arm 211.

After the included angle between the first support arm 211 and the second support arm 212 is reduced, the first bearing arm 11 connected to the first support arm 211 and the second bearing arm 12 of the second support arm 212 is driven such that the including angle between the first bearing arm 11 and the second bearing arm 12 is reduced correspondingly.

It is worth mentioning that after the widths of the wear body 21 and the bearing member 10 are simultaneously reduced, the wear body 21 and the bearing member 10 can be held at such reduced position. Similarly, after the widths of the wear body 21 and the bearing member 10 are simultaneously enlarged, the wear body 21 and the bearing member 10 can be held at such enlarged position.

In particular, the auxiliary support apparatus 1000 comprises the adjustment unit 30, wherein the adjustment unit 30 is positioned between the first support arm 211 and the second support arm 212 and is respectively connected to the first support arm 211 and the second support arm 212. Under the effect of the adjustment unit 30, the folding widths or the adjustment ranges of the first support arm 211 and the second support arm 212 can be kept correlated proportional, so that the folding widths or the adjustment ranges of the first bearing arm 11 and the second bearing arm 12 respectively driven by the first support arm 211 and the second support arm 212 can also be kept correlated proportional.

The adjustment unit 30 is capable of restricting a relative displacement between the first support arm 211 and the second support arm 212 and restricting a relative displacement between the bearing arm 11 and the second bearing arm 12 through the first support arm 211 and the second support arm 212.

In this manner, the auxiliary support apparatus 1000 can be folded not only in the height direction or the length direction but also in the width direction. When the auxiliary support apparatus 1000 is not in use, the occupying space for storage of the auxiliary support apparatus 1000 can be greatly reduced.

Figure 2:
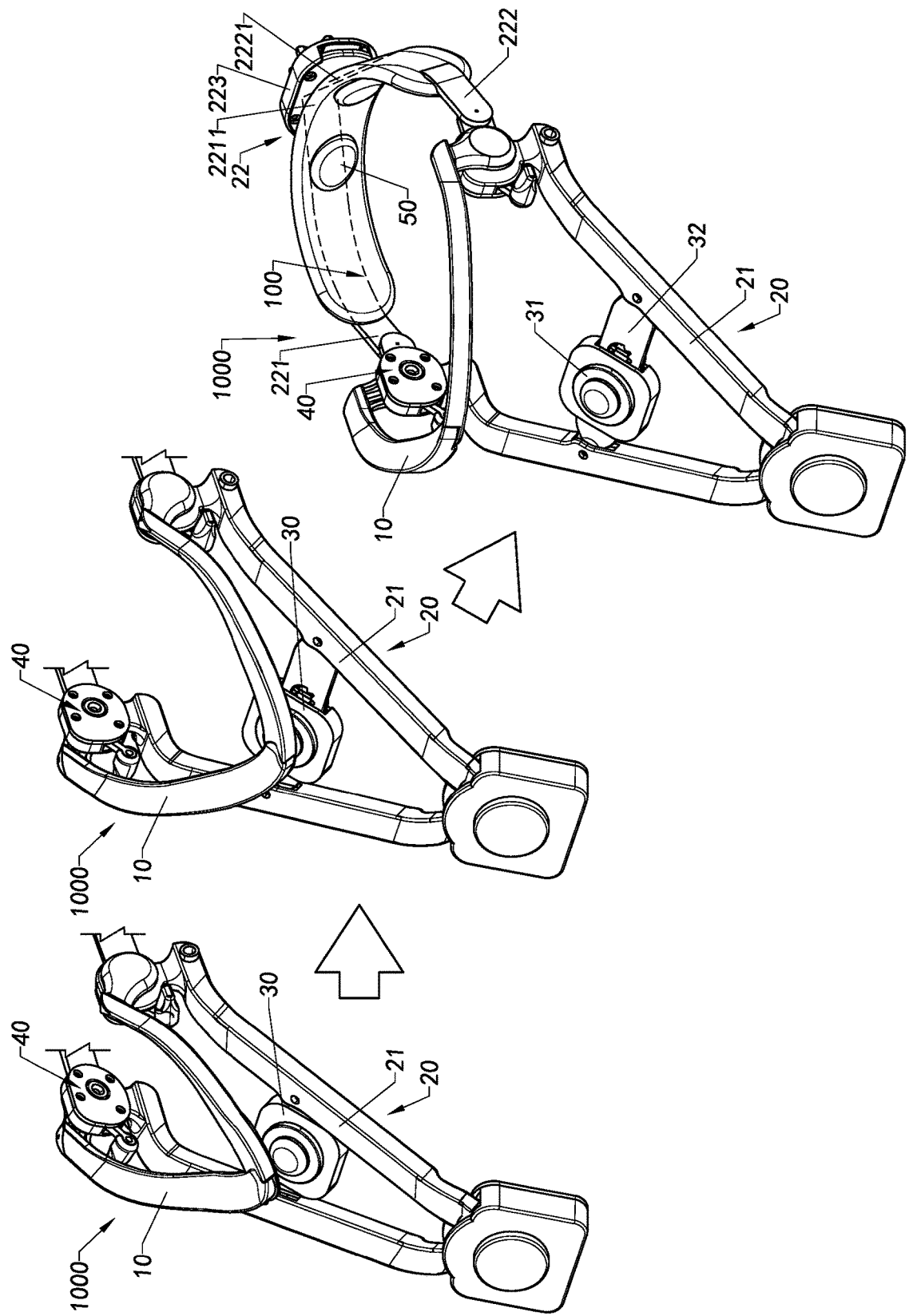
FIG. 2 is a schematic view illustrating an application of the auxiliary support apparatus according to the above preferred embodiment of the present invention.

In particular, as shown in FIGS. 1, 2 and 3C, the adjustment unit 30 comprises an adjusting mechanism 31 and two adjusting members 32, wherein the adjusting mechanism 31 is connected to both the two adjusting members 32 for adjusting the adjustment members 32, so as to change the length of the adjustment unit 30 and thus to change the positions of the first support arm 211 and the second support arm 212 connected to two ends of the adjustment unit 30 respectively and the included angle between the second support arm 212 and first support arm 211.

It is worth mentioning that the two adjustment members 32 can be adjusted synchronously by the adjusting mechanism 31, so that the first support arm 211 and the second support arm 212 respectively connected to the two adjustment members 32 can be adjusted synchronously. In other words, the first support arm 211 and the second support arm 212 can move the same distance towards an intermediate position between the first support arm 211 and the second support arm 212. In other words, the first support arm 211 and the second support arm 212 are capable of moving the same distance toward each other. Of course, the first support arm 211 and the second support arm 212 can move the same distance in a direction away from each other. In this manner, the user can conveniently adjust the first support arm 211 and the second support arm 212, and the adjustment to the first support arm 211 and the second support arm 212 can be accomplished by a single operation to the adjustment mechanism 31, so as to change the included angle between the first support arm 211 and the second support arm 212, and thus change the including angle formed by the first bearing arm 11 and the second bearing arm 12 correspondingly, so that the auxiliary support apparatus 1000 is able to be adjusted to fit the mandibular portion of the heads of different users.

Furthermore, the adjustment mechanism 31 comprises the operation portion 311 and the control portion 312, wherein the control portion 312 is connected to two adjustment members 32. The operation portion 311 is connected to the control portion 312 and can drive the control portion 312 of the adjustment member 32, so that the first support arm 211 and the second support arm 212 connected to the adjustment member 32 can be adjusted accordingly. In other words, one end of the adjusting member 32 is connected to the first support arm 211, and the other end is connected to the control portion 312. One end of the other adjusting member 32 is connected to the support arm 212, and the other end is connected to the control portion 312.

More particularly, the control portion 312 comprises the control body 3121 and the control gear 3122, wherein the control gear 3122 is formed around the control body 3121. The control portion 312 has a connection hole 3120 through which the operation portion 311 is connected to the control body 3121.

The adjustment member 32 comprises the adjustment body 321 and the adjustment assembly 322 and has the adjustment passage 320, wherein the adjustment passage 320 is formed at one end of the adjustment body 321, wherein the adjustment assembly 322 and the adjustment passage 320 are formed at the same end of the adjustment body 321. The adjustment assembly 322 has a toothed structure formed around the adjustment passage 320.

The adjustment member 32 is mounted to the control portion 312, and the adjustment member 322 of the adjustment member 32 is engaged to the control gear 3122 of the control portion 312. Two adjusting members 32 are respectively positioned at two sides of the control portion 312 and are respectively connected to the control portion 312.

One end of the adjusting member 32 connected to the control portion 312 is overlapped with one end of the other adjusting member 32 connected to the control portion 312. The end of the adjusting member 32 connected to the control portion 312 and the end of the other adjusting member 32 connected to the control portion 312 are respectively engaged to the control gear 3122 of the control portion 312.

Furthermore, the adjustment member 32 has a length direction, wherein the adjustment passage 320 is extended in the length direction of the adjustment member 32. The adjustment assembly 322 is formed around the channel 320 along the length direction of the adjustment member 32. When the operation portion 311 controls the control portion 312 to rotate and further drives the adjustment member 32 to move, a positional change between the adjustment member 32 and the control portion 312 is a relative position change along the adjustment passage 320. In other words, the position of the control portion 312 at the adjustment passage 320 changes with the operation of the operation portion 311.

In particular, each of the adjusting members 32 has a connecting end and a free end, wherein the connecting end of one of the adjusting members 32 is connected to the connecting end of the other adjustment member 32. The free ends of the adjustment members 32 are respectively connected to the first support arm 211 and the second support arm 212. While the two adjustment members 32 move toward each other, the overlapping area of the two adjustment members 32 becomes larger and larger. The control portion 312 approaches from the connecting end toward the free end, so that a total length of the two adjustment member 32 is reduced, and the included angle between the first support arm 211 and the second support arm 212 is reduced.

It is worth mentioning that the control gear 3122 of the control portion 312 is arranged as a uniform gear. In other words, the distance between each two teeth is the same. The control gears 3122 are respectively engaged with the two adjusting members 32, so that the control gears 3122 drive the adjusting members 32 to rotate or driven by the adjusting members 32 to rotate. The two adjusting members 32 respectively move outwardly. In other words, the two adjustment members 32 can be adjusted equidistantly. The first support arm 211 and the second support arm 212 can be moved by the same distance or rotated by the same angle.

While the operating portion 311 is not operated, the positions of the control portion 312 and the adjusting member 32 are relatively fixed, so that the first support arm 211 and the second support arm 212 can be fixed at their positions to provide a rigid and secure support effect.

Furthermore, the adjusting component 322 can be formed to one side of the position of the adjusting passage 320, and the adjusting components 322 of the two adjusting component 32 are respectively formed to two sides of the control part 312, so that the control gear 3122 can be used to synchronously adjust the two adjustment members 32. Regarding the first support arm 211 and the second support arm 212, the first support arm 211 and the second support arm 212 can be adjusted by means of the adjustment unit 30 and fixed to an adjusted position after being adjusted. The first support arm 211 is rotatably connected to the second support arm 212. Alternatively, the first support arm 211 is rotatably connected to the second support arm 212 in such a manner that the first support arm 211 can be rotated an angle within a range. A stable triangular support configuration is formed among the first support arm 211, the second support arm 212 and the bearing member 10. Furthermore, the first support arm 211 and the second support arm 212 are fixed by the adjustment unit 30, so that the support to the bearing member 10 is more stable on one hand, and that the changed included angle between the first support arm 211 and the second support arm 212 can be fixed on the other hand.

In such a manner, the size of the auxiliary support apparatus 1000 in the width direction can be adjusted. When the auxiliary support apparatus 1000 is not in use, the first support arm 211 of the auxiliary support apparatus 1000 can be folded toward the second support arm 212, so that the first bearing arm 11 and the second bearing arm 12 respectively connected to the first support arm 211 and the second support arm 212 are driven to reduce the size of the auxiliary support apparatus 1000 in the width directly accordingly.

It is worth mentioning that the first bearing arm 11 of the bearing member 10 is rotatably connected to the second bearing arm 12. The change in the including angle between the first bearing arm 11 and the second bearing arm 12 ensures the size of the bearing member 10 that is capable of supporting the mandible of the head of the user to be changed accordingly.

The bearing member 10 can be supported to the wear body 21, and the bearing member 10 can freely rotate with respect to the wear body 21, so as to change the position of the bearing member 10 for supporting the head at different positions and different heights. Furthermore, the bearing member 10 can be supported at such changed position after the bearing member 10 has changed in position.

It is worth mentioning that the auxiliary support apparatus 1000 can be adjusted by a single pinch. In detail, during using the auxiliary support apparatus 1000, the user can pinch the first support arm 211 and the second support arm 212 of the wear body 21 of the auxiliary support apparatus 1000 with one hand and move the first support arm 211 and the second support arm 212 toward each other, so as to reduce a width of the wear body 21 of the auxiliary support apparatus 1000 in the width direction. Correspondingly, the two adjustment members 32 of the adjustment unit 30 drive the control portion 312 to rotate under the effect of the user's inward thrust. At the same time, the adjusting member 32 moves inwardly. After the user stops applying force, the frictional force among the adjusting member 32 of the adjustment unit 30, the control portion 312 and the operating portion 311 prevents the movement of the adjusting member 32, so that the first support arm 211 and the second support arm 212 can be held in the adjusted position through the adjustment unit 30, so as to achieve a pinch adjustment.

Figure 9A:
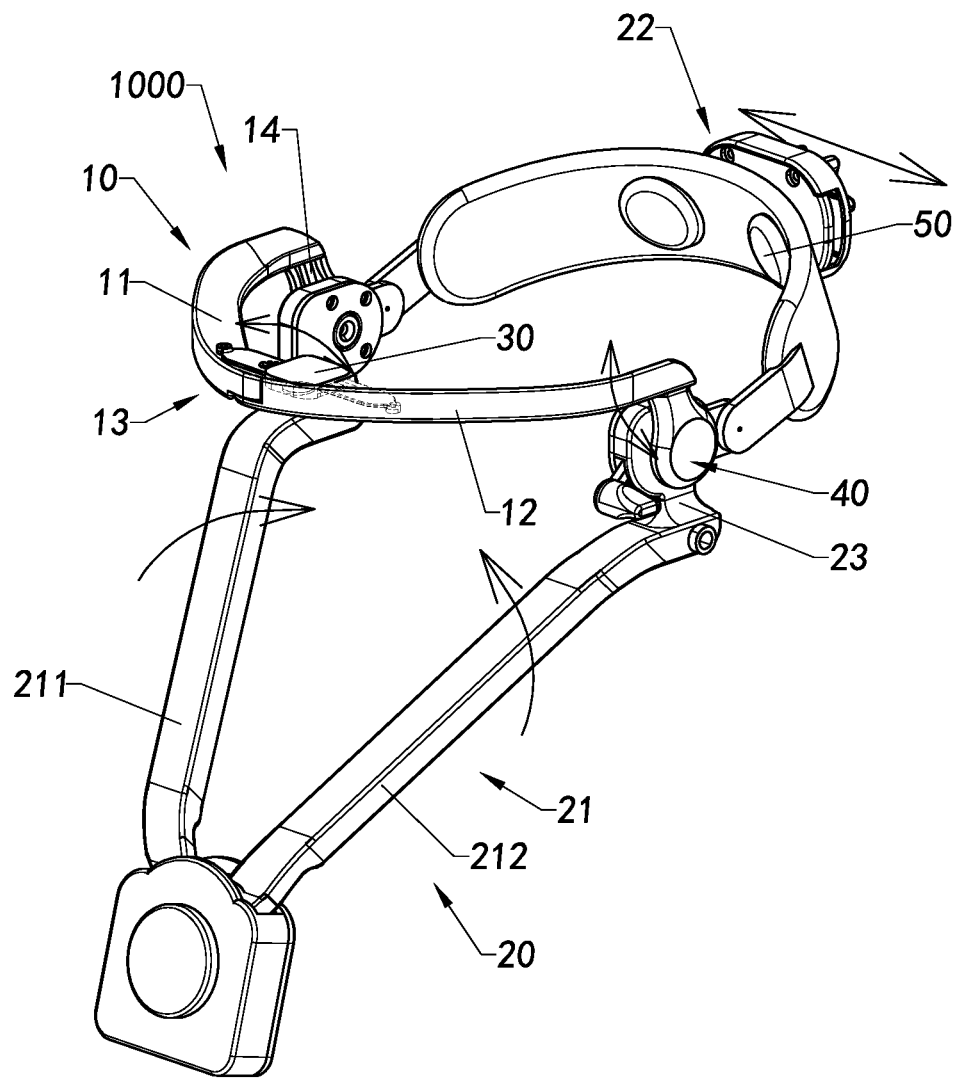
FIG. 9A is a perspective view illustrating the auxiliary support apparatus according to the above preferred embodiment of the present invention.

Referring to FIG. 9A, an alternative mode of the auxiliary support apparatus 1000 according to the above embodiment of the present invention is illustrated. The difference between this alternative mode and the above preferred embodiment as illustrated in FIG. 1 to FIG. 3C and FIG. 8 is in the adjustment unit 30.

In this alternative mode, the adjustment unit 30 is provided at the bearing member 10. The adjustment unit 30 is positioned between the first bearing arm 11 and the second bearing arm 12 and is connected to both the first bearing arm 11 and the second bearing arm 12. Under the action of the adjustment unit 30, the folding width or the adjustment width of both the first bearing arm 11 and the second bearing arm 12 can be correlatedly maintained the same amount. Correspondingly, the folding width or the adjustment range between the first support arm 211 and the second support arm 212 driven by the first bearing arm 11 and the second bearing arm 12 can also be maintained the same amount.

The adjustment unit 30 can limit the relative displacement between the first bearing arm 11 and the second bearing arm 12, and restrict the relative displacement between the first support arm and the second support arm through the first bearing arm 11 and the second bearing arm 12.

In such a manner, the auxiliary support apparatus 1000 can be folded not only in the height direction or the length direction but also in the width direction. When the auxiliary support apparatus 1000 is not in use, the occupying space of the auxiliary support apparatus 1000 can be greatly reduced.

More specifically to the adjustment unit 30, the adjustment unit 30 comprises an adjusting mechanism 31 and two adjustment members 32, wherein the adjusting mechanism 31 is connected to the two adjustment members 32 for adjusting the adjustment members 32, so as to change the length of the adjustment unit 30, to change the positions of the first support arm 211 and the second support arm 212 respectively connected to two ends of the adjustment unit 30, and to change the included angle between the first support arm 211 and the second support arm 212.

It is worth mentioning that the two adjustment members 32 can be adjusted synchronously by the adjusting mechanism 31, so that the first bearing arm 11 and the second bearing arm 12 respectively connected to the two adjustment members 32 can be adjusted synchronously. In other words, the first bearing arm 11 and the second bearing arm 12 can move an equal distance toward a middle position between the first bearing arm 11 and the second bearing arm 12. In other words, the first bearing arm 11 and the second bearing arm 12 are capable of moving an equal distance toward each other. Of course, each of the first bearing arm 11 and the second bearing arm 12 can move an equal distance in opposite directions away from each other. In such a manner, the user can conveniently adjust the first bearing arm 11 and the second bearing arm 12, such that the adjustment of the first bearing arm 11 and the second bearing arm 12 can be completed in a single operation via the adjustment mechanism 31, so as to change the including angle between the first bearing arm 11 and the second bearing arm 12 and to change the included angle defined by the first support arm 211 and the second support arm 212 correspondingly, so that the auxiliary support apparatus 1000 is able to be adjusted to fit the jawbone portions of the heads of different users.

Furthermore, the adjustment mechanism 31 comprises an operation portion 311 and a control portion 312, wherein the control portion 312 is connected to the two adjustment members 32. The operation portion 311 is connected to the control portion 312, and can drive the control portion 312 to move. The control portion 312 drives the adjustment members 32 respectively connected to the control portion 312 to move during the movement, so that the first bearing arm 11 and the second bearing arm 12 connected to the adjustment members 32 can be adjusted accordingly. In other words, one end of one adjustment member 32 is connected to the first bearing arm 11; the other end of said adjustment member 32 is connected to the control portion 312. One end of the other adjustment member 32 is connected to the second bearing arm 12; the other end of said the other adjustment member 32 is connected to the control portion 312.

In more detail, the control portion 312 comprises a control body 3121 and a control gear 3122, wherein the control gear 3122 is formed around the control body 3121. The control portion 312 has a connection hole 3120 through which the operation portion 311 is connected to the control body 3121.

The adjustment member 32 comprises an adjustment body 321 and an adjustment assembly 322, and has an adjustment passage 320, wherein the adjustment passage 320 is formed at one end of the adjustment body 321, wherein the adjustment assembly 322 and the adjustment passage 320 are formed at the same end of the adjustment body 321. The adjustment assembly 322 has a toothed configuration arranged around the adjustment passage 320.

While the adjustment member 32 is mounted to the control portion 312, the adjustment assembly 322 of the adjustment member 32 is engaged to the control gear 3122 of the control portion 312. Two adjustment members 32 are respectively positioned at two sides of the control portion 312 and are respectively connected to the control portion 312.

One end of the adjustment member 32 connected to the control portion 312 is overlapped with one end of the other adjustment member 32 connected to the control portion 312 and are respectively engaged to the control gear 3122 of the control portion 312.

Furthermore, the adjustment member 32 has a length direction, wherein the adjustment passage 320 is extended in the length direction of the adjustment member 32. The adjustment assembly 322 is formed around the adjustment passage 320 along the length direction of the adjustment member 32. While the operation portion 311 controls the control portion 312 to rotate to drive the adjustment member 32 to move, a positional change between the adjustment member 32 and the control portion 312 is a relative position change along the adjustment passage 320. In other words, the position of the control portion 312 at the adjustment passage 320 changes with the operation to the operation portion 311.

In particular, each adjustment member 32 has a connecting end and a free end, wherein the connecting end of one adjustment members 32 is connected to the connecting end of the other adjustment member 32. The free ends of the adjustment members 32 are respectively connected to the first bearing arm 11 and the second bearing arm 12. While the two adjustment members 32 move toward each other, the overlapping area between the two adjustment members 32 is more and more, and the control portion 312 approaches toward the free end from the connecting end, so that a total length of the two adjustment members 32 is reduced and thus the including angle between the first bearing arm 11 and the second bearing arm 12 is reduced too.

It is worth mentioning that the control gear 3122 of the control portion 312 is arranged as a uniform gear. In other words, the distance between each two teeth is the same. The control gears 3122 are respectively engaged with the two adjusting members 32, so that the control gears 3122 drive the adjusting members 32 to rotate or driven by the adjusting members 32 to rotate. The two adjusting members 32 respectively move outwardly. In other words, the two adjustment members 32 can be adjusted equidistantly. The first bearing arm 11 and the second bearing arm 12 can be moved for the same distance or rotated for the same angle.

While the operating portion 311 is not operated, the position of the control portion 312 and the adjusting member 32 are relatively fixed, so that the first bearing arm 11 and the second bearing arm 12 can be fixed at a position for rigid and secure supporting effect.

Furthermore, the adjusting component 322 can be formed to one side of the position of the adjusting passage 320, and the adjusting components 322 of the two adjusting component 32 are respectively formed to two sides of the control part 312, so that the control gear 3122 can be used to synchronously adjust the two adjustment members 32. For the first bearing arm 11 and the second bearing arm 12, the first bearing arm 11 and the second bearing arm 12 can be adjusted via the adjustment unit 30 and fixed to an adjusted position after being adjusted. The first bearing arm 11 is rotatably connected to the second bearing arm 12. Alternatively, the first bearing arm 11 is rotatably connected to the second bearing arm 12 in such a manner that the first bearing arm 11 can be rotated an angle within a range. A stable triangular support configuration is formed among the first bearing arm 11, the second bearing arm 12 and the bearing member 10. The first bearing arm 11 and the second bearing arm 12 are fixed by the adjustment unit 30, so that the support to the bearing member 10 is more stable on one hand, and that the changed angle between the first bearing arm 11 and the second bearing arm 12 can be fixed on the other hand.

In such a manner, the size of the auxiliary support apparatus 1000 in the width direction can be adjusted. When the auxiliary support apparatus 1000 is not in use, the first bearing arm 11 of the auxiliary support apparatus 1000 can be folded toward the second bearing arm 12, so that the first bearing arm 11 and the second bearing arm 12 respectively connected to the first bearing arm 11 and the second bearing arm 12 are driven to complete the size reduction of the auxiliary support apparatus 1000 in the width direction.

Furthermore, the first support arm 211 of the wear body 21 is rotatably connected to the second support arm 212. The changing of the included angle between the first support arm 211 and the second support arm 212 changes the position of the fulcrum of the auxiliary support apparatus 1000 at the shoulder of the user.

Figure 9B:
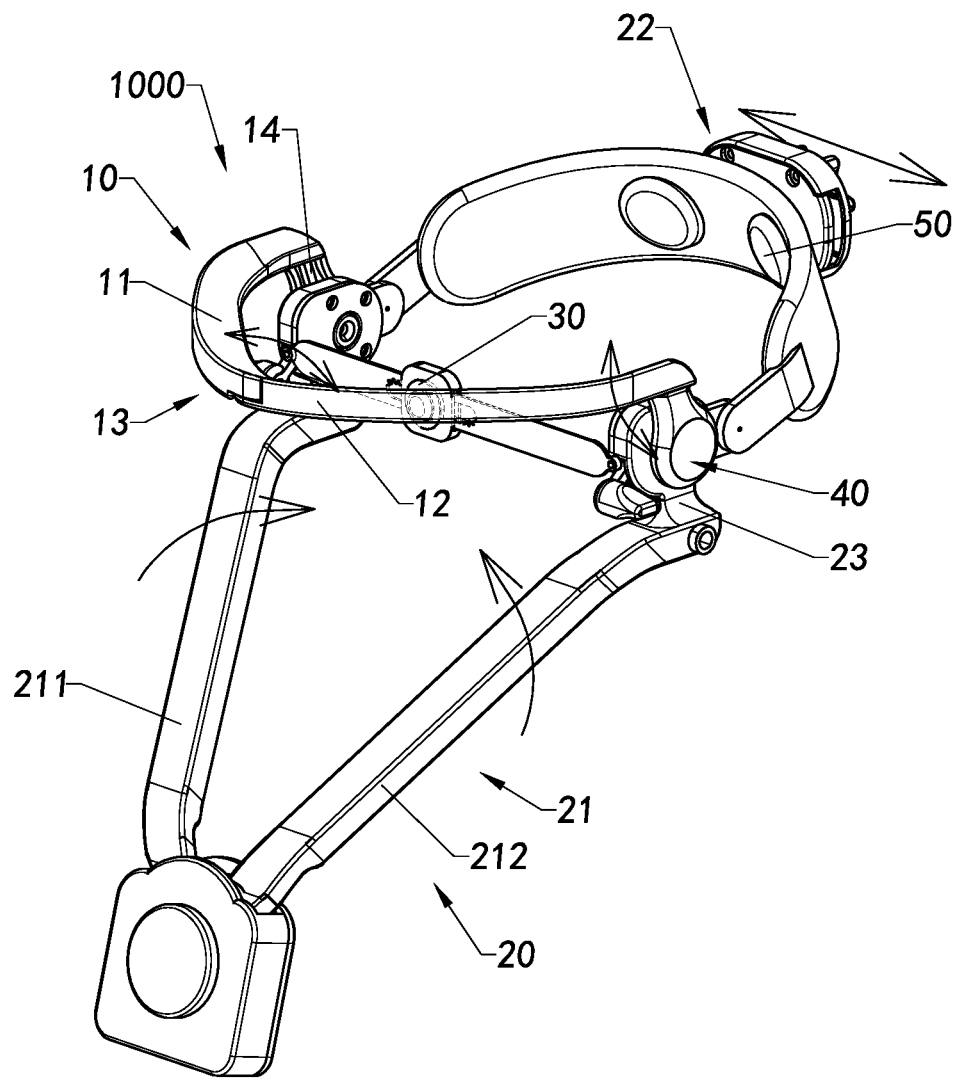
FIG. 9B is a perspective view illustrating the auxiliary support apparatus according to the above preferred embodiment of the present invention.

Referring to FIG. 9B, another alternative mode of the auxiliary support apparatus 1000 according to the above preferred embodiments of the present invention is illustrated. The difference between this another alternative mode and the above preferred embodiments is the position of the adjustment unit 30 as described below.

According to this alternative mode, the adjustment unit 30 is positioned at a joint of the bearing member 10 and the wear body 21, and the adjustment unit 30 is positioned at the fixing unit 40. The fixing unit 40 is connected to both the bearing member 10 and the wear body 21. At the time of adjusting of the width of the fixing unit 40 via the adjustment unit 30, the width of the bearing member 10 and the wear body 21 are also adjusted correspondingly.

Figure 10:
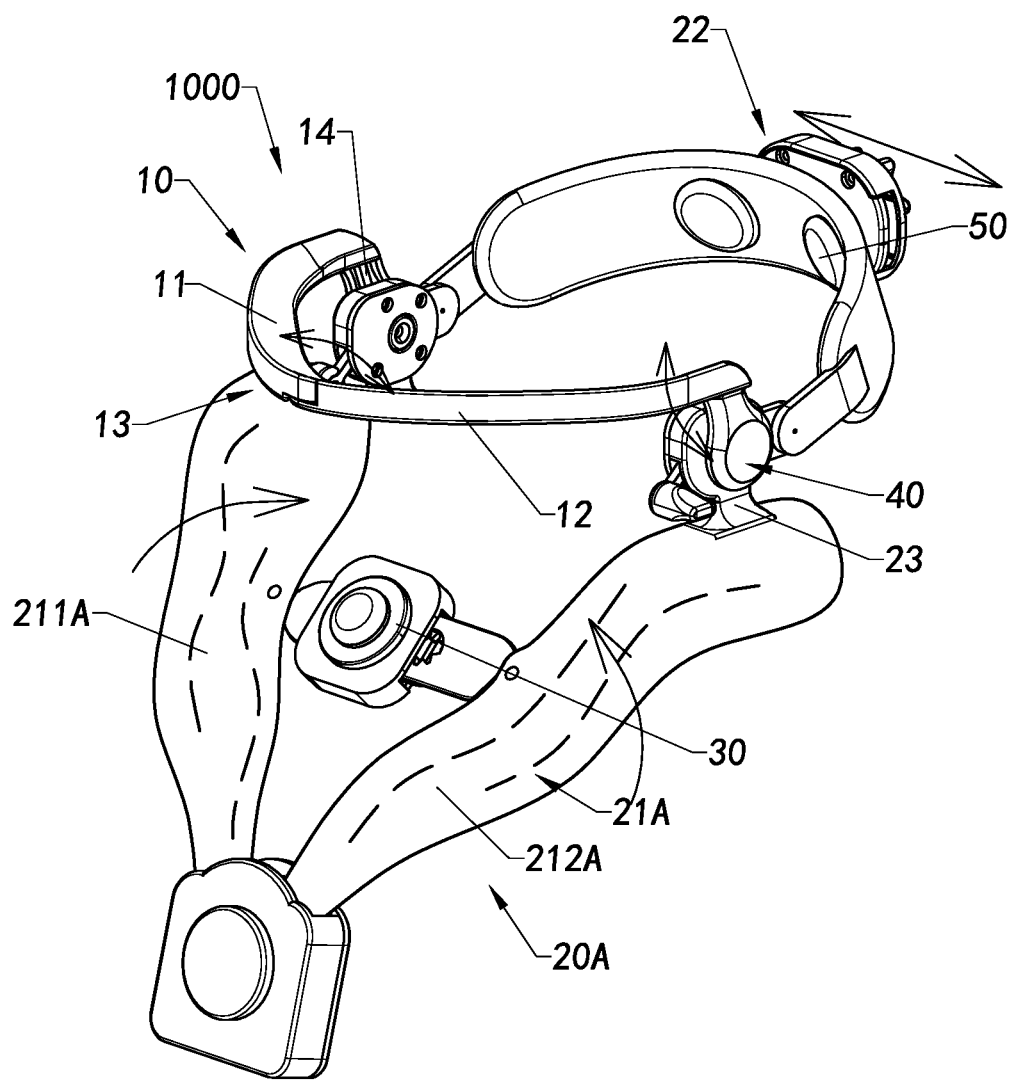
FIG. 10 is a perspective view illustrating the auxiliary support apparatus according to the above preferred embodiment of the present invention.

Referring to FIG. 10, another alternative mode of the auxiliary support apparatus 1000 according to the above preferred embodiments of the present invention is illustrated. The difference between the this alternative mode and the above preferred embodiments is the wear body 21A as follows.

The wear body 21A comprises a first support arm 211A and a second support arm 212A, wherein the first support arm 211A is connected to the second support arm 212A. In this alternative mode, the first support arm 211A is formed by inflation, and the second support arm 212A is also formed by inflation, and the first support arm 211A is connected to the second Support arm 212A. After the first support arm 211A and the second support arm 212A are filled with air, the support portion 10 can be supported to the user's trunk.

Two ends of the adjustment unit 30 are respectively connected to a predetermined position of the first support arm 211A and a predetermined position of the second support arm 212A. Preferably, the first support arm 211A and the second support arm 212A are symmetrical with each other, and the adjustment units 30 are symmetrically mounted to the first support arm 211A and the second support arm 212A respectively.

By controlling the adjustment unit 30, the distance between the free ends of the first support arm 211A and the second support arm 212A of the wear body 21A can be changed, so as to change the position of the support point of the wear body 21A on the shoulder of the user, and that the distance between the ends of the bearing member 10 is changed at the same time.

Figure 11:
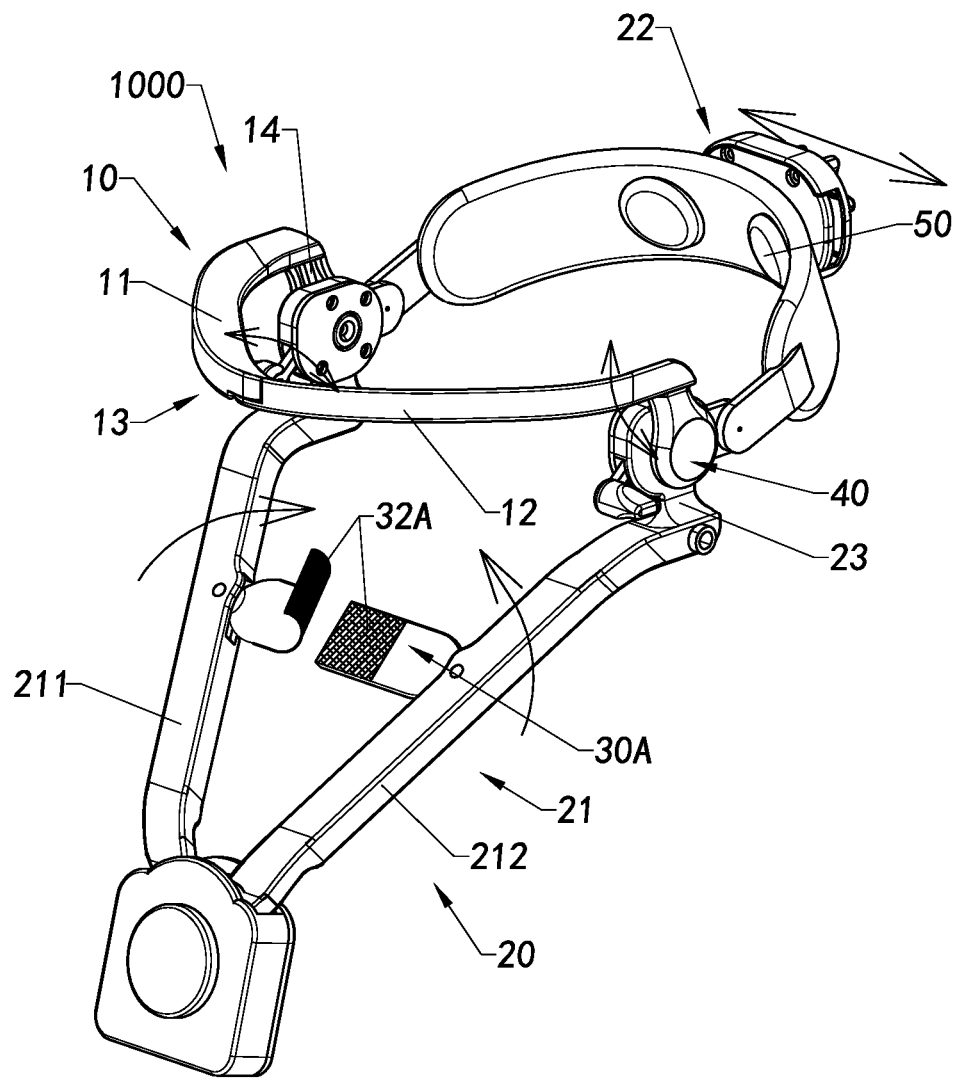
FIG. 11 is a perspective view illustrating the auxiliary support apparatus according to the above preferred embodiment of the present invention.

Referring to FIG. 11, another alternative mode of the auxiliary support apparatus 1000 according to the above preferred embodiments of the present invention is illustrated. The difference between this alternative mode and the above preferred embodiments is the adjustment unit 30A as described below.

According to this alternative mode, the adjustment unit 30A is implemented as loop and hook fasteners (Velcro). In particular, the adjustment unit 30A comprises two adjustment members 32A, one of which is a loop fastener connected to the first support arm 211, and the other adjustment members 32A is a hook fastener connected to the second support arm 212, such that one of the adjustment members 32A is detachably connected to the other adjustment members 32A.

It is worth mentioning that one of the adjustment members 32A can be repeatedly attached to the other adjustment member 32A in an attaching and affixing manner. If the relative position of the two adjustment members 32A is needed to be adjusted, two adjustment members 32A can be detached from each other and then reattached again to another appropriate position.

Furthermore, in such a connection manner, the first support arm 211 and the second support arm 212 can be adjusted in an asynchronous or asymmetrical manner. In particular, there is an intermediate axis between the first support arm 211 and the second support arm 212, and an angle between the first support arm 211 and the intermediate axis is equal to the angle between the second support the arm 212 and the intermediate axis. During the wearing process, the general intermediate axis is a symmetry axis of the human body. When the user finds that the angle between the first support arm 211 and the intermediate axis is greater than the angle between the second support arm 212 and the intermediate axis, the position of the wear body 21 on the user's trunk is skewed. The user can move the first support arm 211 toward the second support arm 212 to a position where the angles are the same. Then the adjustment member 32A corresponding to the first support arm 211 is fixed at a position corresponding to the adjustment member 32A of the second support arm 212, so as to fix the adjusted position.

Of course, the user can also adjust the position of the second support arm 212 during a single adjustment, maintaining the position of the first support arm 211 unchanged. The user can also change both the positions of the first support arm 211 and the second support arm 212 at the same time.

Figure 12:
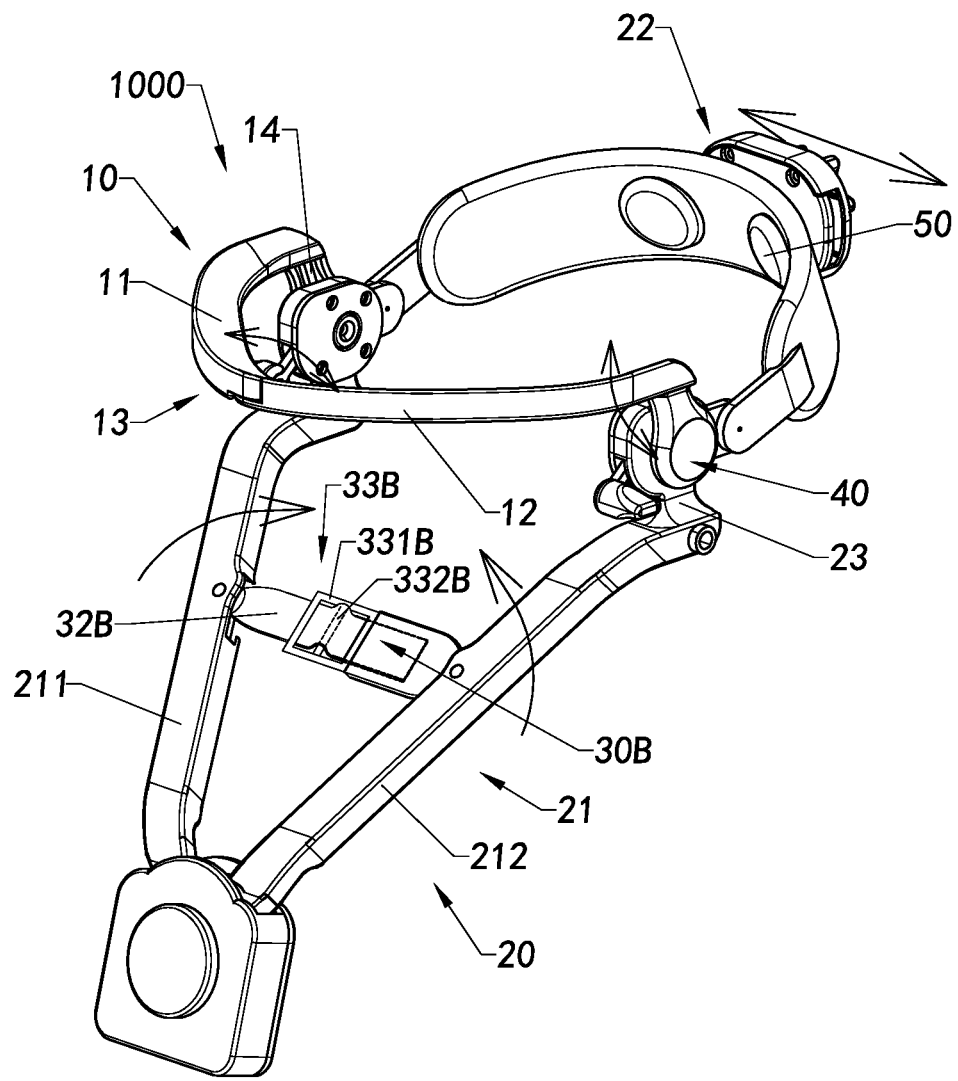
FIG. 12 is a perspective view illustrating the auxiliary support apparatus according to the above preferred embodiment of the present invention.

Referring to FIG. 12, another alternative mode of the auxiliary support apparatus 1000 according to the above embodiments of the present invention is illustrated. The difference from the alternative mode and the above embodiments is the adjustment unit 30B.

According to this alternative mode, the adjustment unit 30B has a buckle structure.

The adjustment unit 30B comprises an adjusting member 32B and a buckle 33B, wherein the adjusting member 32B is connected to the first support arm 211, and the buckle 33B is connected to the second support arm 212. The adjustment member 32B is detachably connected to the buckle 33B, and the length of part of the adjustment member 32B connected to the buckle 33B can be adjusted. The shorter the length of the part of the adjustment member 32B connected to the first support arm 211 and the buckle 33B, the smaller the angle between the first support arm 211 and the second support arm 212. The longer the length of the part of the adjustment member 32B connected to the first support arm 211 and the buckle 33B, the smaller the included angle between the first support arm 211 and the second support arm 212.

The user can adjust the included angle between the first support arm 211 and the second support arm 212 by adjusting the relative positions between the adjustment member 32B and the buckle 33B.

In particular, the buckle 33B comprises a buckle body 331B and a beam 332B, wherein the beam 332B spans the buckle body 331B. The buckle 33B has an entrance through hole and an exit through hole. The entrance through hole and the exit through hole are partitioned by the beam 332B. A free end of the adjustment member 32B first passes through the entrance through hole of the buckle 33B and then passes through the exit through hole bypass the cross member 332B. The adjustment member 32B can be fixedly connected to the buckle 33B via the frictional force among the adjustment member 32B and the beam 332B and the buckle 33B. When the user needs to adjust the length of the adjustment member 32B, the adjustment member 32B can be controlled to move away from the buckle 33B and then adjust the position of the adjustment member 32B.

Figure 13:
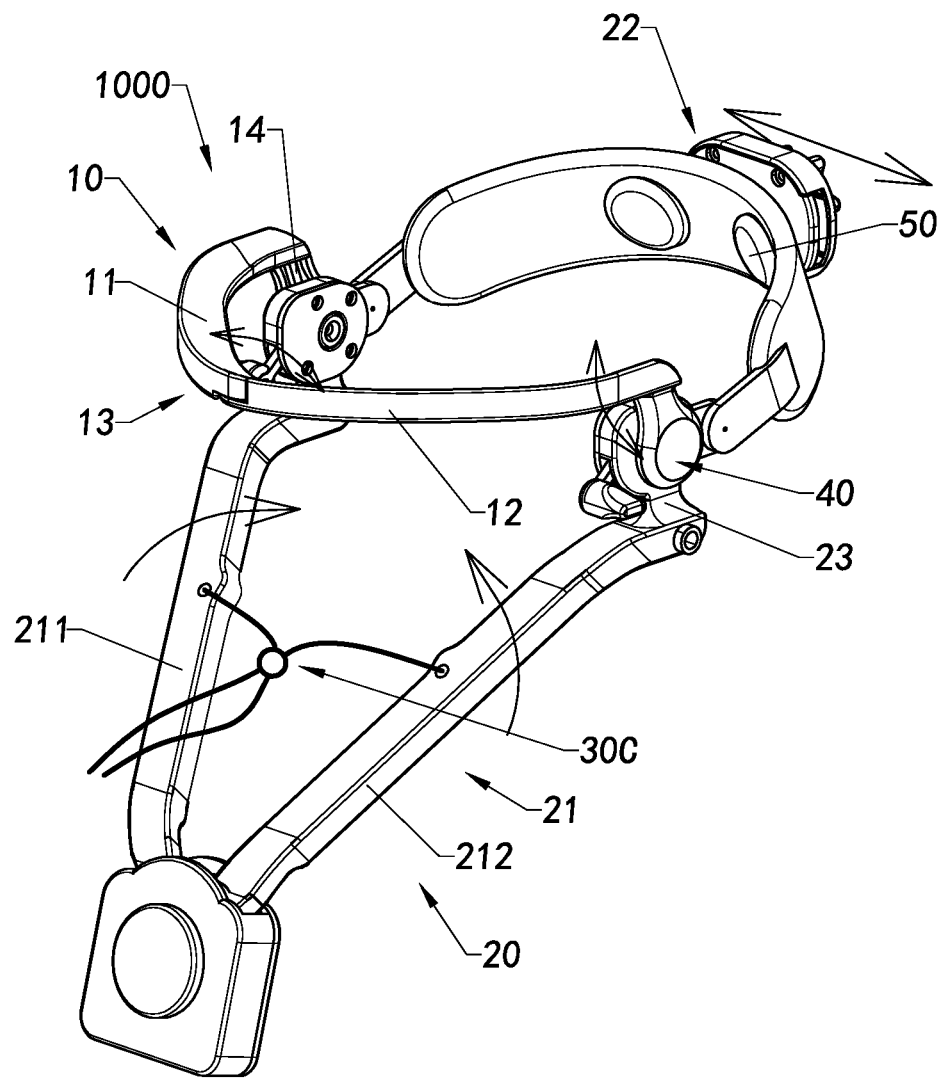
FIG. 13 is a perspective view illustrating the auxiliary support apparatus according to the above preferred embodiment of the present invention.
Figure 14:
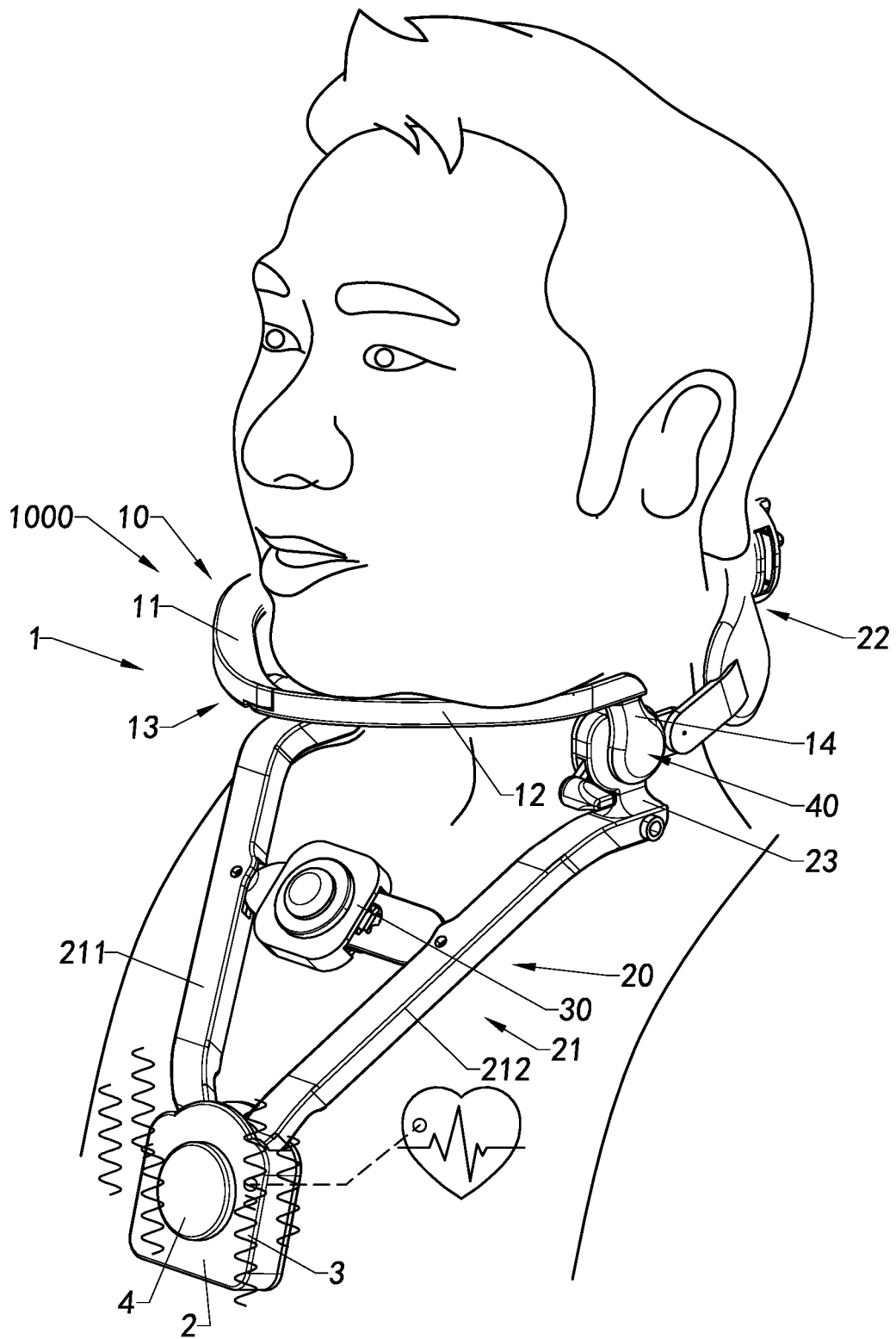
FIG. 14 is a schematic view illustrating an application of the auxiliary support apparatus according to the above preferred embodiment of the present invention.

Referring to FIG. 13, another alternative mode of the auxiliary support apparatus 1000 according to the above embodiments of the present invention is illustrated. The difference from this alternative mode and the above embodiment is the adjustment unit 30C.

According to this alternative mode, the adjustment unit 30C has a drawstring structure.

The adjustment unit 30C comprises two adjusting drawstrings and a drawstring locker, wherein the adjusting drawstrings are respectively connected to the first support arm 211 and the second support arm 212. The two adjusting drawstrings pass through the drawstring locker at the same time. The drawstring locker comprises a locker body and an operating button, and has a through hole, wherein the adjusting drawstrings can pass through the through hole, and the operating button is movably connected to the locker body, and the operating button can fix the adjusting drawstrings within the through hole, so as to avoid relative sliding between the drawstring locker and the adjusting drawstrings.

When the user needs to adjust the length of the adjusting drawstrings to change the relative positions of the first support arm 211 and the second support arm 212, he/she can operate the operating button, such as pressing the operating button to reduce the frictional force to the adjusting drawstrings, so that the adjusting drawstrings can move within the through hole. After the user moves the adjusting drawstrings to predetermined positions, he/she can release the operating button, then the adjusting drawstrings are fixed to the predetermined positions.

It is worth mentioning that the user can adjust the positions of the two adjusting drawstrings and the drawstring locker at the same time, and the positions of the two adjusting drawstrings and the drawstring locker can also be adjusted separately. In other words, the first support arm 211 and the second support arm 212 can be adjusted synchronously or separately.

Referring to FIG. 14 and FIG. 1 to FIG. 3C, the auxiliary support apparatus 1000 comprises an auxiliary support body 1, at least one detector 2, and a processor 3. The processor 3 and the detector 2 are respectively mounted in the auxiliary support body 1 of the auxiliary support apparatus 1000. The auxiliary support apparatus 1000 comprises the bearing member 10, the wear body 21 of the wear member 20, the auxiliary wear support member 22, and the fixing unit 40.

The detector 2 can be mounted to the bearing member 10, or can be mounted to the wear body 21 of the wear member 20, or can be mounted to the auxiliary wear support 22. In other words, the detector 2 can be mounted to at least one selected from the combination consisting of the bearing member 10, the wear body 21 of the wear member 20 and the auxiliary wear support 22. The detector 2 is used to detect the physical state of the user and transmit detection data to the processor 3. The processor 3 processes the detection data to determine whether the user has a health risk.

The detector 2 can be a pressure sensor. For example, when the detector 2 is mounted to the junction between the first support arm 211 and the second support arm 212 of the wear body 21 of the wear member 20, the detector 2 is directly contacted with the user's body and is capable of detecting the amount of force beared by the user's body. Once the magnitude of the force detected by the detector 2 over a period of time is hardly changed or the variation is within a certain range, the processor 3 will send an alarm signal, such as in a voice manner to prompt the user to change the posture in time.

The auxiliary support apparatus 1000 further comprises an alarm device 4. The alarm device 4 can be provided to the bearing member 10, the wear body 21 of the wear member 20, or the auxiliary wear support member 22, wherein the alarm device 4 is a vibration alarm 4. After receiving an alarm signal from the processor 3, the vibration alarm 4 will generate a vibration until the detected value of the pressure sensor changes.

The detector 2 can also be a frequency detector, wherein the frequency detector 2 can be used to detect a number of heart beats or an arterial beat frequency. For example, when the detector 2 is provided to the bearing member 10, it can be used to detect the frequency of the neck artery beat, and when the detector 2 is provided to the junction between the first support arm 211 and the second support arm 212 of the wear body 21 of the wear member 20, it can be used to detect the number of beats of the heart. Once the detector 2 detects that the frequency exceeds a predetermined value, the processor 3 will send an alarm signal to the alarm 4.

According to another aspect of the present invention, a working method for an auxiliary support apparatus 1000 is provided, wherein the working method comprises the following steps:
  receiving detection data from at least one detector 2 provided to an auxiliary support body 1; and
  sending an alarm signal by an alarm 4 provided to the auxiliary support body 1, in the case that the detected data exceeds a predetermined range.

According to another aspect of the present invention, a working method for an auxiliary support apparatus 1000 is provided, wherein the working method comprises the following steps:
  (a) receiving detection data from at least one detector 2 provided to an auxiliary support body 1;
  (b) generating a processing result, wherein the processing result is that the user maintains a fixed posture for more than a predetermined time range; and
  (c) sending an alarming signal to the detector 2, so as to detect a change in posture.

Figure 15:
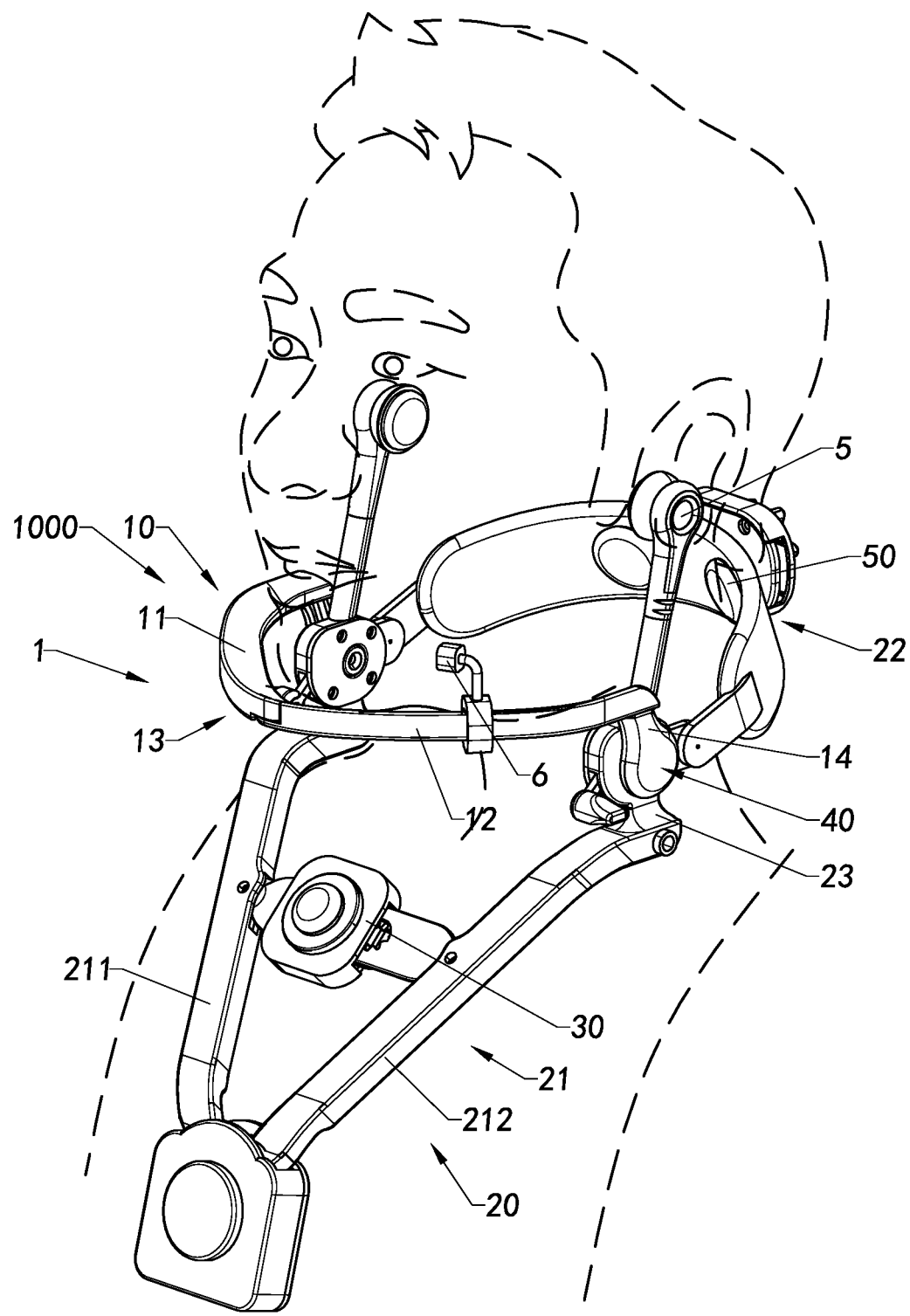
FIG. 15 is a schematic view illustrating an application of the auxiliary support apparatus according to the above preferred embodiment of the present invention.

According to one embodiment of the present invention, in the above method, the predetermined time is generated from a body health data of a user. Referring to FIG. 15 and FIG. 1 to FIG. 3C, the main difference between the embodiment as shown in FIG. 15 and the embodiment as shown in FIG. 1 to FIG. 3C is that the auxiliary support apparatus 1000 further comprises at least one broadcast unit 5. The auxiliary support apparatus 1000 comprises the auxiliary support body 1 and the broadcast unit 5. The broadcast unit 5 is mounted to the auxiliary support body 1.

The detector 2, the processor 3 and the broadcast unit 5 are mounted to the auxiliary support body 1. The auxiliary support body 1 comprises the bearing member 10 and the wear member 20, wherein the wear member 20 comprises the wear body 21 and the auxiliary wear support 22, wherein the auxiliary wear support 22 and the bearing member 10 form the wear passage. The bearing member 10 is used to support a head portion of a user. The wear body 21 of the wear member 20 is used to support the bearing member 10. The auxiliary wear support member 22 is used to lock the bearing member 10 to a neck of a user. The broadcasting unit 5 is used to play sound. The bearing member 10 is supported to the wear body 21 of the wear member 20. The auxiliary wear support 22 and the bearing member 10 define a wear passage 100. The broadcasting unit 5 is located near the user's ears, so that the user can receives the voice signal from the broadcast unit 5.

The auxiliary support body 1 has the wear passage 100 for enabling the auxiliary support body 1 to be worn on the user's head and neck, and supporting the user's head to the user's torso/trunk to reduce the stress to the neck or the cervical vertebra from the head. The broadcast unit 5 is arranged to be located near the ear of the user to enable the user to receive the voice signal of the broadcast unit 5. The broadcast unit 5 is capable of converting an electromagnetic signal from another electronic device or the internet into a sound signal, and the sound signal can only be received within a certain range from the broadcast unit 5, so that the user can enjoy the music played from the broadcasting unit 5 alone while the sound does not affect the surrounding environment.

The broadcast unit 5 supported to the auxiliary support body 1 is supported to the user's trunk via the auxiliary support body 1, so as to reduce the pressure to the head and neck from the broadcast unit 5.

In particular, the bearing member 10 and the auxiliary wear support 22 are worn on a user's head, and the bearing member 10 is capable of supporting a user's head on the wear body 21 of the wear member 20. At the same time, the wear body 21 of the wear member 20 is supported on the body part of the user. For example, according to this preferred embodiment of the present invention, the wear body 21 of the wear member 20 is supported on the front chest of the user, so as to reduce the pressure to neck of the user from the user's head and the broadcast unit 5.

The broadcast unit 5 is capable of transmitting information to the user in an audio manner to enable the user to acquire information by hearing. The auxiliary support apparatus 1000 further comprises the detector 2 and the processor 3, wherein the processor 3 and the detector 2 are respectively mounted to the auxiliary support body 1, and the detector 2 is communicated to the processor 3. The broadcast unit 5 is communicated to the processor 3. The processor 3 is communicated to the outside world to transmit outside information to the broadcast unit 5 and to transmit it to the user by voice. For example, playing music in a mobile phone or playing music directly on the Internet, or directly transmitting the voice information in the received chat record to the user, so that the user does not need to directly operate the interface of the related communication software.

It is worth mentioning that the processor 3 is also capable of transmitting non-speech information, such as a received mail into a voice through the broadcast unit 5 to the user. The processor 3 identifies the mail content, and then sends the content of the message to the user in a voice manner.

The broadcast unit 5 is mounted to the fixing unit 40. The fixing unit 40 is located at a joint between the bearing member 10 and the wear body 21 of the wear member 20. It is worth mentioning that, during the rotation of the bearing member 10 with respect to the wear body 21 of the wear member 20, the housing 43 of the fixing unit 40 is mounted to the end of the main body 21 of the wear member 20, and the housing 43 of the fixing unit 40 does not rotate with the rotation of the bearing member 10. The broadcast unit 5 is mounted to the fixing unit 40. Furthermore, the broadcast unit 5 is detachably mounted to the adjustment assembly, so that the broadcast unit 5 can be detached from the auxiliary support apparatus 1000 when the user does not need the broadcast unit 5.

The broadcast unit 5 is mounted to the housing 43 of the fixing unit 40, so that the broadcast unit 5 is not affected by the movement of the bearing member 10. In other words, the broadcast unit 5 is provided to extend upward from the housing 43 of the fixing unit 40, and the fixing unit 40 is located at the junction between the bearing member 10 and the wear body 21 of the wear member 20. When the position of the bearing member 10 is changed, the position of the broadcast unit 5 does not change along with the change of the position of the bearing member 10.

The housing 43 is provided inside the bearing member 10. The gear rotating shaft 41 is provided to extend inward from an end of the bearing member 10. The through hole 400 is formed to the housing 43. The broadcast unit 5 is arranged inside the bearing member 10 that the up and down movement of the bearing member 10 does not affect the broadcast unit 5.

It can be understood that, according to other embodiments of the present invention, the housing 43 is formed outside the bearing member 10, and the gear rotating shaft 41 is provided to extend outwards from the end of the bearing member 10. The through hole 400 is formed in the housing 43. The broadcast unit 5 is arranged outside the bearing member 10 that the up and down movement of the bearing member 10 does not affect the broadcast unit 5.

Furthermore, the broadcast unit 5 is rotatably connected to the housing 43 of the fixing unit 40 to facilitate adjustment to the position of the broadcast unit 5. The broadcast unit 5 is arranged to be stretchable to adjust the position of the broadcast unit 5 by changing the length of the broadcast unit 5.

The broadcast unit 5 can be a bone conduction earphone or a common air conduction earphone.

The auxiliary support apparatus 1000 further comprises a sound receiving unit 6, wherein the sound receiving unit 6 is mounted to the auxiliary support body 1 and is communicated to the processor 3. Via the radio unit 6, the user can control other devices or communicate with others in a voice manner. For example, the auxiliary support apparatus 1000 is used to accomplish the process of calling without actually placing the phone near the corresponding ear.

According to this embodiment of the present invention, the sound receiving unit 6 is mounted to the bearing member 10, and the sound receiving unit 6 is disposed to extend from a predetermined position of the bearing member 10 toward a user mouth position.

Furthermore, the sound receiving unit 6 is rotatably connected to the bearing member 10 to facilitate adjusting the position of the sound receiving unit 6. The sound receiving unit 6 itself is provided to be retractable to adjust the length. The sound receiving unit 6 is movably connected with the support portion 10 along the bearing member 10. The sound receiving unit 6 can be sleeved to the first bearing arm 11 or the second bearing arm 12 of the bearing member 10 by an annular elastic member. The elastic member has certain elasticity and can move along the first bearing arm 11 or the second bearing arm 12 under a proper force, and then is re-fixed at the support portion 10 by elasticity.

Compared with a conventional headset or a headphone with a microphone, the auxiliary support apparatus 1000 is capable of directly supporting the sound receiving unit 6 and the broadcast unit 5 to other parts of the user's body rather than the head or the neck, that relieves the pressure on the head and neck of the user in another aspect.

Figure 16:
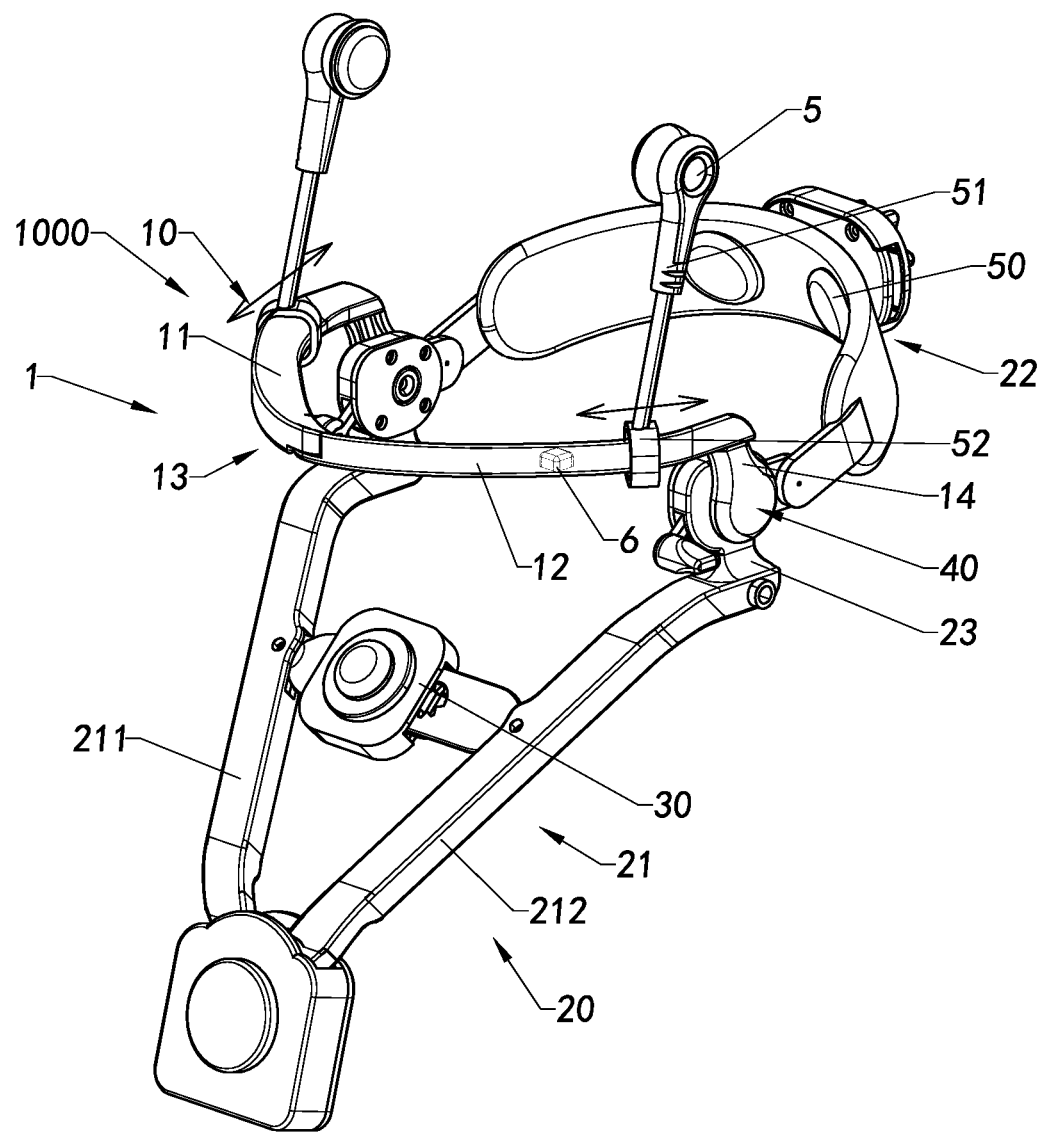
FIG. 16 is a perspective view illustrating the auxiliary support apparatus according to the above preferred embodiment of the present invention.

Referring to FIG. 16, another alternative mode of the auxiliary support apparatus 1000 according to the above embodiment of the present invention is illustrated.

The main difference between this alternative mode and the above embodiment is the broadcasting unit 5.

The broadcast unit 5 can be a bone conduction earphone or an air conduction earphone. According to this alternative mode, the broadcast unit 5 can be extended directly upward from the bearing member 10 to close to the ear of the user. Alternatively, the broadcast unit 5 is mounted to the first bearing arm 11 of the bearing member 10 or the second bearing arm 12 or is simultaneously mounted to both the first bearing arm 11 and the second bearing arm 12.

According to this alternative mode, the broadcast unit 5 is provided to close to the end of the bearing member 10, so as to be close to the user's ear position.

The broadcast unit 5 is mounted to the bearing member 10, and the broadcast unit 5 is detachably mounted to the bearing member 10 to facilitate a user to remove the broadcasting unit 5 when the broadcasting unit 5 is not required.

The number of the sounding units 5 can be one or two. In other words, the user may choose to install the broadcast unit 5 on the left side or the right side of the bearing member 10. Alternatively, the broadcasting unit 5 is mounted to both two sides of the bearing member 10 at the same time.

While the position of the bearing member 10 is changed, the position of the broadcast unit 5 also changes. Furthermore, the broadcast unit 5 is rotatably connected to the bearing member 10 so that while the position of the broadcasting unit 5 is changed, the relative position between the broadcasting unit 5 and the user's ear is adjusted by rotating the bearing member 10, so that the broadcasting unit 5 provides a broadcasting with better quality near the user's ears.

Furthermore, the broadcast unit 5 is arranged to be extensible and retractable, so as to facilitate the adjustment of the relative position between the broadcast unit 5 and the user's ears, so as to provide a large degree of adjustment freedom.

Furthermore, the broadcast unit 5 comprises a sounding body 51 and an elastic connector 52, wherein one end of the elastic connector 52 is connected to the sounding body 51, and the other end is connected to the bearing member 10. The elastic connector 52 is an annular connector according to this alternative mode. The elastic connector 52 is movably connected to the bearing member 10 along the first bearing arm 11 or the second bearing arm 12, so that the position of the sounding body 51 can be changed via the movement of the elastic connector 52.

The elastic connector 52 can be an annular connecting member or a C-shaped connecting member to facilitate the disassembly and installation of the elastic connector 52. The sounding body 51 is rotatably connected to the elastic connector 52.

The auxiliary support apparatus 1000 further comprises at least one sound receiving unit 6, wherein the sound receiving unit 6 is formed at a position close to the mouth of the user. In particular, the sound receiving unit 6 is mounted to the first bearing arm 11 or the second bearing arm 12 or both the first bearing arm 11 and the second bearing arm 12 of the bearing member 10. Furthermore, the sound receiving unit 6 is embedded in the bearing member 10, so that the user cannot observe the structure of the sound receiving unit 6 on the outside, so as to improve the aesthetic appearance of the entire auxiliary support apparatus 1000. Alternatively, the sound receiving unit 6 is mounted on the first bearing arm 11 or the second bearing arm 12 of the bearing member 10 or both the first bearing arm 11 and the second bearing arm 12.

The sound receiving unit 6 rotates along with the rotating of the bearing member 10, so that the sound receiving unit 6 has a good sound effect at any time.

According to other alternative modes of the present invention, the sound receiving unit 6 is formed to extend outwardly from the end of the bearing member 10, and the sound receiving position of the sound receiving unit 6 is located near the user's mouth. The sound receiving unit 6 is rotatably connected to the bearing member 10 to facilitate the adjustment of the relative positions between the sound receiving unit 6 and the user's mouth for obtaining a better sound quality.

It can be understood that the broadcast unit 5 can be not only a bone conduction earphone but also a general air conduction earphone.

If the broadcast unit 5 is an air conducting earphone, the broadcast unit 5 can be received in the housing 43 of the fixing unit 40 to facilitate convenient use and storage of the broadcast unit 5.

Figure 17A:
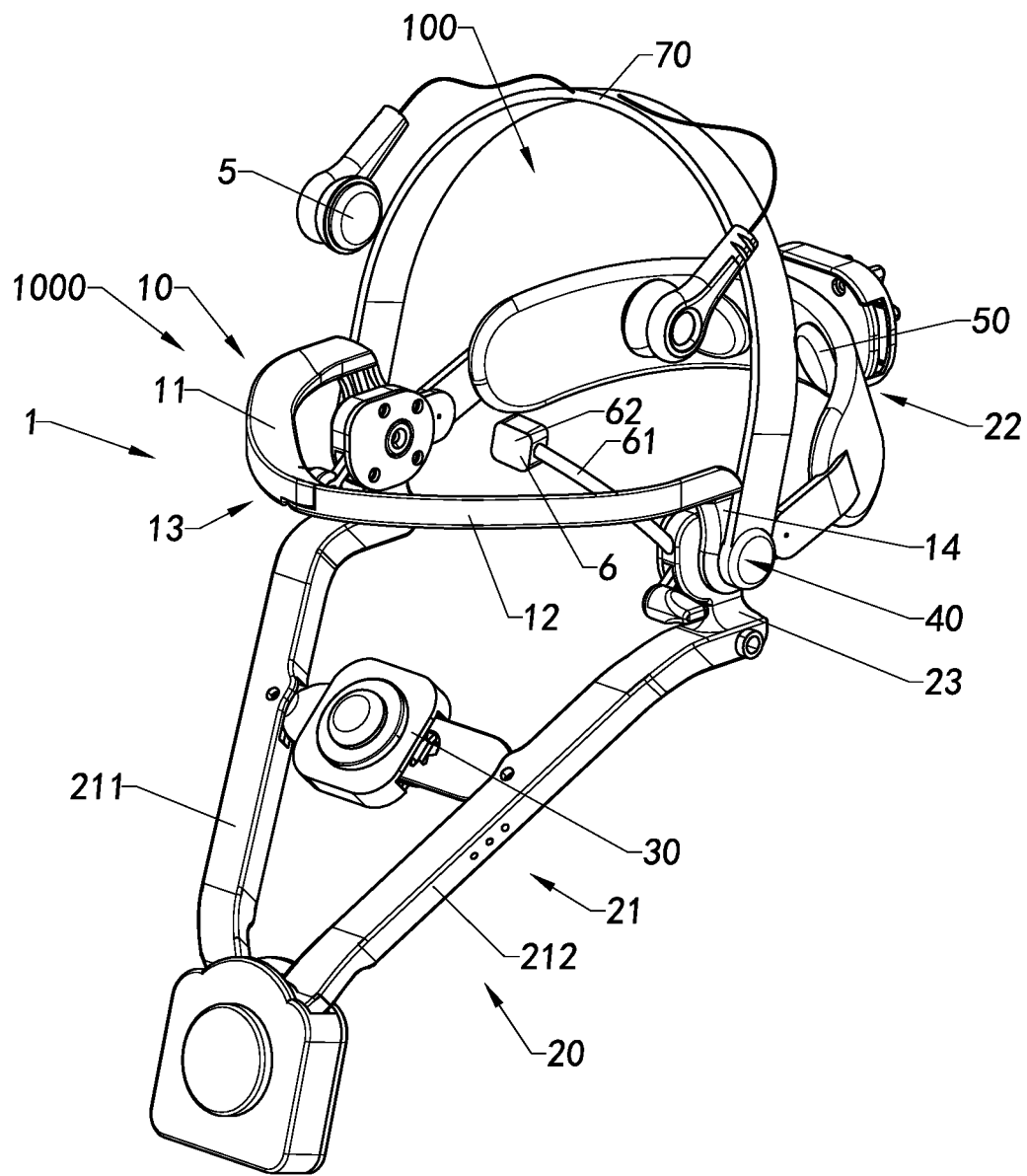
FIG. 17A is a perspective view illustrating the auxiliary support apparatus according to the above preferred embodiment of the present invention.

Referring to FIG. 17A, the auxiliary support apparatus 1000 further comprises a support frame 70 provided and extended across the wear passage 100 and is configured to be rotatable. According to this embodiment, the support frame 70 is rotatably connected to the wear body 21 of the wear member 20. The broadcast unit 5 is mounted to the support frame 70. The sound receiving unit 6 is mounted to the bearing member 10. In other words, the broadcast unit 5 and the support frame 70 can be independently adjusted.

Alternatively, the support frame 70 is provided to be extensible and retractable, so that the support frame 70 is correspondingly adjusted while the sizes of the wear passage 100 changes.

Alternatively, the support frame 70 is detachably connected to the auxiliary support body 1, so that the user can directly remove the support frame 70 when the support frame 70 is not required to be used.

The broadcast unit 5 is mounted to the support frame 70. According to this embodiment, the broadcast unit 5 is an air-conducting earphone connected to the support frame 70 through a connecting line. The connector has a certain length to suit different wearers.

The sound receiving unit 6 is mounted to the fixing unit 40, and the sound receiving unit 6 is extended from the fixing unit 40 toward the user's mouth. The sound receiving unit 6 is rotatably connected to the bearing member 10 to facilitate adjustment to the relative positions between the sound receiving unit 6 and the user's mouth.

Furthermore, the sound receiving unit 6 comprises an extending arm 61 and a sound bearing member 62, wherein one end of the extending arm 61 is connected to the fixing unit 40, and the other end of the extending arm 61 is connected to the sound bearing member 62. The sound bearing member 62 is located near the mouth of the user to facilitate sound receiving.

The extension arm 61 is provided to be stretchable to facilitate adjustment to the position of the sound bearing member 62.

Figure 17B:
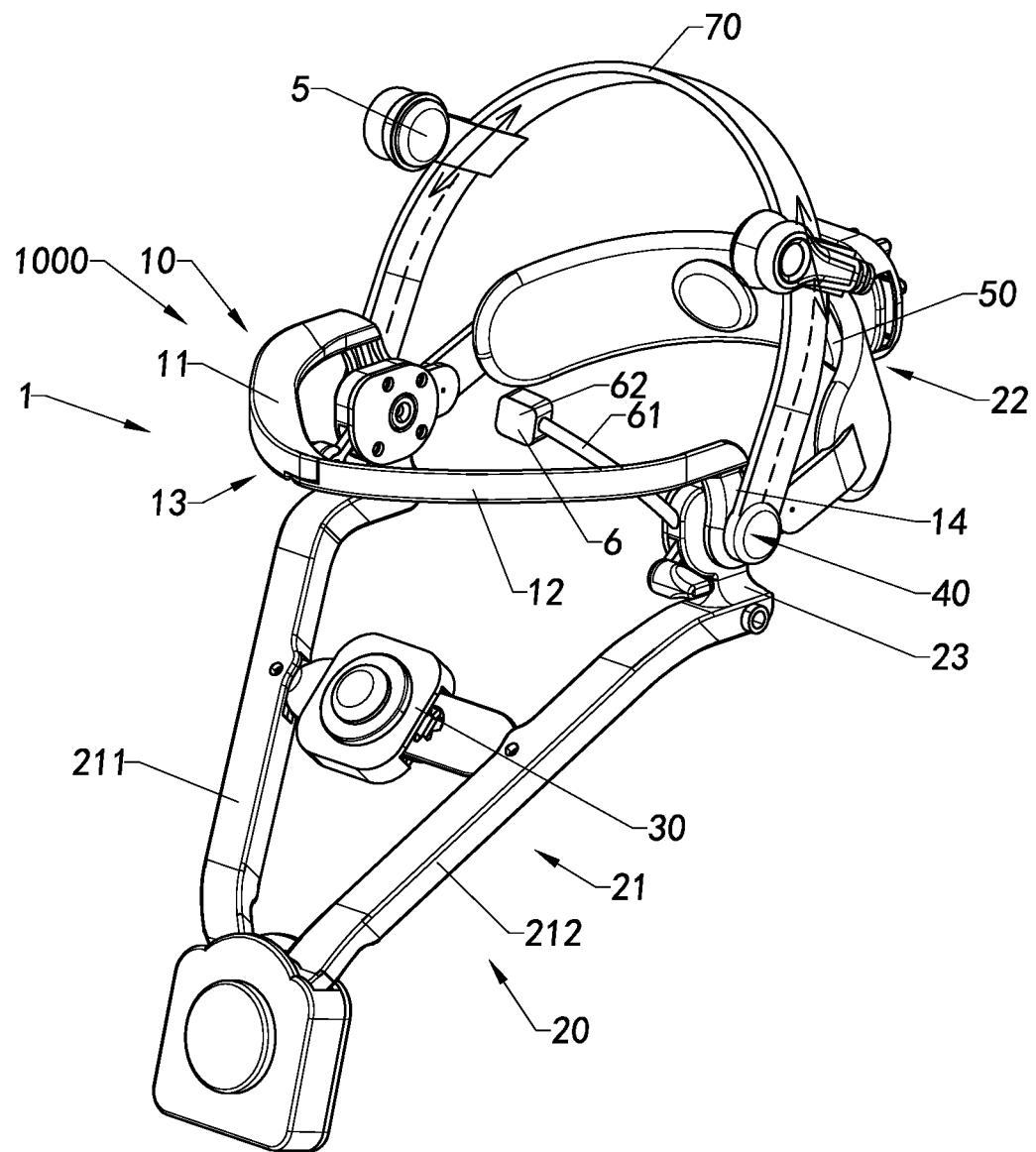
FIG. 17B is a perspective view illustrating the auxiliary support apparatus according to the above preferred embodiment of the present invention.

Referring to FIG. 17B, according to this embodiment, the broadcast unit 5 is embodied as a bone conduction earphone and is downwardly extendedly from the support frame 70. The broadcast unit 5 is rotatably connected to the support skeleton 70. The broadcast unit 5 itself is provided to be extensible and retraction.

Figure 18:
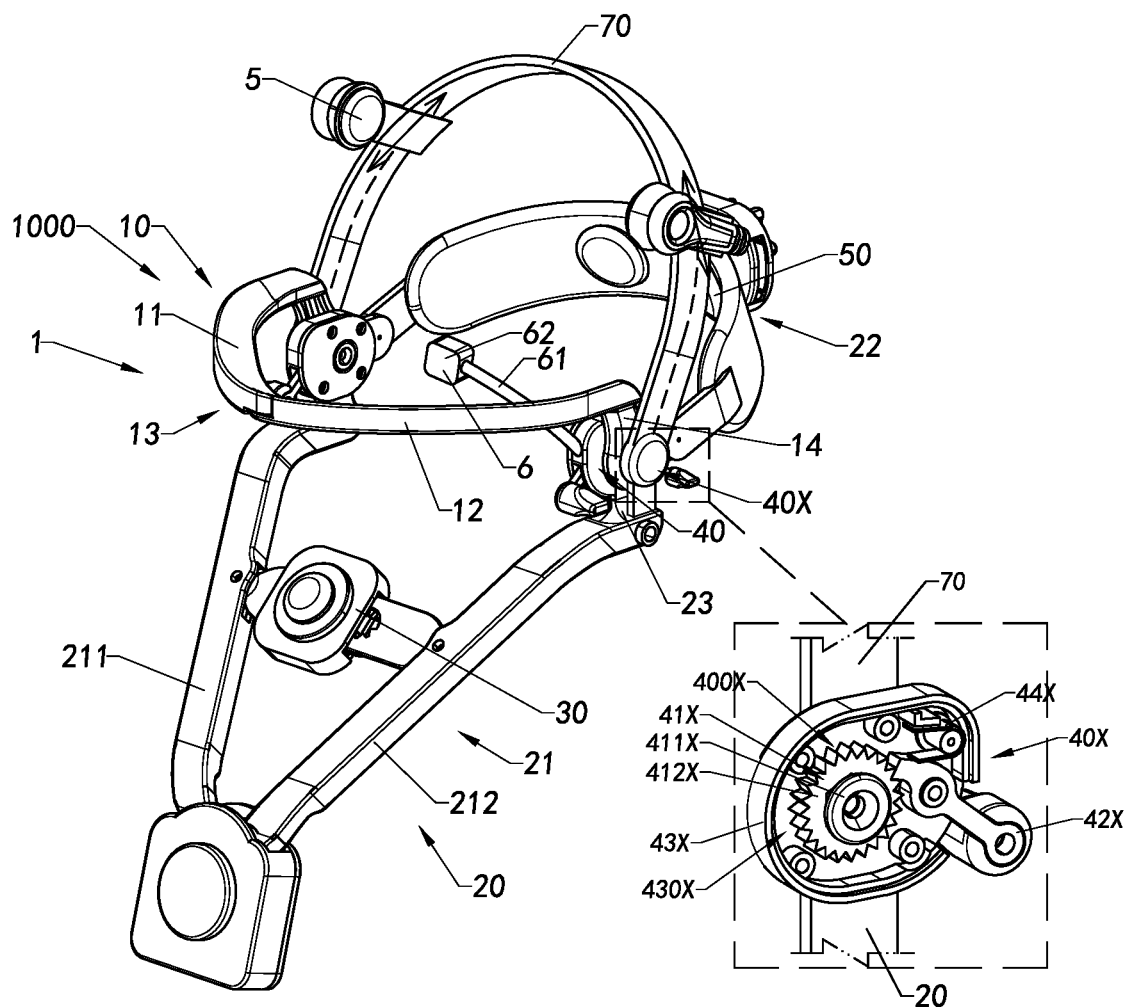
FIG. 18 is a schematic view illustrating the auxiliary support apparatus according to the above preferred embodiment of the present invention.

Referring to FIG. 18, the difference between this alternative mode and the above embodiment a shown in FIG. 17B is that the auxiliary support apparatus 1000 further comprises a fixing unit 40X, wherein the fixing unit 40X is provided to the junction between the wear body 21 of the wear member 20 and the support frame 70. Via the fixing unit 40X, a support angle between the support frame 70 and the wear body 21 of the wear member 20 can be adjusted and can be fixed at a fixed angle.

The fixing unit 40X comprises a housing 43X, a gear rotating shaft 41X and a lever 42X, and has a through hole 400X, wherein the gear rotating shaft 41X is received in the housing 43X, and the through hole 400X is formed to the housing 43X. The housing 43X is formed on the support frame 70 or the wear body 21 of the wear member 20. When the housing 43X is formed on the support frame 70, the gear rotating shaft 41X is formed on the wear body 21 of the wear member 20. When the housing 43X is formed on the wear body 21 of the wear member 20, the gear rotating shaft 41X is formed on the supporting frame 70.

The lever 42X prevents the gear rotating shaft 41X from rotating in one direction, so that the gear rotating shaft 41X can only move in one direction, so that the support frame 70 can be adjusted only in one direction. The lever 42X has a supporting state and an unsupporting state. In the supporting state, the lever 42X is supported by the gear rotating shaft 41X, and the gear rotating shaft 41X can only rotate in a clockwise or counterclockwise direction. In the unsupporting state, the lever 42X does contact with the gear rotating shaft 41X, so that the lever 42X can be arbitrarily rotated clockwise or counterclockwise.

According to some embodiments of the invention, the fixing unit 40X is positioned at the junction between the bearing member 10 and the support frame 70. According to some embodiments of the present invention, the fixing unit 40X is positioned at the junction among the bearing member 10, the wear body 21 of the wear member 20, and the support frame 70.

Figure 19:
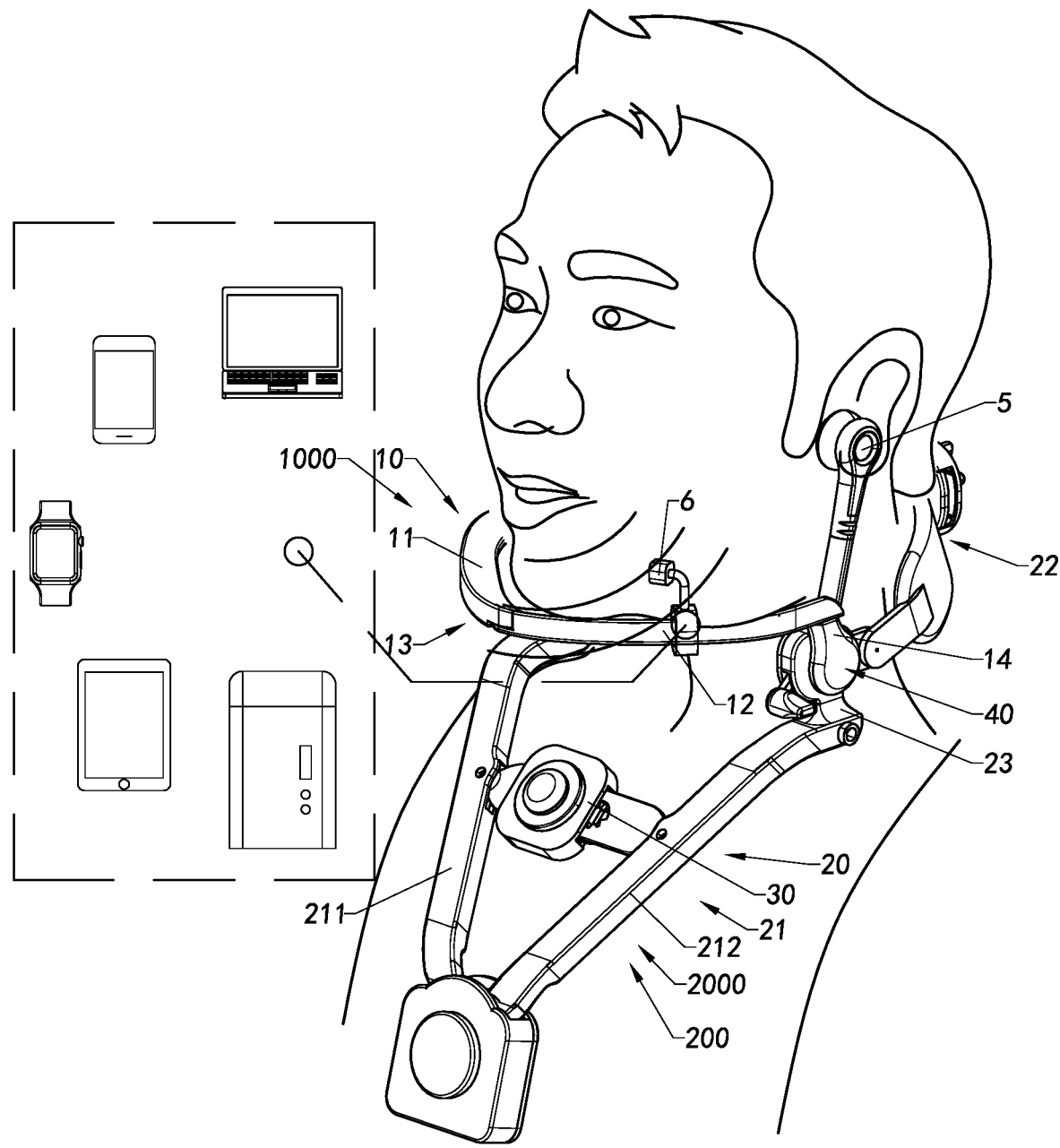
FIG. 19 is a schematic view illustrating an application of the auxiliary support apparatus according to the above preferred embodiment of the present invention.

Referring to FIG. 19 and referencing FIGS. 1~3C, in accordance with another aspect of the present invention, an auxiliary support system 200 is provided, wherein the auxiliary support system 200 comprises at least one auxiliary support apparatus 1000 and an assistant system 2000. The assistant system 2000 is communicatively linked to the auxiliary support apparatus 1000.

It is worth mentioning that, through the assistant system 2000, other smart devices at the user's location can be linked and controlled. With the popularity of intelligent homes and the pursuit to comfortable living, many smart home devices are installed indoors, and these smart home devices can be controlled through simple operations such as voice control. The problem, however, is that the smart home device cannot accurately implement the user's command when the distance between the user's location and the smart home device is relatively long. Via the assistant system 2000, the smart home device is capable of accurately receiving a voice command from a user at a greater distance.

In detail, the assistant system 2000 comprises a receiving module, a processing module, and an output module, wherein the receiving module 2010 is used to receive user voice input, and the processing module is communicated to the receiving module and the output module. The processing module generates a processing result according to the user voice input received by the receiving module, and the output module outputs the result to the user according to the processing result. The receiving module is integrated or partially integrated to the sounding unit 6. The output module is integrated or partially integrated in the broadcast unit 5. The auxiliary support apparatus 1000 further comprises the processor 3, wherein the processing module is integrated or partially integrated in the processor 3. Alternatively, the processor 3 is provided at a connection position between the first support arm 211 and the second support arm 212 of the wear body 21 of the wear member 20.

The receiving module can be provided to receive a user voice in a manner of identifying a specific user voice input, such as when the smart home device is located in a public space but the ownership of the smart home device belongs to an individual, or when a company employee purchases a smart home device places it at its own workstation, the receiving module can be set to receive only voice input from the owner.

The receiving module can also be provided to identify user voice input within a certain range. In other words, when the user is within a certain range from the smart home device, the receiving module can receive the voice input of the user. Because in some cases, the user does not want the smart home device to receive his or her own voice at all times to avoid disclosure of his privacy.

Furthermore, the processing module comprises an identification module and a generation module, wherein the identification module is communicated to the receiving module and the generation module. The identification module 2040 identifies the user voice input accepted by the receiving module, so as to obtain a recognition result. The generation module generates a processing result according to the recognition result and sends the processing result to the output module. The output module 2030 outputs outward according to the processing result.

For example, the receiving module receives a user voice input, and the identification module identifies the user voice input to obtain a recognition result "air conditioning temperature degree". The generation module generates an answer based on the recognition result, such as "OK". The output module outputs outward according to the processing result. It can be understood that the output module outputs outward according to the current output mode. The output mode can be selected from one or more selected from a sound output, a synthesized speech output, and a sampled speech output.

The identification module may obtain a recognition result by converting the voice into text. The identification module may also compare an audio input directly by the user voice with a historical data to obtain a recognition result.

The identification module further comprises a parsing module, a judging module and a task identifying module, wherein the parsing module is communicatively linked to the receiving module. The judging module is communicatively linked to the parsing module and the task identification module. The task identification module is communicatively linked to the generation module. The parsing module parses the user voice input to obtain an analysis result and sends the parsing result to the judging module. The judging module determines whether the parsing result comprises at least one representation about intent of the user. If The result of the determination is affirmative, the task identification module identifies a task according to the representation about the user's intention, and the generation module generates a processing result about invoking at least one service of the task. The output module 2030 outputs the processing result externally.

For example, the receiving module receives a user voice input, and the parsing module parses the user voice input to obtain an analysis result "coming music". The judgment result obtained by the judging module is the parsing result comprises a representation about the user's intention. According to the parsing result, the task identification module identifies a task that the user needs a piece of music. The generation module confirms that a music service needs to be called according to the task and a process result that calling a music service needs to be generated, and the music is outputted outward via the output module. Alternatively, the output module first outputs a processing result regarding calling a service for executing the task, and then calling the service.

It can be understood that the service can be built in the auxiliary support apparatus 1000 or can be acquired through the Internet. In other words, according to one embodiment of the present invention, the assistant system 2000 comprises a service module, wherein the service module is used to provide at least one service, wherein the service module is communicatively linked to the processing module, so as to be called according to the user voice input.

Furthermore, the assistant system 2000 comprises an active lead-out module, wherein the active lead-out module is communicated to the processing module and the output module. When the identification module cannot identify the user voice input to obtain a task, the active lead-out module generates at least one prompt for actively extracting input from a user according to the user voice input, and the output module outputs the prompt.

For example, the receiving module receives a user voice input, and the identification module only identifies at least one representation "which support angle is good" in the user voice input, which comprises the user's intention. The processing module cannot obtain a task because the support angle is between which objects is not known. The active lead-out module is invoked, and the active lead-out module generates at least one prompt "which support angle is it" for actively extracting input from the user according to the user voice input "which support angle is good". Via the output module, the prompt is delivered to the user, and the task is confirmed based on the user's second voice input.

It can be understood that the identification module acquires data according to a context that the receiving module has received. For example, according to context data that the receiving module has received, the previous user voice input comprises "head and neck", the identification module can identify the representation about the user's intent to get a task.

The generation module may find an answer to the task via the data that has been stored or through the Internet search and pass the answer to the user through the output module.

Furthermore, according to this preferred embodiment of the present invention, the assistant system 2000 comprises an interpretation module, wherein the interpretation module is communicatively linked to the receiving module and the processing module. The interpretation module is used to interpret the user voice input received by the receiving module. When the processing module is unable to obtain an accurate result by using the user voice input received by the receiving module, the interpretation module performs an interpretation according to the user voice input, and outputs the interpretation through the output module, so as to confirm a task.

Specifically, the parsing module performs an analysis on the user voice input from the receiving module to obtain an analysis result. The judging module judges that the user voice input comprises at least one representation about the user's intention. However, the task identification module is unable to identify a task based on the representation regarding the user's intent. The interpretation module performing an interpretation based on the representation of the user's intent to derive an interpretation result and transmitting the interpretation result to the output module. The output module outputs the interpretation result based on a current output module, so as to clarify a user's intention in the subsequent operation to confirm an operation that the smart home device needs to complete.

For example, the receiving module receives a user voice input, and the parsing module parses the user voice input to obtain an analysis result, which is "start work", and the judging module judges that the parsing result comprises at least one representation about the intent of the user, but the task identification module is unable to recognize that the task is "which smart home device is needed to start work".

The interpretation module interprets the representation of the user intent to obtain an interpretation result "What is needed to start working". The output module outputs the interpretation result to confirm to the user.

Furthermore, the assistant system 2000 comprises a storage module, wherein the storage module comprises a short-term storage module and a long-term storage module, and the storage module is communicated to the processing module. The storage module is used to store data including not only user interaction data but also historical data. Furthermore, the storage module comprises a short-term storage module, wherein the short-term storage module is used to store at least one user interaction data about the smart home device. The short-term storage module is communicated to the receiving module, the processing module, the active boot module, the paraphrase module, and the output module. The storage module comprises a long-term storage module, wherein the long-term storage module is used to store one or more types of information selected from personal information associated with a user, collected information according to the user, and saved transaction information related to the user. It can be understood that the data type stored by the storage module is not limited to the data type described above. It can be understood that, by real-time data and historical data stored by the storage module, the accuracy of the processing module in identifying the voice input of the user will be correspondingly improved. For example, historical data can be used to identify tasks corresponding to a certain keyword.

For example, the receiving module receives a user voice input, and the user voice input comprises an audio signal "sidu". The identification module communicated to the storage module recognizes that the meaning represented by the audio signal is "humidity", because the user is a child, and the pronunciation is not standard. The processing module confirms a task, namely providing user humidity information, according to the user voice input. A task module is called to obtain humidity information, and the output module inputs the humidity information.

Through the real-time data stored by the storage module, the accuracy of the processing module in identifying the task will also be correspondingly improved. For example, the receiving module receives the user voice input, and the user voice input comprises "wind speed becomes bigger." The identification module cannot identify a task according to the user voice input, but through the context of the user interaction data stored by the storage module, the identification module can confirm that a task "the air conditioning wind speed starts to become large". The context data can be obtained by data received by the receiving module and then stored in the storage module.

At least one of the processing module, the active egress module and the paraphrase module obtains parameters from a received context of the receiving module.

The context that the receiving module has received is one or more selected from a combination group consisting of the current software application, the current state, the current location, the current environment adjustment detected by at least one environment detector, the usage history, and the information describing the user.

Furthermore, the processing module comprises an execution module, wherein the execution module executes the processing result of invoking a service of the service module to perform a task to cause the service to be invoked. The execution module is communicated to the generation module and the service module.

It is worth mentioning that the auxiliary support apparatus 1000 can not only make a matching response to the user voice input, but also can actively output to the user to play a prompting role.

The auxiliary support apparatus 1000 can assist the user in communicating with others so that the user does not need to use additional communication devices.

The receiving module is communicated to a user's personal mobile device or office communication device, such as a personal work computer or a mobile phone. The receiving module receives some communication information, such as an incoming call, from the communication software. The processing module processes the communication information received by the receiving module, such as identifying text information and converting the text information into a voice information, so as to output to the user in a voice manner in the subsequent steps. In this manner, the user does not need to personally control the personal mobile device or the office communication device, and can directly obtain information from the external device. It can be understood that the information collected by the receiving module is not limited to the communication information from the communication software, and may also be other information that requires user processing and to feedback.

Furthermore, through the radio unit 6, the receiving module of the assistant system 2000 receives feedback from a user. The processing module processes the feedback of the user, so as to output in certain output mode via the output module in the subsequent step. For example, the communication information initially received is text information, then the assistant system 2000 can convert the communication information into text information and then output.

In other words, when the auxiliary support apparatus 1000 is worn by the user, the user directly issues a voice command to activate the external device via the assistant system 2000 to process the transaction.

Figure 20:
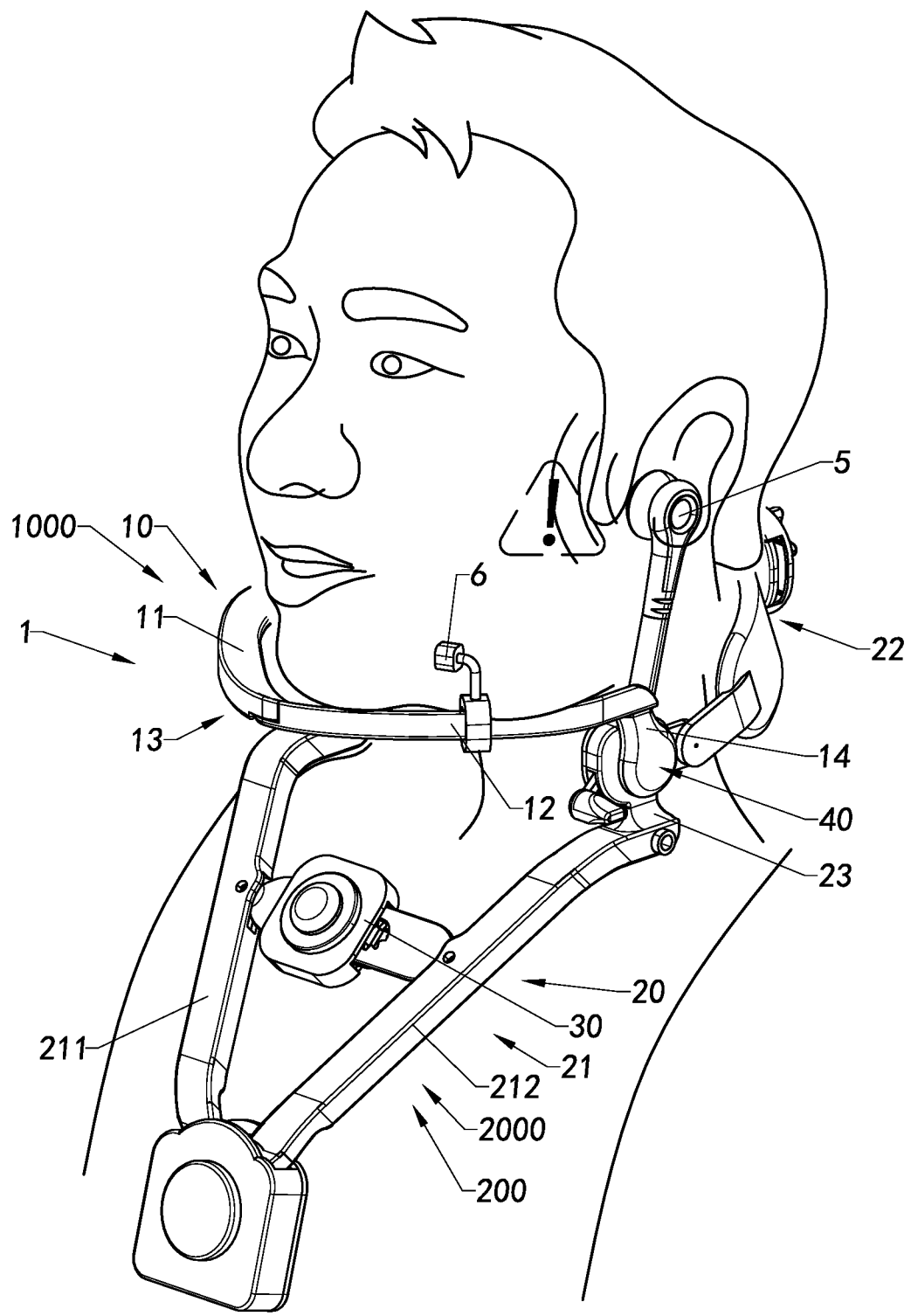
FIG. 20 is a schematic view illustrating an application of the auxiliary support apparatus according to the above preferred embodiment of the present invention.

Referring to FIG. 20 and referencing to FIGS. 1~3C, an application scenario of an auxiliary support apparatus 1000 according to a preferred embodiment of the present invention is illustrated.

The auxiliary support apparatus 1000 further comprises the detector 2, wherein the detector 2, the sound receiving unit 6 and the broadcast unit 5 are communicatively linked to the processor 3.

The detector 2 can be mounted to the bearing member 10, or can be mounted to the wear body 21 of the wear member 20, or can be mounted to the auxiliary wear support 22. In other words, the detector 2 can be mounted to at least one selected from the bearing member 10, the wear body 21 of the wear member 20 and the auxiliary wear support 22. The detector 2 is used to detect the physical state of the user and to transmit detection data to the processor 3. The processor 3 processes the detection data to determine whether the user has a health risk.

The detector 2 can be a pressure sensor. For example, when the detector 2 is provided to the junction of the first support arm 211 and the second support arm 212 of the wear body 21 of the wear member 20, the detector 2 is directly contacted to the user's body and is capable of detecting the amount of force experienced by the user's body. Once the magnitude of the force detected by the detector 2 over a period of time is hardly changed or the variation is within a certain range, the processor 3 will send an alarm signal to the broadcast unit 5, and the broadcast unit 5 prompted the user to change the posture in time in a voice manner.

Furthermore, the processor 3 can generate a reminder time according to a user health data detected by the detector 2, and then the detector 2 detects that the user maintains a fixed posture within the reminding time. Once the reminder time is exceeded the processor 3 will issue an alarm message. For example, the processor 3 generates a reminder time of 10 minutes according to the user health data detected by the detector 2. Due to the user's heart rate is fast, maintaining a posture for a long time can be detrimental to the user's physical health. Therefore, the reminder time is shorter. After the user has held a fixed posture for more than 10 minutes, the processor 3 sends an alarm message to the detector 2 detecting a change in the user's posture.

It is worth mentioning that once an alarm signal is sent, if the detector 2 does not detect a change in the posture of the user, the strength of the alarm signal will be progressively enhanced, so that the user can be reminded in time on the one hand, and that the alarm signal is set to be step-by-step enhanced to avoid causing excessive influence on the user while playing a prompt role on the other hand. When the user maintains a fixed posture during the work or learning process, he/she is likely to concentrate on thinking. Once the initial reminder intensity is too large, it may affect the user's thinking, and even interrupt the user's thinking, which causes the user's dislike.

The auxiliary support apparatus 1000 further comprises an alarm device 4. The alarm device 4 can be mounted to the bearing member 10, the wear body 21 of the wear member 20, or the auxiliary wear support member 22, wherein the alarm 4 is a vibration alarm 4. After receiving an alarm signal from the broadcast unit 5, the vibration alarm 4 will generate a vibration until the detected value of the pressure sensor changes.

The detector 2 can also be a frequency detector 2, wherein the frequency detector 2 can be used to detect a heart rate or an arterial pulsation frequency. For example, when the detector 2 is mounted to the bearing member 10, it can be used to detect the frequency of the neck artery beat frequency. When the detector 2 is mounted to the junction between the first support arm 211 and the second support arm 212 of the wear body 21 of the wear member 20, it can be used to detect the heart rate. Once the detector 2 detects that the frequency exceeds a predetermined value, the processor 3 will send an alarm signal to the broadcast unit 5 or the alarm 4. According to another aspect of the present invention, a working method for an auxiliary support apparatus 1000 is provided, wherein the working method comprises the following steps:
  (a) receiving a detection data of at least one detector 2 provided to an auxiliary support body 1; and
  (b) sending out an alarm signal while the detection data exceeds a predetermined range.

According to one embodiment of the present invention, in the step (b), at least one broadcasting unit 5 mounted to the auxiliary support body 1 sends out the alarm signal.

According to one embodiment of the present invention, in the working method, the auxiliary support body 1 comprises a bearing member 10 and a wear member 20, and the wear member 20 comprises a wear body 21 and an auxiliary wear support member 22. The bearing member 10 is used to supporting a head portion. The bearing member 10 and the wear body 21 of the wear member 20 form a triangular configuration, wherein the detector 2 is mounted to a lower end of the wear body 21 of the wear member 20.

According to one embodiment of the present invention, in the working method, the auxiliary support body 1 comprises a bearing member 10 and a wear member 20, and the wear member 20 comprises a wear body 21 and an auxiliary wear support member 22. The bearing member 10 is used to supporting a head portion. The bearing member 10 and the wear body 21 of the wear member 20 form a triangular structure, wherein the detector 2 is mounted to the bearing member 10.

According to another aspect of the present invention, a working method for an auxiliary support apparatus 1000 is provided, wherein the working method comprises the following steps:
  (a) receiving a detection data of at least one detector 2 provided to an auxiliary support body 1; and
  (b) sending out an alarm signal when the detection data proof the user maintains a fixed posture for a predetermined time.

According to one embodiment of the present invention, in the working method, the predetermined time is generated according to the user physical health data detected by the detector 2.

According to another aspect of the present invention, a working method for an auxiliary support apparatus 1000 is provided, wherein the working method comprises the following steps:
  receiving a voice command from a user via a sound receiving unit 6 provided to an auxiliary support body 1, wherein the voice command is related to controlling at least one smart device;
  identifying the voice command to generate a task; and
  sending the task to the corresponding smart device to cause the task to be executed.

According to another aspect of the present invention, a working method for an auxiliary support apparatus 1000 is provided, wherein the working method comprises the following steps:
  receiving a communication message for the user;
  transmitting the communication information via a sound unit 5 of the auxiliary support apparatus 1000; and
  receiving an answer corresponding to the communication information via a sound receiving unit 6 of the auxiliary support apparatus 1000.

According to another aspect of the present invention, a manufacturing method for an auxiliary support apparatus, wherein the manufacturing method comprises the following steps:
  (a) maintaining a support portion to a wear body; and
  (b) forming a support angle between the bearing member and the wear body in such a manner that the support angle is adjustable and the supported angle can be fixed after being adjusted.

According to one embodiment of the present invention, the above manufacturing method further comprises a step of:
  providing an auxiliary wear support 22 to form a wear passage between the auxiliary support 22 and the bearing member.

According to one embodiment of the present invention, in the above method, the bearing member is held to the wear body obliquely upwards with respect to the horizontal plane.

According to one embodiment of the present invention, the step (a) further comprises:
  forming two first support legs respectively at two ends of a supporting body;
  forming two second support legs respectively at two ends of a wear body; and
  forming a fixing unit rotatably and fixedly connected to the first support leg and the second support leg is formed.

According to another aspect of the present invention, a support method for supporting a head to a trunk portion via an auxiliary support apparatus is provided, wherein the support method comprises the following steps:

supporting a wear body to the trunk; and supporting the bearing member to the head in such a manner that the relative position between the wear body and a bearing member is adjustable, while the bearing member is supported by the wear body.

According to an embodiment of the present invention, in the above method, the bearing member is supported by the wear body in such a manner that the supporting angle can be adjusted and the adjusted position can be fixed.

According to another aspect of the present invention, an adjustment method for an auxiliary support apparatus is provided, wherein the adjustment method for the auxiliary support apparatus comprises the following steps:

(a) switching the auxiliary support apparatus from a supporting state to an unsupporting state;

(b) changing the size of a support angle between a bearing member of the auxiliary support apparatus and a wear body; and (c) switching the auxiliary support apparatus from the unsupporting state to the supporting state, so as to fix the changed support angle.

According to one embodiment of the present invention, the step (b) is implemented as:

increasing the support angle between the bearing member of the auxiliary support apparatus and the wear body.

According to an embodiment of the present invention, the step (b) is implemented as:

reducing the support angle between the bearing member of the auxiliary support apparatus and the wear body.

According to an embodiment of the present invention, the step (b) is implemented as:

reducing the support angle between the bearing member of the auxiliary support apparatus and the wear body in such a manner that downwardly rotating the bearing member.

According to an embodiment of the present invention, the step (b) is implemented as:

changing the support angle between the bearing member and the wear body by rotating the bearing member in any direction forward or backward.

One skilled in the art will understand that the embodiment of the present invention as shown in the drawings and described above is exemplary only and not intended to be limiting. It will thus be seen that the objects of the present invention have been fully and effectively accomplished. The embodiments have been shown and described for the purposes of illustrating the functional and structural principles of the present invention and is subject to change without departure from such principles. Therefore, this invention includes all modifications encompassed within the spirit and scope of the following claims.

What is claimed is:

1. An auxiliary support apparatus for wearing on a user, comprising: a wear member comprising a wear body arranged for wearing on a chest of the user, wherein said wear body is downwardly extended from said bearing member, wherein said bearing member is foldably and adjustably connected to said wear body to define a support angle between said bearing member and said wear body such that said support angle is able to be adjusted by selectively folding said bearing member towards said wear body and folding said bearing member away from said wear body so as to adjust a height of said auxiliary support apparatus and to position said bearing member at a front of the head of the user for supporting a jawbone of the head of the user so as to bear the head of the user; a bearing member arranged for supporting a head of the user and being configured to be pivotally rotated with respect to said wear body; and at least one fixing unit, formed between said bearing member and said wear body of said wear member, having a through hole formed in one end of said wear body, and comprising a gear rotating shaft arranged to an end portion of said bearing member and a lever, wherein said gear rotating shaft is received in said through hole, wherein said gear rotating shaft which is rotated with respect to a position of said through hole comprises a shaft main body and a wheel gear formed outside said shaft main body, wherein said lever is supported to said wheel gear such that said wheel gear is configured to only be rotated in one direction under a control of said lever, wherein said wheel gear has a plurality of gear teeth adapted for determining a rotated angle of said bearing member and said wear body with respect to each other after each adjustment; wherein said at least one fixing unit further comprises a housing and an elastic member connected to said housing, wherein said lever is rotatably connected to said housing and is operatively switched between a blocking state and a non-blocking state, wherein in the blocking state, said elastic member restricts a movement of said lever such that said lever is supported to said gear rotating shaft while said gear rotating shaft is able to move in one direction, wherein in the non-blocking state, said lever is disengaged from said gear rotating shaft to enable said gear rotating shaft to be rotated forward or backward at random, thereby when said lever is driven to move away from said gear rotating shaft in the blocking state while pressing said elastic member to deform, and when a driving force to said lever disappears or is weakened to less than an elastic force of said elastic member, said elastic member automatically drives said lever to return to the blocking state, wherein said lever comprises a stopper portion, a support and a pressing portion, wherein said stopper portion is movably engaged with said wheel gear, said pressing portion is extended outside said housing through said support, wherein said pressing portion and said stopper portion a levering element around said support, such that when said pressing portion is pressed, said stopper portion moves upwardly away from said wheel gear and said bearing member is able to move in a direction approaching said wear body, and that when a pressing of said pressing portion is released, said elastic member applies a pressure against said stopper portion to engage said stopper portion with said wheel gear and said bearing member is able to move away from said wear body, thereby said bearing member is blocked to be moved toward said wear body.

2. The auxiliary support apparatus, as recited in claim 1, wherein said lever is coupled to said wheel gear for providing a supporting force to said wheel gear of said gear rotating shaft while said supporting force determines a rotation direction of said gear rotating shaft, such that said bearing member is able to move in a direction away from said wear body and said lever prevents said gear rotating shaft from rotating in an opposite direction, thereby when said bearing member is lifted upwards, said bearing member is able to be held at a fixed angle due to said lever preventing a downward resetting movement of said bearing member.

3. The auxiliary support apparatus, as recited in claim 2, wherein said lever is configured to enable aid gear rotating shaft to rotate in a fixed direction and said gear rotating shaft is movable forwardly in a direction of said supporting force provided by said lever, thereby once said gear rotating shaft moves in a direction opposite to said supporting force provided by said lever, said wheel gear is locked and said gear rotating shaft is prevented to continue to move in the direction opposite to said supporting force provided by said lever.

4. The auxiliary support apparatus, as recited in claim 3, further comprising an adjustment unit comprising an adjusting mechanism and two adjustment members, wherein said wear body comprises a first support arm and a second support arm which are foldably connected to define an included angle therebetween for supporting on the chest of the user, wherein said adjustment unit is positioned between said first support arm and said second support arm and is connected to said first support arm and said second support arm, wherein said adjusting mechanism is connected to said two adjustment members for adjusting said adjustment members, so as to change a length of said adjustment unit and positions of said first support arm and said support arm respectively connected to two ends of said adjustment unit and to change an included angle defined between said first support arm and said second support arm, such that said adjustment unit is capable of restricting a relative displacement between said first support arm and said second support arm, and a relative displacement between said first bearing arm and said second bearing arm is restricted by said first support arm and said second support arm, and that folding ranges and adjusting ranges of said first support arm and said second support arm are able to be kept to be consistent, and the folding ranges and the adjusting ranges of said first bearing arm driven by said first support arm and said second bearing arm driven by said second support arm are able to be kept to be consistent.

5. The auxiliary support apparatus, as recited in claim 4, wherein said wear member further comprises a foldable auxiliary wear support which is configured to define a wear passage between said bearing member and said auxiliary wear support adapted for the head of the user to pass through, so that said bearing member is positioned in front of the head of the user and said auxiliary wear support is positioned at a rear of the head of the user for supporting a rear of a neck of the user, wherein said bearing member comprises a first bearing arm and a second bearing arm which are pivotally connected to define an including angle therebetween and shaped for fittingly attaching to the jawbone of the head of the user so as to support the head of the user, wherein said including angle is adjustable by selectively folding pivotally said first bearing arm and said second bearing arm towards each other so as to reduce a width of said bearing member or folding pivotally said first bearing arm and said second bearing arm away from each other so as to increase a width of said bearing member, wherein said wear body comprises a first support arm and a second support arm which are foldably connected to define an included angle therebetween for supporting on a chest of the user, wherein said included angle is adjustable by selectively folding said first support arm and said second support arm towards each other so as to reduce a width of said wear body or folding said first support arm and said second support arm away from each other to increase a width of said wear body, wherein an adjustment of said included angle of said wear body adjusts said including angle of said bearing member synchronously and an adjustment of said including angle of said bearing member also adjusts said included angle of said wear body synchronously.

6. The auxiliary support apparatus, as recited in claim 1, further comprising an adjustment unit, wherein said wear body comprises a first support arm and a second support arm which are foldably connected to define an included angle therebetween for supporting on the chest of the user, wherein said adjustment unit is capable of restricting a relative displacement between said first support arm and said second support arm, and a relatively displacement between said first bearing arm and said second bearing arm is restricted by said first support arm and said second support arm, wherein said adjustment unit is positioned between said first support arm and said second support arm and is connected to said first support arm and said second support arm, such that folding ranges and adjusting ranges of said first support arm and said second support arm are able to be kept to be consistent, wherein the folding ranges and the adjusting ranges of said first bearing arm driven by said first support arm and said second bearing arm driven by said second support arm are able to be kept to be consistent.

7. The auxiliary support apparatus, as recited in claim 6, wherein said adjustment unit comprises an adjusting mechanism and two adjustment members, wherein said adjusting mechanism is connected to said two adjustment members for adjusting said adjustment members, so as to change a length of said adjustment unit and positions of said first support arm and said support arm respectively connected to two ends of said adjustment unit and to change the included angle defined between said first support arm and said second support arm.

8. The auxiliary support apparatus, as recited in claim 1, wherein said wear member further comprises a foldable auxiliary wear support which is configured to define a wear passage between said bearing member and said auxiliary wear support adapted for the head of the user to pass through, so that said bearing member is positioned in front of the head of the user and said auxiliary wear support is positioned at a rear of the head of the user for supporting a rear of a neck of the user, wherein said bearing member comprises a first bearing arm and a second bearing arm which are pivotally connected to define an including angle therebetween and shaped for fittingly attaching to the jawbone of the head of the user so as to support the head of the user, wherein said including angle is adjustable by selectively folding pivotally said first bearing arm and said second bearing arm towards each other so as to reduce a width of said bearing member or folding pivotally said first bearing arm and said second bearing arm away from each other so as to increase a width of said bearing member, wherein said wear body comprises a first support arm and a second support arm which are foldably connected to define an included angle therebetween for supporting on a chest of the user, wherein said included angle is adjustable by selectively folding said first support arm and said second support arm towards each other so as to reduce a width of said wear body or folding said first support arm and said second support arm away from each other to increase a width of said wear body, wherein an adjustment of said included angle of said wear body adjusts said including angle of said bearing member synchronously and an adjustment of said including angle of said bearing member also adjusts said included angle of said wear body synchronously.

9. The auxiliary support apparatus, as recited in claim 2, wherein said wear member further comprises a foldable auxiliary wear support which is configured to define a wear passage between said bearing member and said auxiliary wear support adapted for the head of the user to pass through, so that said bearing member is positioned in front of the head of the user and said auxiliary wear support is positioned at a rear of the head of the user for supporting a rear of a neck of the user, wherein said bearing member comprises a first bearing arm and a second bearing arm which are pivotally connected to define an including angle therebetween and shaped for fittingly attaching to the jawbone of the head of the user so as to support the head of the user, wherein said including angle is adjustable by selectively folding pivotally said first bearing arm and said second bearing arm towards each other so as to reduce a width of said bearing member or folding pivotally said first bearing arm and said second bearing arm away from each other so as to increase a width of said bearing member, wherein said wear body comprises a first support arm and a second support arm which are foldably connected to define an included angle therebetween for supporting on a chest of the user, wherein said included angle is adjustable by selectively folding said first support arm and said second support arm towards each other so as to reduce a width of said wear body or folding said first support arm and said second support arm away from each other to increase a width of said wear body, wherein an adjustment of said included angle of said wear body adjusts said including angle of said bearing member synchronously and an adjustment of said including angle of said bearing member also adjusts said included angle of said wear body synchronously.

\* \* \* \* \*